(12) United States Patent
Woodrow et al.

(10) Patent No.: US 9,393,216 B2
(45) Date of Patent: Jul. 19, 2016

(54) VAGINAL MATRICES: NANOFIBERS FOR CONTRACEPTION AND PREVENTION OF HIV INFECTION

(71) Applicant: UNIVERSITY OF WASHINGTON THROUGH ITS CENTER FOR COMMERCIALIZATION, Seattle, WA (US)

(72) Inventors: Kim A. Woodrow, Seattle, WA (US); Cameron Ball, Seattle, WA (US); Anna Blakney, Seattle, WA (US); Emily Krogstad, Seattle, WA (US); Huarong Nie, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 14/073,734

(22) Filed: Nov. 6, 2013

(65) Prior Publication Data
US 2014/0128345 A1    May 8, 2014

Related U.S. Application Data

(60) Provisional application No. 61/857,148, filed on Jul. 22, 2013, provisional application No. 61/723,024, filed on Nov. 6, 2012.

(51) Int. Cl.
| | | |
|---|---|---|
| A61K 9/70 | (2006.01) |
| A61K 31/46 | (2006.01) |
| A61K 31/505 | (2006.01) |
| A61K 31/513 | (2006.01) |
| A61K 31/675 | (2006.01) |
| A61K 47/32 | (2006.01) |
| A61K 45/06 | (2006.01) |
| D01D 5/00 | (2006.01) |
| D01F 1/10 | (2006.01) |
| A61K 31/23 | (2006.01) |
| A61K 31/522 | (2006.01) |
| A61K 31/567 | (2006.01) |
| A61K 31/7072 | (2006.01) |
| A61F 6/06 | (2006.01) |
| A61K 9/00 | (2006.01) |
| A61K 47/10 | (2006.01) |
| A61K 47/34 | (2006.01) |
| A61K 47/38 | (2006.01) |

(52) U.S. Cl.
CPC ... *A61K 9/70* (2013.01); *A61F 6/06* (2013.01); *A61K 9/0034* (2013.01); *A61K 31/23* (2013.01); *A61K 31/46* (2013.01); *A61K 31/505* (2013.01); *A61K 31/513* (2013.01); *A61K 31/522* (2013.01); *A61K 31/567* (2013.01); *A61K 31/675* (2013.01); *A61K 31/7072* (2013.01); *A61K 45/06* (2013.01); *A61K 47/32* (2013.01); *D01D 5/0007* (2013.01); *D01F 1/103* (2013.01); *A61K 9/0031* (2013.01); *A61K 9/0036* (2013.01); *A61K 47/10* (2013.01); *A61K 47/34* (2013.01); *A61K 47/38* (2013.01)

(58) Field of Classification Search
CPC ...................................... A61K 9/70
See application file for complete search history.

(56) References Cited

U.S. PATENT DOCUMENTS

| | | |
|---|---|---|
| 8,057,817 B2 | 11/2011 | Shalaby |
| 2006/0200232 A1 | 9/2006 | Phaneuf et al. |
| 2008/0069850 A1 | 3/2008 | Shalaby et al. |
| 2010/0062039 A1* | 3/2010 | Shalaby ........................ 424/432 |
| 2010/0166854 A1 | 7/2010 | Michniak-Kohn et al. |
| 2010/0330138 A1 | 12/2010 | Shalaby et al. |
| 2011/0045041 A1 | 2/2011 | Golubovic-Liakopoulos et al. |

OTHER PUBLICATIONS

Brewster ME, Verreck G, Chun I, Rosenblatt J, Mensch J, Van Dijck A, Noppe M, Ariën A, Bruining M, Peeters J. The use of polymer-based electrospun nanofibers containing amorphous drug dispersions for the delivery of poorly water-soluble pharmaceuticals. Pharmazie. May 2004;59(5):387-91.*
Center for Drug Evaluation and Research Application Number: NDA 20-683. 1996.*
Chemical Book. Tenofovir. 2015.*
Li D, Wang Y, Xia Y. Electrospinning Nanofibers as Uniaxially Aligned Arrays and Layer-by-Layer Stacked Films. Advacned Materials. 2004; 16(4): 361-366.*
Li D, Xia Y. Electrospinning of Nanofibers: Reinventing the Wheel? Advanced Materials. 2004; 16(14): 1151-1170.*
Thurman AR, Clark MR, Doncel GF. Multipurpose prevention technologies: biomedical tools to prevent HIV-1, HSV-2, and unintended pregnancies. Infect Dis Obstet Gynecol. 2011;2011:1-10. Epub Aug. 9, 2011.*
Yu DG, Zhu LM, White K, Branford-White C. Electrospun nanofiber-based drug delivery systems. Health. 2009; 1(2): 67-75.*
Zhang et al., Biomacromolecules 7:1049-1057 (2006). "Coaxial Electrospinning of (Fluorescein Isothiocyanate-Conjugated Bovine Serum Albumin)-Encapsulated Poly(ε-caprolactone) Nanofibers for Sustained Release."
Maretschek et al., J of Controlled Release 127:180-187 (2008). "Electrospun biodegradable nanofiber nonwovens for controlled release of proteins."
Ionescu et al., Biomaterials 31(14):4113-4120 (2010). "An anisotropic nanofiber/microsphere composite with controlled release of biomolecules for fibrous tissue engineering."

(Continued)

*Primary Examiner* — Paul Zarek
(74) *Attorney, Agent, or Firm* — Nixon Peabody LLP; Mark J. FitzGerald

(57) ABSTRACT

Described are drug delivery systems incorporating electrospun fibers that comprise and deliver physicochemically diverse drug compounds. Such fibers provide significant advantages in drug agent release, such as adaptability for solid dosage delivery to mucosal tissues. This is in addition to allowing for controlled drug release. Systems and methods for large-scale electrospinning productivity are described, including novel microarchitectures allowing for variable pharmacokinetics in drug release.

21 Claims, 44 Drawing Sheets

(56) References Cited

OTHER PUBLICATIONS

Wei et al., J Control Release 112(1):103-110 (2006). "Nano-fibrous scaffold for controlled delivery of recombinant human PDGF-BB."
Chiu et al., J Biomed Mater Res A 83(4):1117-1127 (2007). "Functionalization of poly(L-lactide) nanofibrous scaffolds with bioactive collagen molecules."
Jin et al., PLOS One 3(3):e1729 (2008). "Nanofibrous scaffolds incorporating PDGF-BB Microspheres induce chemokine expression and tissue neogenesis in vivo."
Liang et al., Nucelic Aid Research 33(19):e170 (2005. "In vitro non-viral gene delivery with nanofibrous scaffolds."
Wang et al., Journal of Applied Polymer Science 115:1769-1780 (2010). "Effects of experimental parameters on the formation of chitosan-poly(acrylic-acid) nanofibrous scaffolds and evaluation of their potential application as DNA carrier."
Cao et al., Journal of Controlled Release 144:203-212 (2010). "RNA interference by nanofiber-based siRNA delivery system."
Kim et al., Journal of Controlled Release 145:264-271 (2010). "MMPs-responsive release of DNA from electrospun nanofibrous matrix for local gene therapy: in vitro and in vivo evaluation."
Karim et al., Science 329(5996):1168-1174 (2010). "Effectiveness and safety of tenofovir gel, an antiretroviral microbicide, for the prevention of HIV infection in women."
Rohan et al., PLOS One 5(2):e9310 (2010). "In vitro and ex vivo testing of tenofovir shows it is effective as an HIV-1 microbicide."
Zidovetzki et al., Biochim Biophys Acta. 1768(6):1311-1324 (2007). "Use of cyclodextrins to manipulate plasma membrane cholesterol content: evidence, misconceptions and control strategies."
Brener et al., Biology of Reproduction 68:837-845 (2003). "Remodeling of the actin cytoskeleton during mammalian sperm capacitation and acrosome reaction."
Choi et al., Biology of Reproduction 59:1328-1333 (1998). "Cyclodextrin removes cholesterol from mouse sperm and induces capacitation in a protein-free medium."
Ketas et al., Virology 364:431-440 (2007). "Entry inhibitor-based microbicides are active in vitro against HIV-1 isolates from multiple genetic subtypes."
Tsai et al., AIDS Research and Human Retroviruses 20(1)11-18 (2004). "Cyanovirin-N inhibits AIDS virus infections in vaginal transmission models."
Tsai et al., AIDS Research and Human Retroviruses 19(7):535-541 (2003). "Cyanovirin-N gel as a topical microbicide prevents rectal transmission of SHIV89.6P in macaques.".
Mori et al., Am J Obstet Gynecol 161(1):207-211 (1989). "Significance of D-mannose as a sperm receptor site on the zona pellucida in human fertilization."
Benoff et al., Fertility and Sterility 59(4):854-862 (1993). "Human sperm fertilizing potential in vitro is correlated with differential expression of a head-specific mannose-ligand receptor."
Chen et al., Journal of Andrology 16(1):55-63 (1995). "Expression of mannose-binding sites on human spermatozoa and their role in sperm-zona pellucida binding."
Wang et al., Biology of Reproduction 77:476-484 (2007). "Characterization of an Eppin protein complex from human semen and spermatozoa."
O'Rand et al., Biology of Reproduction 80:279-285 (2009). "Inhibition of human sperm motility by contraceptive anti-eppin antibodies from inferitle male monkeys: effect on cyclic adenosine monophosphate."
Robert et al., Molecular Human Reproduction 10(8):2192-2197 (1995). "Sperm motility inhibitor from human seminal plasma: association with semen coagulum."
Robert et al., Biology of Reproduction 55:813-821 (1996). "Purification and characterization of the active precursor of a human sperm motility inhibitor secreted by the seminal vesicles: identity with semenogelin."
Robert et al., Cell Mol Life Sci 55:944-960 (1999). "Semenogelin I: a coagulum forming, multifunctional seminal vesicle protein."
Li et al., Journal of Biomedical Materials Research 60(4):614-621 (2002). "Electrospun nanofibrous structure: a novel scaffold for tissue engineering."
Yoshimoto et al., Biomaterials 24:2077-2082 (2003). "A biodegradable nanofiber scaffold by electrospinning and its potential for bone tissue engineering."
Xu et al., Tissue Engineering 10(7/8):1160-1168 (2004). "Electrospun nanofiber fabrication as synthetic extracellular matrix and its potential for vascular tissue engineering."
Venugopal et al., Cell Biology International 29:861-867 (2005). "In vitro study of smooth muscle cells on polycaprolactone and collagen nanofibrous matrices."
Boland et al., J Biomed Mater Res B Appl Biomater 71(1):144-152 (2004). "Utilizing acid pretreatment and electrospinning to improve biocompatibility of poly(glycolic acid) for tissue engineering."
Yang et al., J Biomater. Sci. Polymer Edn 15(12):1483-1497 (2004). "Characterization of neural stem cells on electrospun poly(L-lactic acid) nanofibrous scaffold."
Yang et al., Biomaterials 26:2603-2610 (2005). "Electrospinning of nano/micro scale poly(L-lactic acid) aligned fibers and their potential in neural tissue engineering."
Li et al., Acta Biomaterialia 2:377-385 (2006). "Fabrication and characterizaiton of six electrospun poly(alpha-hydroxy ester)-based fibrous scaffolds for tissue engineering applications."
Boland et al., Acta Biomaterialia 1:115-123 (2005). "Electrospinning polydioxanone for biomedical applications."
Rho et al., Biomaterials 27:1452-1461 (2006). "Electrospinning of collagen nanofibers: effects on the behavior of normal human keratinocytes and early-stage wound healing."
Matthews et al., Biomacromolecules 3:232-238 (2002). "Electrospinning of collagen naofibers."
Li et al., Biomaterials 26:5999-6008 (2005). "Electrospun protein fibers as matrices for tissue engineering."
Buttafoco et al., Biomaterials 27:724-734 (2006). "Electrospinning of collagen and elastin fo tissue engineering applications."
Min et al., Biomaterials 25:1289-1297 (2004). "Electrospinning of silk fibroin nanofibers and its effect on the adhesion and spreading of normal human keratinocytes and fibroblasts in vitro."
Min et al., International Journal of Biological Macromolecules 34:223-230 (2004). "Formation of silk fibroin matrices with different texture and its cellular response to normal human keratinocytes."
WHO Special Programme of Research Development and Research Training in Human Reproduction, Journal of Steroid Biochemistry 11:461-467 (1979). "Intravaginal and intracervical devices for the delivery of fertility regulating agents."
Geng et al., Biomaterials 26:5427-5432 (2005). "Electrospinning of chitosan dissolved in concentrated acetic acid solution."
Bhattarai et al., Biomaterials 26:6176-6184 (2005). "Electrospun chitosan-based nanofibers and their cellular compatibility."
Jiang et al., Biomacromolecules 5:326-333 (2004). "Optimization and characterization of dextran membranes prepared by electrospinning."
Woerdman et al., Biomacromolecules 6:707-712 (2005). "Electrospun fibers from wheat protein: investigation of the interplay between molecular structure and the fluid dynamics of the electrospinning process."
Khil et al., J Biomet Mater Res B Appl Biomater 67(2):675-679 (2003). "Electrospun nanofibrous polyurethane membrane as wound dressing."
Doshi et al., Journal of Electrostatics 3:151-160 (1995). "Electrospinning process and applications of electrospun fibers."
Henry et al., J Biomed Mater Res A 82(3):669-679 (2007). "Characterization of a slowly degrading biodegradable polyesterurethane for tissue engineering scaffolds."
Megelski et al., Macromolecules 35:8456-8466 (2002). "Micro- and Nanostructured surface morphology on electrospun polymer fibers."
Abramoff et al., Biophotonics International 11(7):36-43 (2004). "Image processing with ImageJ."
Pham et al., Biomacromolecules 7:2796-7805 (2006). "Electrospun poly(epsilon-caprolactone) microfiber and multilayer nanofiber/microfiber scaffolds: characterization of scaffolds and measurement of cellular infiltration."

(56) References Cited

OTHER PUBLICATIONS

Rose et al., J. Agric. Food Chem. 39:2-11 (1991). "Starch determination by perchloric acid vs enzymes: evaluating the accuracy and precision of six colorimetric methods."
Woodrow et al., 236th ACS National Meeting: Poster Session Aug. 18, 2008. "Sustained and localized gene silencing in vitro and in vivo using PLGA nanoparticles densely loaded with small interfering RNA."
Cummins et al., Antimicrobial Agents and Chemotherapy 51(5):1770-1779 (2007). "Preclinical testing of candidate topical microbicides for anti-human immunodeficiency virus type 1 activity and tissue toxicity in a human cervical explant culture."
Ham et al., Pharmaceutical Research 26(3):502-511 (2009). "Targeted delivery of PSC-RANTES for HIV-1 prevention using biodegradable nanoparticles."
Cross et al., 15:213-226 (1986). "Two simple methods for detecting acrosome-reacted human sperm."
Mauck et al., Tissue Engineering Part B 15(2):171-193 (2009). "Engineering on the straight and narrow: the mechanics of nanofibrous assemblies for fiber-reinforced tissue regeneration."
Theron et al., Nanotechnology 12:384-390 (2001). "Electrostatic field-assisted alignment of electrospun nanofibres."
Courtney et al., Biomaterials 27:3631-3638 (2006). "Design and analysis of tissue engineering scaffolds that mimic soft tissue mechanical anisotropy."
Ayres et al., Biomaterials 27(32):5524-5534 (2006). "Modulation of anisotropy in electrospun tissue-engineering scaffolds: analysis of fiber alignment by the fast Fourier transform."
Nerurkar et al., Journal of Orthopaedic Research 1018-1028 (2007). "Mechanics of oriented electrospun nanofibrous scaffolds for annulus fibrosus tissue engineering."
Kidoaki et al., J Biomed Mater Res B Appl Biomater 76(1):219-229 (2006). "Structural features and mechanical properties of In Situ-bonded meshes of segmented polyurethane electrospun from mixed solvents."
Tan et al., J Biomed Mater Res A 87(4):1034-1043 (2008). "Electrospinning of photocrosslinked and degradable fibrous scaffolds."
Gupta et al., Journal of Pharmaceutical Sciences 96(3):670-681 (2007). "Temperature and pH sensitive hydrogels: an approach towards smart semen-triggered vaginal microbicidal vehicles."
Burruano et al., Contraception 66:137-140 (2002). "Synthetic cervical mucus formulation."
Owen et al., Journal of Andrology 26(4):459-469 (2005). "A review of the physical and chemical properties of human semen and the formulation of a semen simulant."
McElrath et al., Antimicrobial Agents and Chemotherapy 54(2):763-772 (2010). "Ex Vivo comparison of microbicide efficacies for preventing HIV-1 genomic integration in intraepithelial vaginal cells."
Hladik et al., Immunity 26(2):257-270 (2007). "Initial events in establishing vaginal entry and infection by human immunodeficiency virus type-1."
Han et al., Tetrahedron 60:2447-2467 (2004). "Recent development of peptide coupling reagents in organic synthesis."
Allen et al., The American Journal of Anatomy 30(3):297-371 (1922). "The oestrous cycle in the mouse."
Hong et al., Cancer Res 10:221-228 (2010). "Changes in the mouse estrus cycle in response to brca1 inactivation suggest a potential link between risk factors for familial and sporadic ovarian cancer."
Greco et al., Advanced Drug Delivery Reviews 61(13):1203-1213 (2009). "Combination therapy: opportunities and challenges for polymer-drug conjugates as anticancer nanomedicines."
Mayer et al., Molecular Interventions 7(4):216-223 (2007). "Optimizing combination chemotherapy by controlling drug ratios."
Sosnik et al., Journal of Controlled Release: official journal of the controlled release society 138(1):2-15 (2009). "Drug delivery systems in HIV pharmacotherapy: what has been done and the challenges standing ahead."
Wu et al., Biomaterials 17(11):2450-2467 (2006). "Drug/device combinations for local drug therapies and infection prophylaxis."

Sengupta et al., Nature 436(7050):568-572 (2005). "Temporal targeting of tumour cells and neovasculature with a nanoscale delivery system."
Zhang et al., Chem Med Chem. 2(9):1268-1271 (2007). "Co-delivery of hydrophobic and hydrophilic drugs from nanoparticle-aptamer bioconjugates."
Prausnitz et al., Nature Biotechnology 26(11):1261-1268 (2008). "Transdermal drug delivery."
Madhav et al., Journal of controlled release: official journal of the controlled release society 140(1):2-11 (2009). "Orotransmucosal drug delivery systems: a review."
Burkman, Am. J. Obstet. Gynecol. 190(4 Suppl):S49-53 (2004). "The transdermal contraceptive system."
Kapil et al., Drug Development and Industrial Pharmacy 39(3):466-80 (2013). "Buccoadhesive films for once-a-day administration of rivastigmine: systematic formulation development and pharmacokinetic evaluation."
Lee et al., Biomaterials 29(13):2113-2124 (2008). "Dissolving microneedles for transdermal drug delivery."
das Neves et al., Pharmaceutical Research 29(6):1468-1484 (2012). "Polymeric nanoparticles affect the intracellular delivery, antiretroviral activity and cytotoxicity of the microbicide drug candidate dapivirine."
UNAIDS World AIDS Day Report (2011).
Stijnman et al., Food Hydrocolloids 25:1393-1398 (2011). "Electrospinning of food-grade polysaccharides."
Ball et al., PLOS One 7(11):e49792 (2012). "Drug-eluting fibers for HIV-1 inhibition and contraception."
Yao et al., Chem. Mater. 15:1860-1864 (2003). "Electrospinning and stabilization of fully hydrolyzed poly (vinyl alchol) fibers."
Agarwal et al., Plymer 49:5603-5621 (2008). "Use of electrospinning technique for biomedical applications."
Theron et al., Polymer 45:2017-2030 (2004). "Experimental investigation of the governing parameters in the electrospinning of polymer solutions."
Thigpen et al., "Antiretroviral preexposure prophylaxis for heterosexual HIV transmission in Botswana." The New England Journal of Medicine 367:423-434 (2012).
Van Damme et al., "Preexposure prophylaxis for HIV infection among African Women." The New England Journal of Medicine 367(5):411-422 (2012).
Veazey et al., "Protection of rhesus macaques from vaginal infection by vaginally delivered maraviroc, an inhibitor of HIV-1 entry via the CCR5 co-receptor." The Journal of Infectious Diseases 202(5):739-744 (2010).
Wei et al., "Emergence of Resistant Human Immunodeficiency Virus Type 1 in Patients Receiving Fusion Inhibitor (T-20) Monotherapy." Antimicrobial Agents and chemotherapy 46(6)1896-1905 (2002).
Xu et al., "Ultrafine PEG-PLA fibers loaded with both paclitaxel and doxorubicin hydrochloride and their in vitro cytotoxicity." European Journal of Pharmaceutics and Biopharmaceutics. 72:18-25 (2009).
Yang et al., "Influence of solvents on the formation of ultrathin uniform poly(vinyl pyrrolidone) nanofibers with electrospinning." J Polym Sci B Polym Phys.42:3721-3726 (2004).
Yu et al., "Solid dispersions in the form of electrospun core-sheath nanofibers." International Journal of Nanomedicine 6:3271-3280 (2011).
Zhao et al., "Asymmetric Synthesis of Maraviroc (UK-427,857)." Adv. Synth. Catal. 352:2291-2298 (2010).
Aral, International Journal of STD & AIDS 12:211-215 (2001). "Sexually transmitted diseases: magnitude, determinants and consequences."
Spiedel et al., Contraception 78:197-200 (2008). "The potential of long-acting reversible contraception to decrease unintended pregnancy."
Doncel, Human Reproduction Update 12(2):103-117 (2006). "Exploiting common targets in human fertilization and HIV infection: development of novel contraceptive microbicides."
Friend et al., Antiviral Research 88S:S47-S54 (2010). "Combining prvention of HIV-1, and other sexually transmitted infections and unintended pregnancies: development of dual-protection technologies."

(56) References Cited

OTHER PUBLICATIONS

Baeten et al., HIV/AIDS 45:360-369 (2007). "The influence of hormonal contraceptive use on HIV-1 transmission and disease progression."
Blish et al., American Journal of Reporductive Immunology 65:302-307 (2011). "Hormonal contraception and HIV-1 transmission."
Klasse et al., Annu. Rev. Med 59:455-471 (2008). "Antiretroviral drug-based microbicides to prevent HIV-1 sexual transmission."
Geonnotti et al., J. of pharmaceutical sciences 94(8):1705-1712 (2005). "Erosion of microbicide formulation coating layers: effects of contact and shearing with vaginal fluid or semen."
Achilles et al., Sexually Transmitted Disease 29(11):655-664 (2002). "Microbicide efficacy and toxicity tests in a mouse model for vaginal transmission of chlamydia trachomatis."
Zhang et al., Science 286:1352-1356 (1999). "Sexual transmission and propagation of SIV and HIV in resting and activated CD4+ T cells."
UNAIDS Report on the Global AIDS Epidemic (2010).
World Health Organization, Women and Health: Today's Evidence Tomorrow's Agenda (2009).
Hubacher et al., Contraception 28:73-78 (2008) "Unintended pregnancy in sub-Saharan Africa: magnitude of the problem and potential role of contraceptive implants to alleviate it."
AbouZahr et al., Maternal Mortality in 2000: Estimates Developed by WHO, UNICEF and UNFPA 1-39.
Gollub et al., International Family Planning Perspectives 32(4):209-212 (2006). "Choice is empowering: getting strategic about preventing HIV in women."
Minnis et al., Sex Transm Infect 81:193-200 (2005). "Effectiveness of female controlled barrier methods in preventing sexually transmitted infections and HIV: current evidence and future research directions."
Padian et al., Lancet 370(9583):251-261 (2007). "Diaphragm and lubricant gel for prevention of HIV acquisition in southern African women: a randomised controlled trial."
Ramjee et al., PLOS One 3(10)e3488 (2008). "The diaphragm and lubricant gel for prevention of cervical sexually transmitted infections: results of a randomized controlled trial."
Elder et al., Contraception 30(1):55-60 (1984). "Effect of a new contraceptive ring releasing 20 micrograms levonorgestrel daily on blood lipid levels and glucose tolerance."
Ji et al., Contraception 47:455-468 (1993). "Menstrual blood loss with use of a vaginal ring releasing 20 micrograms levonorgestrel per day."
Weisberg et al., Contraception 62:83-89 (2000). "A randomized comparison of the effects on vaginal and cervical epithelium of a placebo vaginal ring with non-use of a ring."
Koetsawang et al., Contraception 41(2):105-124 (1990). "Microdose intravaginal levonorgestrel contraception:a multicentre clinical trial."
Stringer et al., Am J Absteet Gynecol 197(2):144.e1-144.e8 (2007). "A randomized trial of the intrauterine contraceptive device vs hormonal contraception in women who are infected with the human immunodeficiency virus."
Leclerc et al., Contraception 77:371-376 (2008). "Hormonal contraceptiuon and HIV prevalence inf our African countries."
Hel et al., Endocr Rev 31(1):79-97 (2010). "Sex steroid hormones, hormonal contraception, and the immunobioogy of human immunodeficiency virus-1 infection."
Zhang et al., PNAS 101(15):5640-5645 (2004). "Roles of substrate availability and infection of resting and activated CD4+ T cells in transmission and acute simian immunodeficiency virus infection."
Major et al., 32nd Annual International Conference of the IEEE EMBS 1089-1092 (2010). "Development of a microbicide-releasing diaphragm as an HIV prevention strategy."
Jang et al., Advanced Drug Delivery Reviews 61:1065-1083 (2009). "Electrospun materials as potential platforms for bone tissue engineering."
Zhang et al., Nano Letters 8(10):3283-3287 (2008). "Electrospinning of three-dimensional nanofibrous tubes with controllable architectures."
Murugan et al., Tissue Engineering 12(2):435-488 (2006). "Nano-featured scaffolds for tissue engineering: a review of spinning methodologies."
Murugan et al., Tissue Engineering 13(8):1845-1866 (2007). "Design strategies of tissue engineering scaffolds with controlled fiber orientation."
Pham et al., Tissue Engineering 12(5):1197-1211 (2006). "Electrospinning of polymeric nanofibers for tissue engineering applications: a review."
Sill et al., Biomaterials 29:1989-2006 (2008). "Electrospinning: applications in drug delivery and tissue engineering."
Taepaiboon et al., Nanotechnology 17:2317-2329 (2006). "Drug-loaded electrospun mats of poly(vinyl alcohol ) fibres and their release characteristics of four model drugs."
Okuda et al., Journal of Controlled Release 143:258-264 (2010). "Time-programmed dual release formulation by multilayered drug-loaded nanofiber meshes."
Kidoaki et al., Biomaterials 26:37-46 (2005). "Mesoscopic spatial designs of nano- and microfiber meshes for tissue-engineering matrix and scaffold based on newly devised multilayering and mixing electrospinning techniques."
Curran et al., Vaccine 27:6791-6798 (2009). "Vaginal delivery of the recombinant HIV-1 clade-C trimeric gp140 envelope protein CN54gp140 within novel rheologically structured vehicles elicits specfic immune responses."
Andrews et al., Biomacromolecules 10:2427-2435 (2009). "Characterization of the rheological mucoadhesive, and drug release properties of highly structured gel platforms for intravaginal drug delivery."
Belcheva et al., Bioconjugate Che 10:932-937 (1999). "Synthesis and biological activity of polyethylene glycol-mouse nerve growth factor conjugate."
Luo et al., Pharmeceutical Research 16(8):1300-1309 (1999). "Controlled DNA delivery systems."
Woodrow et al., Nat. Mater. 8(6):526-533 (2009). "Intravaginal gene silencing using biodegradable polymer nanoparticals densely loaded with small-interfering RNA."
Woodrow et al., Tissue Engineering 15(5):1169-1179 (2009). "Biodegradable meshes printed with extracellular matrix proteins support micropatterned hepatocyte cultures."
Jiang et al., J of Controlled Release 108:237-243 (2005). "A facile technique to prepare biodegradable coaxial electrospun nanofibers for controlled release of bioactive agents."
Stitzel et al., Biomaterials 27:1088-1094 (2006). "Controlled fabcrication of a biological vascular substitute."
Luong-Van etal., Biomaterials 27:2042-2050 (2006). "Controlled release of heparin from poly(epsilon-caprolactone) electrospun fibers."
Huang et al., J of Biomedical Materials Research Part A 77(1):169-179 (2006). "Encapsulating drugs in biodegradable ultrafine fibers through co-axial electrospinning."
Cui et al., Biomacromolecules 7:1623-1629 (2006). "Investigation of drug release and matrix degradation of electrospun poly(DL-lactide) fibers with paracetanol inoculation."
Feng et al., J Control Release 146(3):363-369 (2010). "Novel antibacterial nanofibrous PLLA scaffolds."
Abel et al., "Assessment of the absorption metabolism and absolute bioavailability of maraviroc in healthy male subjects." Br J Clin Pharmacol 65(Suppl 1):60-67 (2008).
Baeten et al., "Antiretroviral prophylaxis for HIV prevention in heterosexual men and women." The New England Journal of Medicine 367(5):399-410 (2012).
Bednarek et al., "Safety, efficacy and patient acceptability of the contraceptive and non-contraceptive uses of the LNG-IUS." International Journal of Women's Health 1:45-58 (2009).
Chen et al., "Novel biodegradable sandwich-structured nanofibrous drug-eluting membranes for repair of infected wounds: an in vitro and in vivo study." International Journal of Nanomedicine 7:763-771 (2012).
Cocohoba et al., "Raltegravir: the first HIV integrase inhibitor." Clinical Therapeutics 30(10):1747-1765 (2008).

(56) References Cited

OTHER PUBLICATIONS

Dahlberg et al., "Polymer swelling, drug mobilization and drug recrystallization in hydrating solid dispersion tablets studied by multinuclear NMR microimaging and spectroscopy." Molecular Pharmaceutics 8:1247-1256 (2011).

Damme et al, "Effectiveness of Col-1492, a nonoxynol-9 vaginal gel, on HIV-1 transmission in female sex workers: a randomised controlled trial." The Lancet 360:971-977 (2002).

D'Cruz et al., "Conceival, a novel noncontraceptive vaginal vehicle for lipophilic microbicides." AAPS PharmSciTech 6 (1):E56-E64 (2005).

Derdeyn et al., "Sensitivity of human immunodeficiency virus type 1 to the fusion inhibitor T-20 is modulated by coreceptor specificity defined by the V3 loop of gp120." Journal of Virology 74(18):8358-8367 (2000).

Dhanaraju et al., "Preparation and characterization of injectable microspheres of contraceptive hormones." International Journal of Pharmaceutics 268:23-29 (2003).

Dorr et al., "Maraviroc (UK-427,857), a potent, orally bioavailable, and selective small-molecule inhibitor of chemokine receptor CCR5 with broad-spectrum anti-human immunodeficiency virus type 1 activity." Antimicrobial agents and chemotherapy 49(11):4721-4732 (2005).

Dumond et al., "Maraviroc concentrates in the cervicovaginal fluid and vaginal tissue of HIV-negative women,." J Acquir Immune Defic Syndr. 51(5):546-553 (2009).

Emmelkamp et al., "Maraviroc, risks and benefits: a review of the clinical literature." Expert Opin. Drug Saf. 7 (5):559-569 (2008).

Fetherston et al., "A slicone elastomer vaginal ring for HIV prevention containing two microbicides with different mechanisms of action." European Journal of Pharmaceutical Sciences 48:406-415 (2013).

Forbes et al., "Non-aqueous silicone elastomer gels as a vaginal microbicide delivery system for the HIV-1 entry inhibitor maraviroc." Journal of Controlled Release 156:161-169 (2011).

Frank et al., "The amorphous solid dispersion of the poorly soluble ABT-102 forms nano/microparticulate structures in aqueous medium: impact on solubility." International Journal of Nanomedicine 7:5757-5768 (2012).

Fung et al., "Tenofovir disoproxil fumarate: a nucleotide reverse transcriptase inhibitor for the treatment of HIV infection." Clinical Therapeutics 24(10):1515-1548 (2002).

Gallo et al., "Twenty micrograms vs. >20 microg estrogen oral contraceptives for contraception: systematic review of randomized controlled trials." Contraception 71(3):162-169 (2005).

Garcia-Lerma et al., "Intermittent prophylaxis with oral truvada protects macaques from rectal SHIV infection." Science Translation Medicine 2(14):14ra4 (2010).

Goh et al., "Electrospun fibers for tissue engineering, drug delivery, and wound dressing." J Mater Sci 48:3027-3054 (2013).

Grant et al., "Preexposure chemoprophylaxis for HIV prevention in men who have sex with men." N Engl J Med 363(27):2587-2599 (2010).

Huang et al., "Electrospun cellulose acetate phthalate fibers for semen induced anti-HIV vaginal drug delivery." Biomaterials 33:962-969 (2012).

Jain et al., "Proultraflexible lipid vesicles for effective transdermal delivery of levonorgestrel: development, characterization, and performance evaluation." AAPS PharmSciTech 6(3):E513-E522 (2005).

Jannesari et al., "Composite poly(vinyl alcohol)/poly(vinyl acetate) electrospun nanofibrous mats as a novel wound dressing matrix for controlled release of drugs." International Journal of Nanomedicine 6:993-1003 (2011).

Johnson et al., "Segmented polyurethane intravaginal rings for the sustained combined delivery of antiretroviral agents dapivirine and tenofovir." European Journal of Pharmaceutical Sciences 39:203-212 (2010).

Kanazawa "Thermally responsive chromatrographic materials using functional polymers." J. Sep. Sci. 30:1646-1656 (2007).

Li et al., "Electrospun polyvinyl-alcohol nanofibers as oral fast-dissolving delivery system of caffeine and riboflavin." Colloids and Surfaces B: Biointerfaces 103:182-188 (2013).

Lu et al., "Preparation and characterization of Ag2S nanoparticles embedded in polymer fibre matrices by electrospinning." Nanotechnology 16:2233-2237 (2005).

Malcolm et al., "Sustained release of the CCR5 inhibitors CMPD167 and maraviroc from vaginal rings in Rhesus macaques." Antimicrobial Agents and Chemotherapy 56(5):2251-2258 (2012).

Malcolm et al., "Pharmacokinetics and efficacy of a vaginally administered maraviroc gel in rhesus macaques." J Antimicrob Chemother 68:678-693 (2013).

Massud et al., "Lack of prophylactic efficacy of oral maraviroc in macaques despite high drug concentrations in rectal tissues." Journal of Virology 87(16):8952-8961 (2013).

Meng et al., "Engineering tenofovir loaded chitosan nanoparticles to maximize microbicide mucoadhesion." European Journal of Pharmaceutical Sciences 44:57-67 (2011).

Miao et al., "Electrospun fibers of layered double hydroxide/biopolymer nanocomposites as effective drug delivery systems." Materials Chemistry and Physics 134:623-630 (2012).

Morrow et al., "The acceptability of an investigational vaginal microbicide, PRO 2000 gel, among women in a phase I clinical trial." Journal of Women's Health 12(7):655-666 (2003).

"Multipurpose Prevention Technologies (MPTs) for Reproductive Health," 2012.

Neff et al., "Oral pre-exposure prophylaxis by anti-retrovirals raltegravir and maraviroc protects against HIV-1 vaginal transmission in a humanized mouse model." PLOS One 5(12):e15257 (2010).

Network MT. MTN Statement on decision to discontinue use of tenofovir gel in VOICE, a major HIV prevention study in women. Microbicide Trials Network. Nov. 25, 2011.

Nicol et al., "Pharmacologic opportunities for HIV prevention." Clin Pharmacol Ther. 88(5):598-609 (2010).

Notari et al., "Simultaneous determination of maraviroc and raltegravir in human plasma by HPLC-UV." IUBMB Life 61(4):470-475 (2009).

Platt et al., "Effects of CCR5 and CD4 cell surface concentrations on infections by macrophagetropic isolates of human immunodeficiency virus type 1." Journal of Virology 72(4):2855-2864 (1998).

Prabaharan et al., "Electrospun nanofibrous scaffolds-current status and prospects in drug delivery." Adv Polym Sci 246:241-262 (2012).

Ravel et al., "Vaginal microbiome of reproductive-age women." PNAS 108(suppl 1):4680-4687 (2011).

Roche et al., "HIV-1 predisposed to acquiring resistance to maraviroc (MVC) and other CCR5 antagonists in vitro has an inherent, low-level ability to utilize MVC-bound CCR5 for entry." Retrovirology 8:89 (2011).

Rohan et al., "Vaginal drug delivery systems for HIV prevention." The AAPS Journal 11(1):78-87 (2009).

Shao et al., "Fiber mats of poly(vinyl alcohol)/silica composite via electrospinning." Materials Letters 57:1579-1584 (2003).

Shenoy et al., "Role of chain entanglements on fiber formation during electrospinning of polymer solutions: good solvent, non-specific polymer-polymer interaction limit." Polymer 46:3372-3384 (2005).

Szentivanyi et al., "Production of biohybrid protein/PEO scaffolds by electrospinning." 40(1-2):65-72 (2009).

Takeuchi et al., "Identification of gammaretroviruses constitutively released from cell lines used for human immunodeficiency virus research." Journal of Virology 82(24):12585-12588 (2008).

Telford et al., "Thermally cross-linked PNVP films as antifouling coatings for biomedical applications." Applied Materials & Interfaces 2(8):2399-2408 (2010).

Teo et al., "A review on electrospinning design and nanofibre assemblies." Nanotechnology 17:R89-R106 (2006).

* cited by examiner

Figure 4.

| Fiber Type | Encapsulation Efficiency, %[a,b] LNG | Encapsulation Efficiency, %[a,b] TFV | Fiber Diameter, nm[b] | Yield, % | Productivity, g/m²/hr | Drug Crystallinity[b] LNG | Drug Crystallinity[b] TFV |
|---|---|---|---|---|---|---|---|
| Blank | - | - | 208±106 | 39.4 | 12.9 | - | - |
| Single-drug fabrics | | | | | | | |
| LNG Only | 100±1.1 (16.7%) | - | 260±105 | 33.8 | 18.0 | 1.2% | - |
| TFV Only | - | 85±1.3 (14.3%) | 267±176 | 49.9 | 18.0 | - | 0.2% |
| Multi-drug composite fabric | | | | | | | |
| Combined | 82±1.5 (11.6%) | 93±1.9 (14.3%) | 251±83 | 39.7 | 18.7 | n.d. | 2.3% |

Note: a) Drug loading is shown in parentheses (wt. drug/wt. fiber). b) Encapsulation efficiency, fiber diameter and drug crysalinity were measured using HPLC, SEM and DSC, respectively.

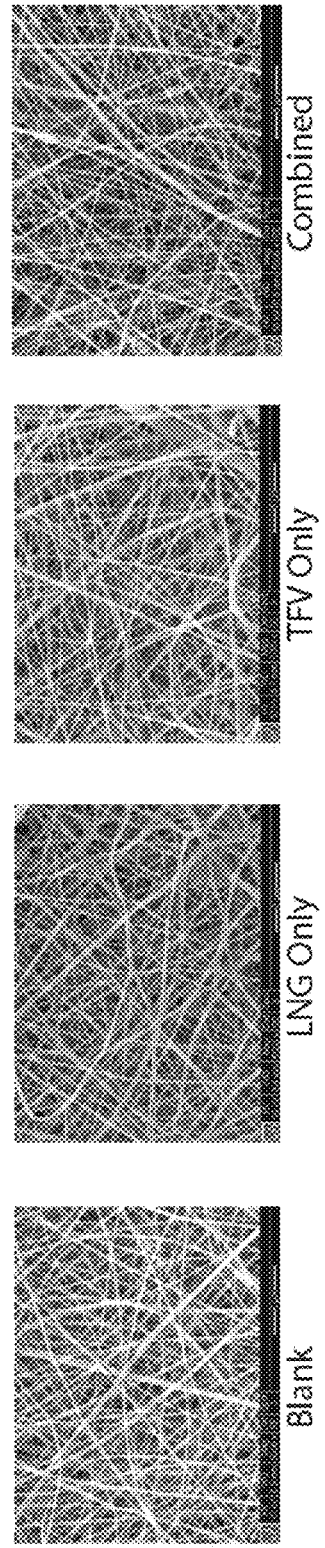

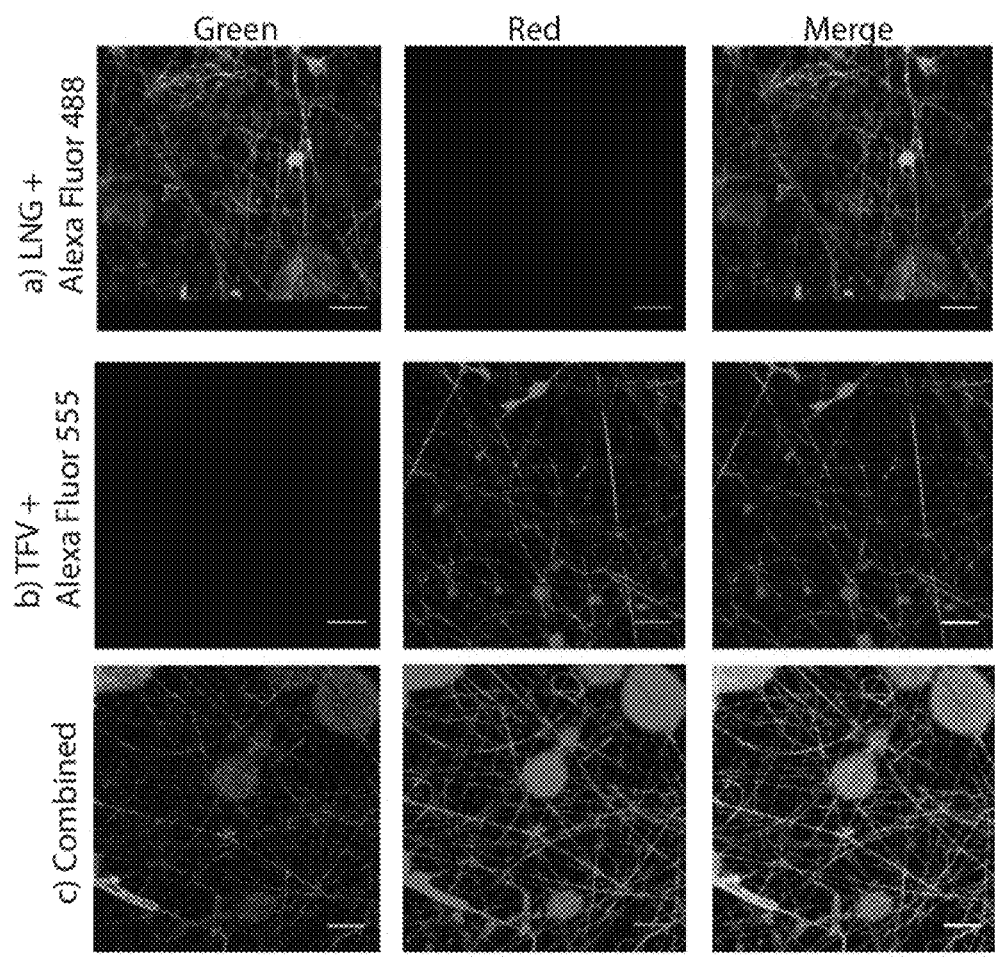

Figure 24.

|  | Fiber Diameter (nm) | | Thickness (mm) | | Mass Productivity (g/h) | |
| --- | --- | --- | --- | --- | --- | --- |
|  | Needle rig | Nanospider | Needle rig | Nanospider | Needle rig | Nanospider |
| 0% TFV, unadjusted | 301 ± 84 | 265 ± 68 | 0.07 ± 0.01 | 0.08 ± 0.01 | 0.043 | 5.54 |
| 0% TFV, pH 7 | 296 ± 87 | 243 ± 69 | 0.09 ± 0.00 | 0.12 ± 0.01 | 0.058 | 6.94 |
| 10% TFV, unadjusted | 205 ± 34 | 176 ± 55 | 0.14 ± 0.01 | 0.10 ± 0.01 | 0.067 | 5.56 |
| 10% TFV, pH 7 | 188 ± 44 | 155 ± 59 | 0.17 ± 0.02 | 0.05 ± 0.02 | 0.060 | 2.89 |
| 60% TFV, unadjusted | 184 ± 44 | 141 ± 65 | 0.22 ± 0.01 | 0.18 ± 0.01 | 0.135 | 7.64 |
| 60% TFV, pH 7 | 320 ± 70 | 242 ± 81 | 0.11 ± 0.03 | 0.05 ± 0.01 | 0.093 | 5.53 |

Fiber diameter represents average ± standard deviation (n=45 fibers). Thickness measurements represent average of triplicate measurements ± standard deviation. Mass productivity is defined as mass of final mesh divided by time to electrospin for 500 uL volume (small scale) or 30 min run time (large scale), with n=1.

Figure 27.

| | Actual Drug Loading (wt%) | | Drug Crystallinity (%) | |
|---|---|---|---|---|
| | Needle rig | Nanospider | Needle rig | Nanospider |
| 0% TFV, unadj | 0 | 0 | nd | nd |
| 0% TFV, pH 7 | 0 | 0 | nd | nd |
| 10% TFV, unadj | 7.5 | 7.3 | nd | nd |
| 10% TFV, pH 7 | 9.4 | 9.4 | nd | nd |
| 60% TFV, unadj | 59.2 | 49.7 | 86.7 | 90.8 |
| 60% TFV, pH 7 | 52.4 | 51.9 | nd | 2.2 |

Relative drug crystallinity was calculated from differential scanning calorimetry (DSC) thermograms and is reported as percentage of crystalline TFV in fibers relative to pure TFV standard, not accounting for any mass loss of material. Nd=not detectable.

Figure 35.
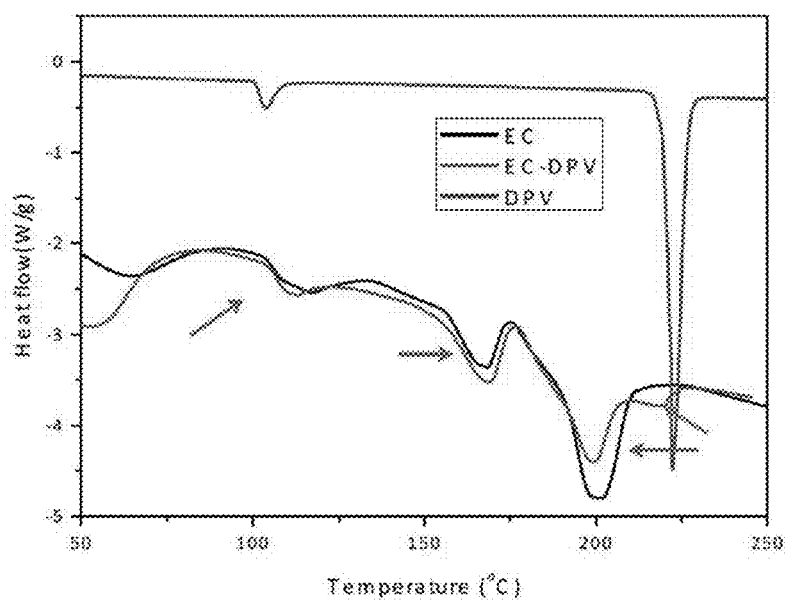
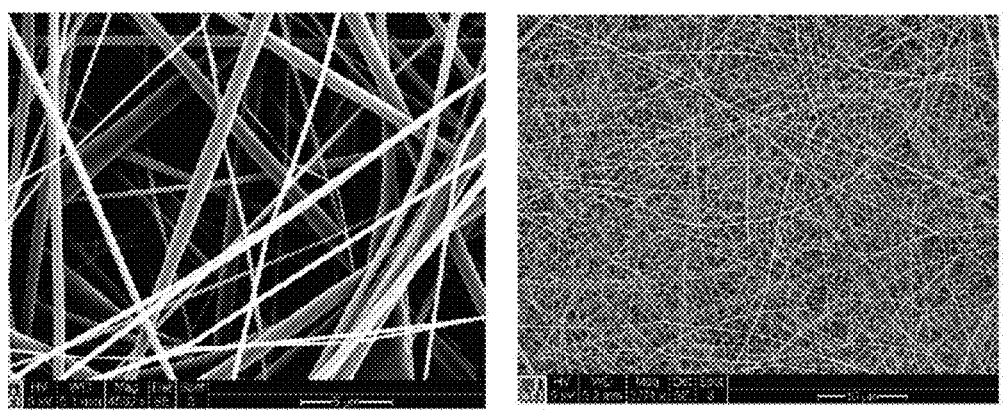

Figure 36.
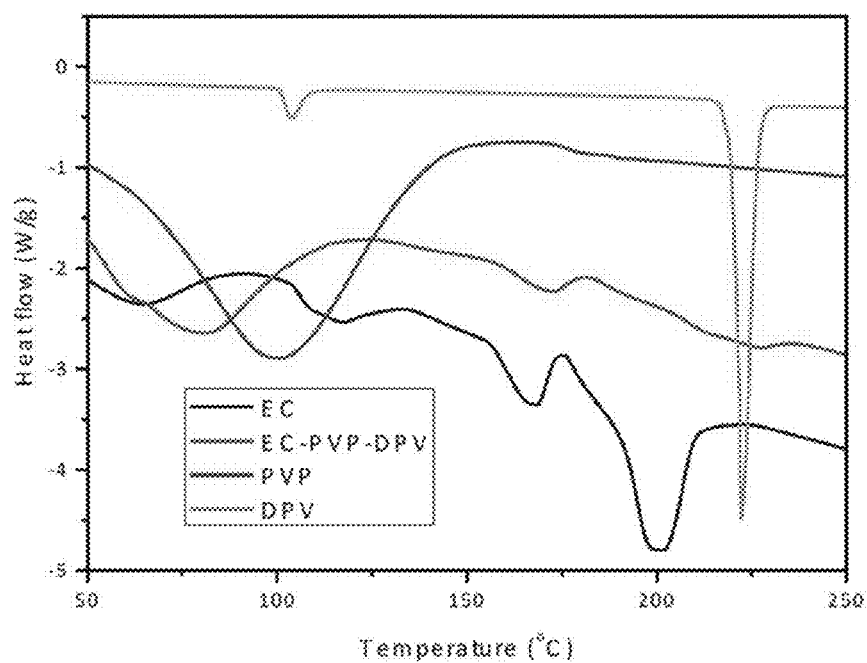
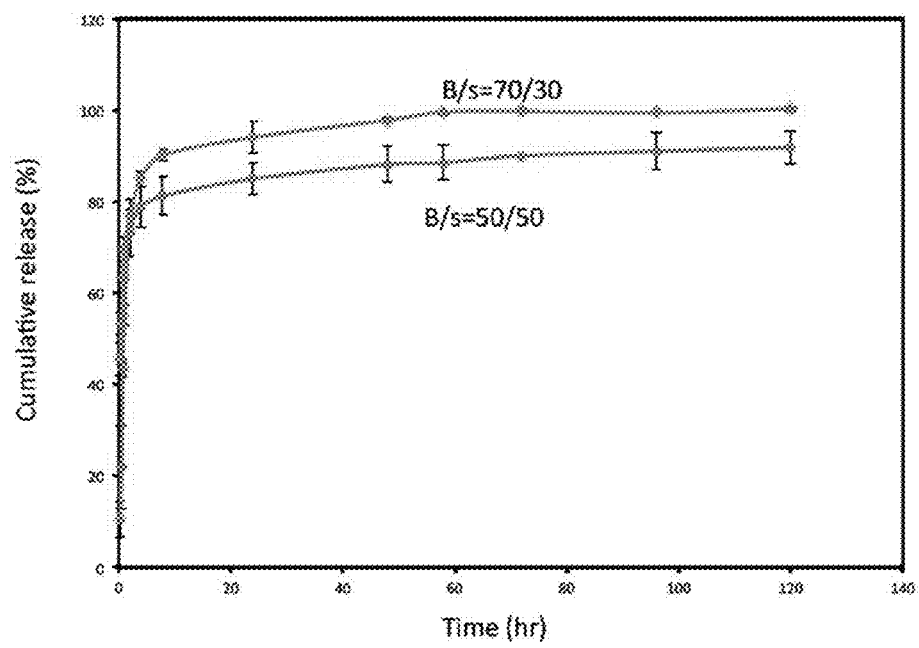

Figure 37
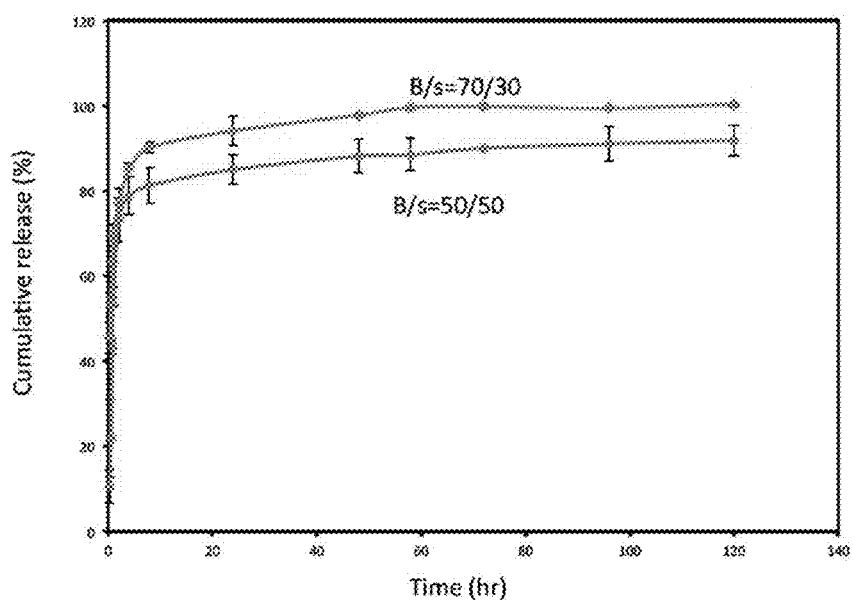
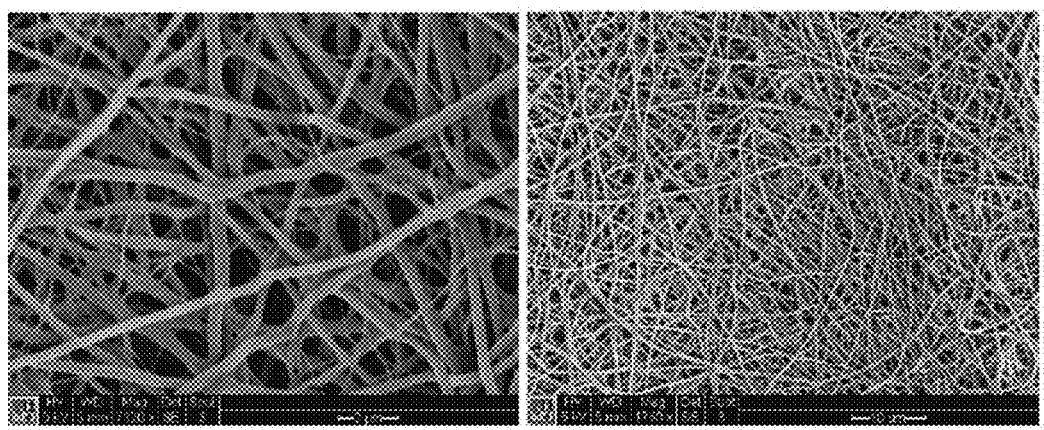

Figure 39.
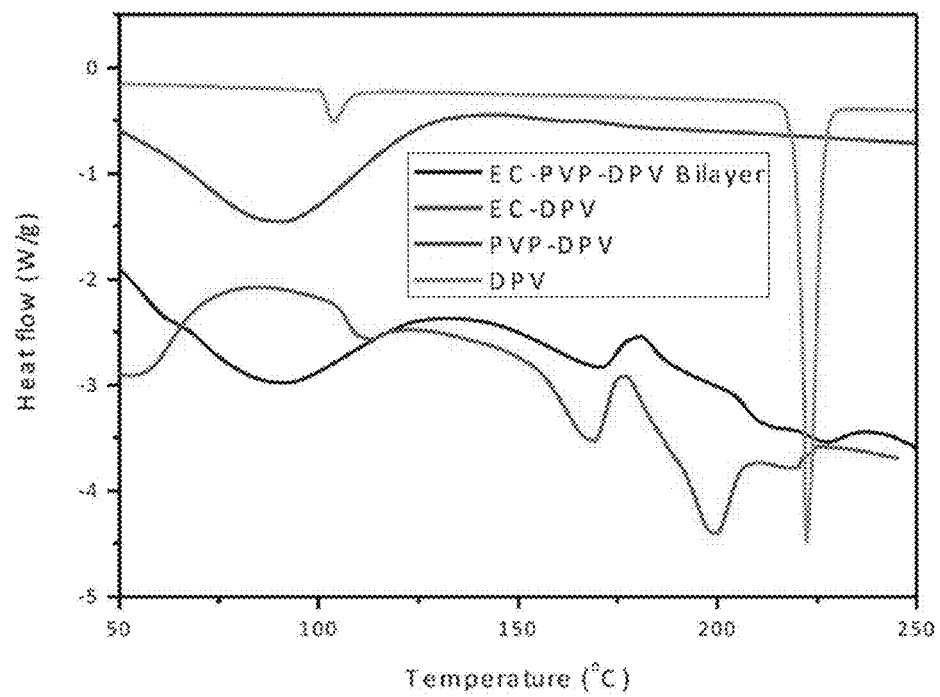
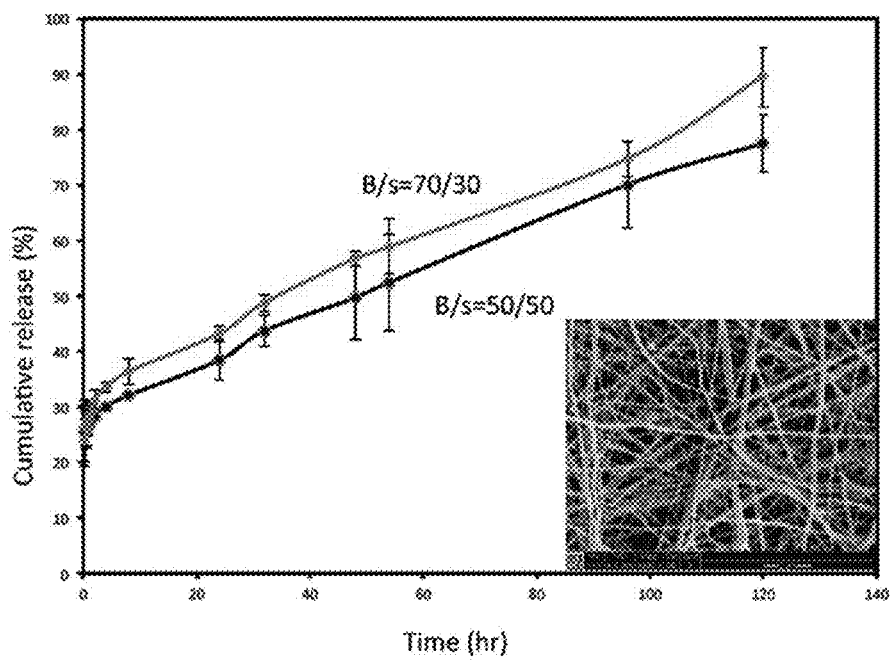

VAGINAL MATRICES: NANOFIBERS FOR CONTRACEPTION AND PREVENTION OF HIV INFECTION

CROSS-REFERENCE TO RELATED APPLICATIONS

This application claims priority under 35 U.S.C. §119(e) to U.S. provisional patent application No. 61/723,024, filed Nov. 6, 2012, and U.S. provisional patent application No. 61/857,148 filed Jul. 22, 2013.

GOVERNMENT RIGHTS

This invention was made with government support under Grant No. AI098648 awarded by the National Institutes of Health. The government has certain rights in the invention.

FIELD OF THE INVENTION

The present invention relates to drug delivery systems. More particularly, the invention relates to drug delivery systems incorporating electrospun fibers. Such materials can incorporate a variety of drug agents, including physicochemically diverse compounds. Systems and methods incorporating such drug delivery materials are described, including adjustments providing for advantages in drug profile release.

BACKGROUND

Drug combinations have been shown to have several advantages compared to treatment with a single therapeutic agent, including potential synergistic effects, fewer occurrences of drug resistance, and enhanced efficacy. Greco F, Vicent Ma. Combination therapy: opportunities and challenges for polymer-drug conjugates as anticancer nanomedicines. *Advanced drug delivery reviews.* 2009; 61(13):1203-13. The importance of drug combinations can be seen in applications ranging from treatment of cancer and HIV/AIDS to multi-drug resistant bacterial infections. Mayer L, Janoff A. Optimizing combination chemotherapy by controlling drug ratios. *Molecular interventions.* 2007; 7(4):216-23, Sosnik A, Chiappetta D, Carcaboso A. Drug delivery systems in HIV pharmacotherapy: what has been done and the challenges standing ahead. *Journal of controlled release: official journal of the Controlled Release Society.* 2009; 138(1):2-15, and Wu P, Grainger D. Drug/device combinations for local drug therapies and infection prophylaxis. Biomaterials. 2006; 27(11):2450-67. However, combining multiple drugs into a single treatment requires careful optimization to enhance therapeutic effects beyond that of a singular drug. Co-delivery of certain drug combinations may require novel delivery vehicles capable of combining hydrophilic and hydrophobic drugs, actively targeting certain cell populations, and controlling the temporal release of both drugs independently. Sengupta S, Eavarone D, Capila I, Zhao G, Watson N, Kiziltepe T, et al. Temporal targeting of tumour cells and neovasculature with a nanoscale delivery system. *Nature.* 2005; 436 (7050):568-72. Zhang L, Radovic-Moreno A, Alexis F, Gu F, Basto P, Bagalkot V, et al. Co-delivery of hydrophobic and hydrophilic drugs from nanoparticle-aptamer bioconjugates. *Chem Med Chem.* 2007; 2(9):1268-71. Developments in nanotechnology, such as particles and other delivery systems, present a new arena for overcoming these and other challenges associated with combination drug delivery.

Co-delivery is relevant to many topical delivery systems that target delivery of pharmaceutical agents either externally, such as to the skin or eye, or internally, such as to the mucous membranes of the mouth, vagina or rectum. Topical delivery is advantageous in that it avoids first pass metabolism, is convenient for and generally accepted by users, presents the opportunity for easily reversible treatment and may have smaller dosing requirements. Prausnitz M, Langer R. Transdermal drug delivery. *Nature biotechnology.* 2008; 26(11): 1261-8, Madhav N, Shakya A, Shakya P, Singh K. Orotransmucosal drug delivery systems: a review. *Journal of controlled release: official journal of the Controlled Release Society.* 2009; 140(1):2-11. Advances in topical delivery systems have yielded success with transdermal delivery of contraceptives, medical fabrics loaded with antibiotics for more effective wound healing, and buccal delivery of an anti-Alzheimer's drug. Burkman R. The transdermal contraceptive system. *American journal of obstetrics and gynecology.* 2004; 190(4 Suppl):53, Huang Z-M, He C-L, Yang A, Zhang Y, Han X-J, Yin J, et al. Encapsulating drugs in biodegradable ultrafine fibers through co-axial electrospinning. *Journal of biomedical materials research Part A.* 2006; 77(1):169-79, and Kapil R, Dhawan S, Beg S, Singh B. Buccoadhesive films for once-a-day administration of rivastigmine: systematic formulation development and pharmacokinetic evaluation. *Drug development and industrial pharmacy.* 2013; 39(3): 466-80. Novel delivery vehicles have expanded the potential to deliver more diverse drugs in a variety of applications. For example, dissolving microneedles made of polysaccharides developed by Lee et al. have allowed for precisely tuned delivery of both small molecules and biologics transdermally. Lee J, Park J-H, Prausnitz M. Dissolving microneedles for transdermal drug delivery. *Biomaterials.* 2008; 29(13):2113-24. das Neves et al. have developed mucosal-penetrating nanoparticles for the delivery of antiretrovirals to the vagina as HIV pre-exposure prophylaxis. das Neves J, Michiels J, Arien K, Vanham G, Amiji M, Bahia M, et al. Polymeric nanoparticles affect the intracellular delivery, antiretroviral activity and cytotoxicity of the microbicide drug candidate dapivirine. *Pharmaceutical research.* 2012; 29(6):1468-84. The expansion of deliverable drugs via topical delivery is permitted by the development of novel delivery systems that overcome the challenges associated with topical delivery, such as drug limitations based on solubility, particle size, molecular weight and polymorphism. However, delivery of drug combinations using topical systems has been largely unexplored due to a number of challenges associated with co-delivery, including delivery of physicochemically diverse drugs and difficulty in controlling independent release rates.

SUMMARY OF THE INVENTION

Described herein are electrospun fiber compositions comprising at least two physicochemically diverse drug agents. The fiber compositions are designed to release the different drugs, e.g., when implanted or when placed in contact with mucosal tissues, and to do so with either or both of burst or sustained/prolonged release kinetics. The compositions described can have varying microarchitecture established by manipulation of the electrospinning solution(s) and the parameters used for electrospinning. The electrospun fiber compositions are applicable for the co-delivery of drug agents for any number of indications that can benefit from the co-delivery of physicochemically diverse drug agents, but are particularly applicable for the co-delivery of antimicrobial and contraceptive drug agents to the vaginal mucosa to provide simultaneous protection from infection (e.g., fungal, bacterial and/or viral infection, including, but not limited to HIV) and unintended pregnancy.

Described herein are drug delivery compositions including at least two drug agents included in electrospun polymer fibers, wherein at least two of said agents have different physicochemical properties. In other embodiments, the electrospun polymer fibers include fibers that include said at least two drug agents in the same fiber. In other embodiments, the at least two drug agents in the same fiber are arranged in a uniaxial or coaxial configuration. In other embodiments, the electrospun polymer fibers include fibers having different drug agents in different fibers.

In other embodiments, the different fibers are arranged in a fabric including a stacked, interwoven or combined composite microarchitecture. In other embodiments, the fibers are degradable. In other embodiments, the at least two drug agents include a drug agent that is hydrophobic and a drug agent that is hydrophilic. In other embodiments, the electrospun fibers include a said drug agent present in a range of 0.01%-60% or more by weight. In other embodiments, the drug agents are released with differing kinetics upon contact of said composition with a hydrating fluid. In other embodiments, the at least two of the different drug agents are asynchronously released.

In other embodiments, at least one of said drug agents modifies the release characteristics of at least one other drug agent from said fibers. In other embodiments, the release characteristics are modified by the inclusion of an excipient in the solution from which fibers are electrospun.

In other embodiments, the release kinetics of a hydrophobic drug agent are not substantially influenced by the presence or amount of a hydrophilic drug agent in the composition.

In other embodiments, the at least one said drug agent is released with burst kinetics. In other embodiments, the at least one said drug agent has sustained release kinetics. In other embodiments, the which at least one drug agent is released with burst kinetics and at least one drug agent is released with sustained release kinetics. In other embodiments, the at least one drug agent is released with an initial burst, followed by sustained release of the same agent. In other embodiments, one subset or layer of fibers provides burst release kinetics, and another subset or layer of fibers provides sustained release kinetics.

In other embodiments, the at least one drug agent is less than 10% crystalline or amorphous particulate dispersion.

In other embodiments, the drug agents include an antimicrobial drug and a contraceptive agent.

In other embodiments, the antimicrobial drug includes an antiviral drug. In other embodiments, the antimicrobial drug includes an antiretroviral drug. In other embodiments, the antiviral drug includes a drug selected from the group including a viral entry inhibitor, a reverse-transcriptase inhibitor, and an integrase inhibitor. In other embodiments, the antiviral drug is selected from the group including miraviroc (MVC), cyanovirin-N (CV-N), tenofovir (TFV), dapivirine (DPV), etravirine (ETR), azidothymidine (AZT), acyclovir (ACV), raltegravir (RAL) and glycerol monolaurate (GML).

In other embodiments, the contraceptive agent includes a hormonal or non-hormonal contraceptive drug. In other embodiments, the contraceptive agent includes levonorgestrel. In other embodiments, the contraceptive agent includes progestogen, progestins such as drospirenone and desogestrel, other steroidal compounds such as mifepristone, ulipristal, or copper.

In other embodiments, the fibers further form a physical barrier to sperm penetration when contacted with the vagina.

In other embodiments, the polymer fibers include or are spun from a polymer selected from the group including poly (lactide-co-glycolide) (PLGA), polylactic acid (PLA), poly ε-caprolactone (PCL), polyvinyl alcohol (PVA), polyethylene oxide (PEO), polyvinylpyrrolidone (PVP), poly methacrylic acid (PMAA) and ethyl cellulose (EC). In other embodiments, the drug delivery composition is formulated for delivery to the vaginal mucosa.

Also described herein is a method of co-delivering at least two drug agents having different physicochemical properties to a mucosal tissue, the method including contacting said tissue with any one of the aforementioned compositions. In other embodiments, the mucosal tissue includes vaginal or rectal mucosal tissue.

Also describe herein is a method of simultaneous contraception and antimicrobial prophylaxis, the method including contacting a mucosal tissue of an individual in need thereof with any one of the aforementioned compositions. In other embodiments, the composition includes a contraceptive drug agent and an antimicrobial drug agent that is an antiviral agent. In other embodiments, the mucosal tissue includes vaginal or rectal mucosal tissue.

Further described herein is a method of making a drug delivery composition including electrospinning polymer fibers including at least two different drug agents having different physicochemical properties. In other embodiments, the electrospinning includes electrospinning fibers from a polymer solution including at least two different drug agents having different physicochemical properties. In other embodiments, the electrospinning includes simultaneously electrospinning fibers from different polymer solutions onto a single substrate, said different polymer solutions including different drug agents. In various embodiments, the fibers are degradable fibers. In other embodiments, electrospinning forms a fabric having an interwoven, stacked or combined composite microarchitecture. In the other embodiments, the method further includes stacking the product of one electrospinning around the product of a second electrospinning round to form a stacked microarchitecture, each said product including one or more drug agents.

DEFINITIONS

As used herein, the term "asynchronously released" refers to the release of two different drug agents from the fibers described herein at substantially different rates. More particularly, the term can refer to release of one drug agent from a drug delivery composition as described herein with burst kinetics, while a second drug agent is released from the same composition with sustained release kinetics as those terms are used herein. Alternatively, if the time required for the release of 50% of first and second drugs differs by 4 hours or more, 8 hours or more, 12 hours or more, 18 hours or more, 24 hours or more or greater, the drugs are asynchronously released.

As used herein, the term "different physicochemical properties" or "physicochemically diverse" refers to agents or drugs that fall into different categories with respect to one or more physicochemical properties. For example, two agents or drugs can have differing degrees of hydrophobicity/hydrophilicity (i.e., one is hydrophilic, and the other is hydrophobic), differing degrees of solubility (which are impacted by hydrophobicity/hydrophilicity; i.e., one is highly soluble, and the other is less soluble—generally, a difference in solubility refers to at least one order of magnitude difference in solubility), differing partition coefficient (LogP; e.g., one has a positive LogP, the other negative—generally, a difference in partition coefficients refers to at least one order of magnitude difference in partition coefficient), differing distribution coefficient (e.g., one is positive, one is negative—generally, a difference in distribution coefficients refers to at least one order of magnitude difference in distribution coefficient), electrical charge/ionization (i.e., one is positively charged, one negatively or uncharged, or similarly, one is negatively charged, the other positively or uncharged). Other relevant properties include, for example, polymeric versus monomeric form, solids suspension or particulate versus molecularly soluble, and substantially crystalline versus substantially amorphous. By "different" in this context is also meant that the two agents or drugs will differ by at least 50%, preferably by at least 1-fold, 2-fold, 5-fold or more with respect to the given property. In a preferred aspect, the physicochemical property is solubility in aqueous solution, and the difference is by a factor of 10-fold (i.e., an order of magnitude) or more. In general, agents that have a negative LogP are considered hydrophilic, and agents with a positive LogP are considered hydrophobic. As but one example, two agents, in which one has a negative LogP and the other has a positive LogP would be considered physicochemically diverse. However, consistent with the use of the term herein, two agents that have respective LogP values of −1 and −2 are also considered physicochemically diverse, as they differ in partition coefficient by at least an order of magnitude.

As used herein, the term "drug agents" refers to molecules, encompassing small molecule drugs, derivatives, analogs, and salts thereof, further including peptides, proteins, nucleic acids, carbohydrates, and other biologicals.

As used herein, the term "burst kinetics" refer to the release of at least 50% of drug agent within 30 minutes or less of contacting an electrospun fiber composition as described herein with a mucosal tissue. In various embodiments, burst release can include release of at least 75% within 30 minutes, or at least 80%, 85%, 90%, 95% or even all of the drug (100%) within 30 minutes. In other embodiments, these levels of release are achieved, for example after 20 minutes or less, 15 minutes or less, 10 minutes or less, or even 5 minutes or less.

As used herein, the term "prolonged release kinetics" or "sustained release kinetics" refers to drug release from an electrospun fiber over a period greater than 48 hours. That is, it takes greater than 48 hours to achieve 100% release. In various embodiments, sustained release can include, for example, release over 72 or 96 hours or more, including one week or more.

As used herein in reference to fibers, the term "degradable" refers to electrospun fibers that degrade when in contact with a mucosal tissue in vivo. Degradation can occur over a range of minutes, hours, days, weeks or even months, but to the extent that a fibrous material is degraded or bioabsorbed over time, it is "degradable." The term is in direct contrast with fibers that are "biodurable," i.e., fibers that do not substantially degrade when placed in contact with a mucosal tissue in vivo. Examples of biodurable fibers include polyethylene and polypropylene fibers. As used herein, the term "biocompatible" refers to materials that are tolerated by the body and its tissues upon administration by, e.g., implantation, ingestion, or contacting with a mucosal tissue. Biocompatible materials are substantially not toxic to cells or tissues in the form used, and do not provoke an inflammatory or immune response in the individual to whom they are administered.

BRIEF DESCRIPTION OF FIGURES

FIG. 4. Physical properties independent of drug incorporation. High drug incorporation was achieved across virtually all combinations of drug agents, as shown in encapsulation efficiency, with uniform productivity and consistent fiber diameter achieved across different combinations. Drug crystallinity was relatively was low or immeasurable in the produced fabrics. Drug loading is shown in parentheses (wt. dr/wt. fiber), encapsulation efficiency, fiber diameter, and drug crystallinity was measured using HPLC, SEM, and DSC, respectively.

FIG. 5. Confocal microscopy of fluorescent fabrics reveals co-localization of LNG and TFV in combined microarchitecture. Alexa Fluor staining demonstrate co-localization of various drug agents in the produced electrospun fabrics.

FIG. 24. Physical properties of fibers are consistent between needle rig and Nanospider. Electrospinning was successful for 0-60% TFV/PVA solutions and produced fibers with diameters ranging from 140-320 nm.

FIG. 27. Drug agent crystallinity. pH-adjusted PVA-TFV fibers containing 60% TFV have less than 2% crystalline drug, compared with 87-91% crystalline drug for unadjusted fibers.

FIG. 35 Properties of electrospun fibers. Top panel, Thermal behaviors for EC, EC-DPV, and DPV combinations were measured, demonstrating the release characteristics of DPV from Bottom panel, SEM images of DPV loaded in to electrospun EC fibers demonstrated structural integrity of the produced fibers.

FIG. 36 Compatibility of combination electrospun fibers. Top panel, measurements demonstrating the potential compatibility of PVP and EC fibers Bottom panel, DPV release characteristics when the materials are combined together.

FIG. 37 Morphology of combination materials. Top panel, profile of DPV release in combination materials and Bottom panel, morphology of PVP-EC mats after DPV release.

FIG. 39. Additional properties of combination materials. Top panel, thermal profiles of materials and Bottom panel, variable release behaviors.

DETAILED DESCRIPTION

Figure 1:
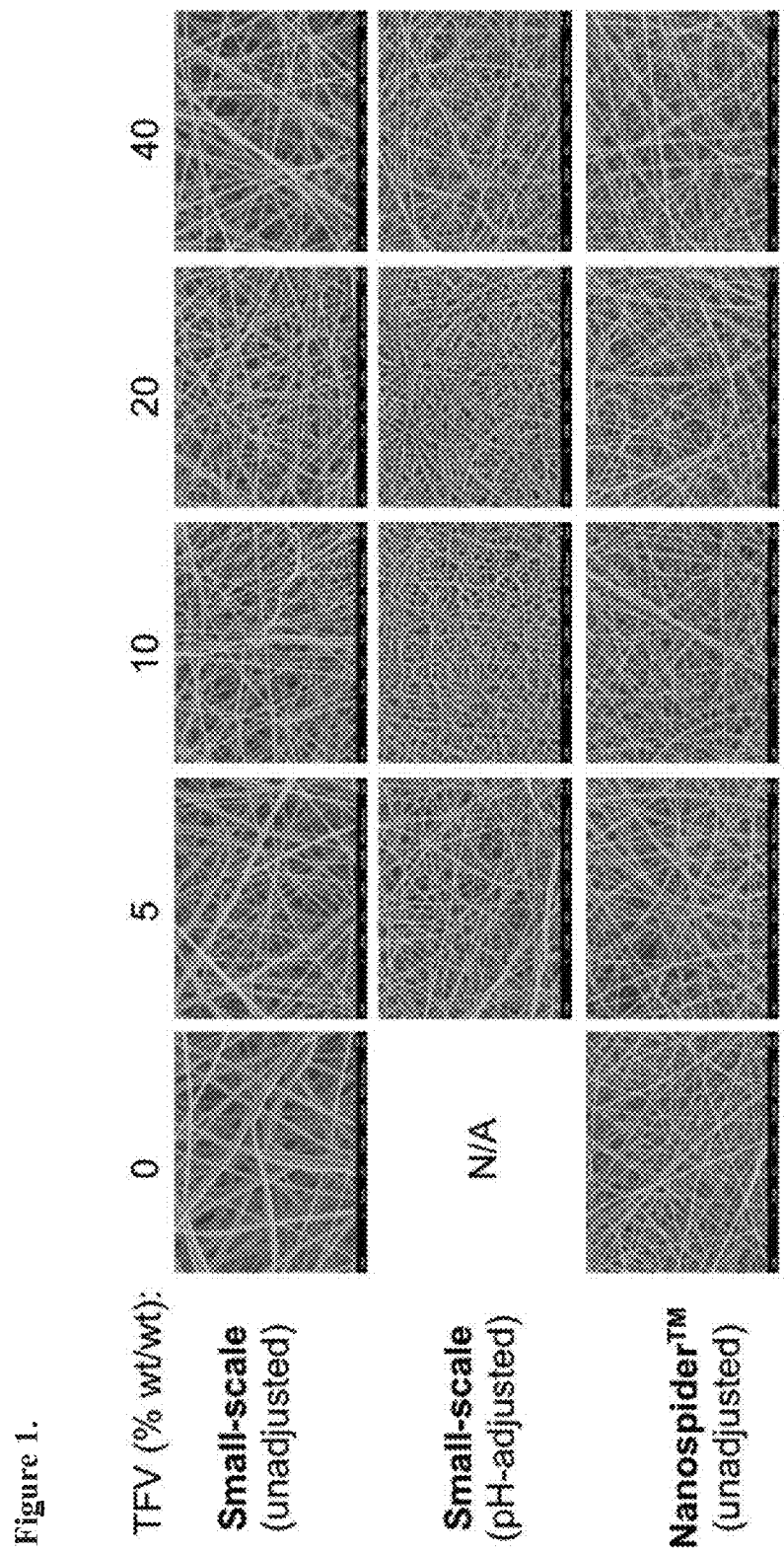
FIG. 1. Scanning electro micrograph ("SEM") images of tenofovir ("TFV")-containing polyvinyl alcohol ("PVA") fibers. Depicted are results from small-scale lab system and large-scale Nanospider™. As shown, consistent fibers were produced using small-scale, pH-adjusted small-scale, and larger scale instruments display proper fiber-like morphology.

Drug delivery systems ("DDS") play a principal role in bridging biological efficacy and behavioral adherence, which together govern the overall use and therefore, effective impact of drug agents.

Drug combinations have been shown to have several advantages compared to treatment with a single therapeutic agent, including potential synergistic effects, fewer occurrences of drug resistance, and enhanced efficacy. The importance of drug combinations can be seen in applications ranging from treatment of HIV/AIDS, neurodegenerative disease, cancer, and multi-drug resistant bacterial infections. However, combining multiple drugs into a single treatment requires careful optimization to enhance therapeutic effects beyond that of a singular drug. Co-delivery of certain drug combinations may require novel delivery vehicles capable of combining hydrophilic and hydrophobic drugs, actively targeting certain cell populations, and controlling the temporal release of both drugs independently. Developments in nanotechnology, such as particles and other delivery systems, present a new arena for overcoming these and other challenges associated with combination drug delivery.

Such multi-drug delivery approaches are clearly useful in a number of applications, including cancer therapeutics, antibiotic treatment, and multipurpose prevention of STIs and unintended pregnancy. Despite these potentially significant advances in drug delivery systems ("DDS"), little is actually known about how fiber microarchitecture and fabric thickness affect drug release and activity, particular for co-delivered drugs. Moreover, significant hurdles exist in the production of such fibers at clinically relevant scales.

Co-delivery is relevant to many topical delivery systems that target delivery of pharmaceutical agents either externally, such as to the skin or eye, or internally, such as to the mucous membranes of the mouth, vagina or rectum. Topical delivery is advantageous in that it avoids first pass metabolism, is convenient for and generally accepted by users, presents the opportunity for easily reversible treatment and may have smaller dosing requirements. Advances in topical delivery systems have yielded success with transdermal delivery of contraceptives, medical fabrics loaded with antibiotics for more effective wound healing, and buccal delivery of, e.g., an anti-Alzheimer's drug. Various delivery vehicles have expanded the potential to deliver more diverse drugs in a variety of applications. For example, dissolving microneedles of polysaccharides have been developed allowing for precisely tuned delivery of both small molecules and biologics transdermally. Others have developed mucosal-penetrating nanoparticles for the delivery of antiretrovirals to the vagina as HIV pre-exposure prophylaxis. The expansion of deliverable drugs via topical delivery is permitted by the development of novel delivery systems that overcome the challenges associated with topical delivery, such as drug limitations based on solubility, particle size, molecular weight and polymorphism. However, delivery of drug combinations using topical systems has been largely unexplored due to challenges associated with co-delivery, including delivery of physicochemically diverse drugs and difficulty in controlling independent release rates.

In this regard, drug-eluting fibers fabricated by electrospinning, which applies electrostatic forces for formation of micro- or nanoscale polymer fibers fabricated into fabrics of varying geometries, finds highly adaptable uses for biomedical applications ranging from drug delivery to tissue engineering scaffolds. A key aspect of this technique exploits the interplay between a polymer formulation's viscosity, surface tension, and conductivity in an electric field. Polymer nanofibers synthesized by electrospinning have consistent diameters and morphology, which are controlled by modulating the solution and process parameters, such as concentration and electric field strength.

Given this backdrop of parameters, it is noted that not all biocompatible polymers can be electrospun, as many biocompatible polymers do not match the viscosity, conductivity, or surface tension required in the process. Nevertheless, electrospun fibers are essentially a solid dosage form, providing enhanced versatility in terms of incorporating a diversity of polymers and drug agents. Such further advantages are apparent considering their flexible mechanical properties, as highly adaptable and comparatively easy use in organs such as the vagina, other orifices, or inner organ spaces. Additionally, their unique chemical properties also allow adjustment and modulation of a drug agent release profile.

While electrospun fibers appear to be an ideal topical delivery system for co-delivery of multiple drugs agents, electrospun fibers have not yet been designed as a vehicle for simultaneous co-delivery of a combination of physicochemically diverse drugs. Additionally, significant hurdles have existed in the production of electrospun fibers at clinically relevant scales.

As described, electrospun fibers are highly suited for delivery of drug agents, such as anti-HIV agents, as single drugs or drug combinations, with notable advantages in both efficacy (drug delivery) and user adherence (sensory perceptions and preferences). As electrospinnable polymers can span a range of hydrophilicity, crystallinity, and hydrolyzability, the drug release profile from electrospun fibers can be adjusted by controlling the physical properties of polymers or composites for each drug. Further, biomedical excipients can be added to adjust the overall "feel" of the materials, which is typically soft, highly flexible, non-abrasive, and devoid of sharp corners. In various applications, electrospun materials can be processed into sheets, tubes, pessaries, or coatings without altering the microscopic structure, formulation, or release properties of the materials. Such properties allow electrospun fibers to be applied in sensitive areas for delivery, such as the vagina, other orifices, or inner organ spaces.

As proof of principle for the co-delivery of diverse drug agents from electrospun fibers designed to release the agents with desired kinetics to, e.g., a mucosal tissue, described herein is the successful application of polyvinyl alcohol ("PVA") fibers incorporating tenofovir ("TFV"), a hydrophilic nucleotide reverse transcriptase inhibitor and lead compound for topical HIV-1 chemoprophylaxis, and levonorgestrel ("LNG"), a hydrophobic contraceptive drug agent, for the co-delivery of these agents, e.g., to the vaginal mucosa. It is anticipated that the parameters manipulated to permit the co-delivery of these representative hydrophilic and hydrophobic drug agents can be similarly manipulated to achieve co-delivery of other similarly diverse drug agents. Additional examples of different polymers and drug agent combinations are also provided herein.

Importantly, the apparatuses and methods described herein are also shown to be capable of scale-up for mass production, and PVA containing up to 0-40% (wt/wt) TFV can be successfully electrospun into fibers using both a laboratory-scale electrospinning system and manufacturing-scale needle-free system, the latter delivering at least a 1000-fold production increase. Further improvements were provided in increased TFV loading into fibers by increasing weight percent TFV in solution and, such results could also be enhanced by raising solution pH. In addition, it was discovered that fiber recovery increased with increasing solution conductivity for both small and large-scale systems. Importantly, novel composite fiber systems developed using these techniques allowed for generation of electrospun fibers capable of combined delivery of TFV, used for prevention of HIV, and levonorgestrel ("LNG") used for unintended pregnancy. Ordinarily, the significantly different physicochemical properties of these two drugs would preclude their combination in existing dosage forms. Described herein, it is shown that assembling different micro-scale geometries that are macroscopically indistinguishable, allow for molecularly unique medical fabrics for co-delivery of hydrophilic TFV and hydrophobic LNG.

As noted and as described further herein below, the inventors have discovered that certain parameters, such as pH can be adjusted to increase TFV solubility and actual TFV loading into fibers, maintaining solution electrospinnability. Drug crystallinity of pH-unadjusted versus pH-adjusted fibers can also be manipulated to adjust dissolution time and release kinetics. The inventors further demonstrate that co-delivery drug release of TFV, a hydrophilic antiretroviral, is slower when loaded directly into the same fiber as levonorgestrel LNG, a hydrophobic contraceptive, as compared to separate fibers and as fabric thickness increases. Importantly, the inventors discovered microarchitectures constructed when using a production-scale instrument, including stacked, interwoven and combined architectures, only combined fibers altered release profiles compared to single drug-loaded fibers. These results demonstrate that microarchitecture and fabric thickness are useful tools to control release of drugs from electrospun fiber fabrics, including fibers incorporating drug agents such as microbicidal for multipurpose prevention or treatment.

In vitro studies described herein demonstrate that antiviral activity of TFV against HIV-BaL infection in TZM-bl cells is similar to the unformulated drug, and is not affected by the architecture of the composite fabrics.

The particular composition and organization of the electrospun fibers as described herein permit effective co-delivery of multiple drugs. Challenges associated with co-delivery, including delivery of hydrophilic and hydrophobic drugs from the same system, and independent, temporal control of drug release are addressed by manipulating the microarchitecture of the fiber compositions as described herein. This application relates, and claims priority to U.S. provisional patent application No. 61/723,024, filed Nov. 6, 2012, which is herein fully incorporated by reference.

Described herein is drug delivery composition including at least two drug agents included in electrospun polymer fibers, wherein at least two of said agents have different physicochemical properties. In various embodiments, at least two drug agents includes two, three, four, five, six, seven eight, nine, or ten or more drug agents. In other embodiments, the electrospun polymer fibers include fibers that include said at least two drug agents in the same fiber. In other embodiments, the at least two drug agents in the same fiber are arranged in a uniaxial or coaxial configuration. For example, a coaxial configuration can include a drug on the inside fiber as the core to delay drug release, particularly for hydrophilic agents.

In other embodiments, the electrospun polymer fibers include fibers having different drug agents in different fibers. In other embodiments, the different fibers are arranged in a fabric including a stacked, interwoven or combined composite microarchitecture. In other embodiments, the fibers are degradable.

The drug delivery systems described are well suited for delivery of drug agents with different physicochemical properties. In particular embodiments, the at least two drug agents include a drug agent that is hydrophobic and a drug agent that is hydrophilic. Drug agents with aqueous solubility over a range of, for example, $10^{-5}$ to $10^3$ g/L can be formulated in fibers as described herein. In particular embodiments, the aqueous solubilities for the different drug agents can vary by an order of magnitude or more. Other physicochemical properties that can differ include, for example, partition coefficient (varying over a range of −4 to 4; where partition coefficient is measured on a log scale, a difference of one point represents an order of magnitude—two drugs differing in partition coefficient by at least one point have different physoicochemical properties) or physical state (e.g., solid, crystalline solid, particulate solid, dispersion solid, semi-solid, liquid, molecularly soluble, etc.).

In various embodiments, one of the at least two drug agents has an aqueous solubility of $10^{-5}$, $10^{-4}$, $10^{-3}$, $10^{-2}$, $10^{-1}$, 1, $10^1$, $10^2$, or $10^3$, or any value there between, and the other has solubility varying by at least an order of magnitude from the first. In various embodiments, one of the at least two drug agents has a partition coefficient of −4, −3, −1, 1, 2, 3 or 4 or any value there between, and the other has a partition coefficient varying by at least an order of magnitude from the first. In various embodiments, one of the at least two drug agents is in the form of a solid, crystalline solid, particulate solid, dispersion solid, semi-solid, liquid, or a molecularly soluble drug agent and the other in a state selected from any other of these states.

In various embodiments, the electrospun fibers include a said drug agent present in a range of 0.01%-60% or more by weight. In various embodiments, the drug agent is present in a range of 0.01-1%, 1-5%, 5-10%, 10-25%, 25-40% by weight. In various embodiments, the drug agent is present in a range of 40%, 50%, 60%, 70% or more by weight. As readily understood by one of ordinary skill, increased polymer concentration will decrease drug loading as drug agent present in a % by weight of the composition. The converse is also true. In all embodiments, the % by weight of the electrospun polymer is present in a quantity sufficient to allow electrospinning.

In various embodiments, the electrospun fibers are fibers of about 60 to 80 nm in diameter, 80 to 100 nm, 100 to 120 nm, 120 to 140 nm, 140 to 160 nm, 160 to 180 nm, 180 to 200 nm, or 200 or more nm. In other embodiments, the drug agents are released with differing kinetics upon contact of said composition with a hydrating fluid. For example, the hydrating fluid can be at the surface of a mucosal tissue. In other embodiments, the at least two of the different drug agents are asynchronously released. In other embodiments, at least one of said drug agents modifies the release characteristics of at least one other drug agent from said fibers.

In other embodiments, the electrospun fibers have a viscosity of about 0.5-4 Pa·s. In various embodiments, the electrospun fibers have a viscosity of about 0.5-1, 1-2, 2-3, or 3-4 Pa·s. In certain embodiments, the electrospun fibers have a viscosity of less than 0.5 Pa·s. In certain embodiments, the electrospun fibers have a viscosity of more than 0.5 Pa·s.

In other embodiments, the electrospun fibers have a conductivity of about 0.9-17,500 µS/cm. In various embodiments, the electrospun fibers have a conductivity of about 0.9-1000, 1000-2000, 2000-3000, 3000-4000, 4000-5000, 5000-6000, 6000-7000, 7000-8000, 8000-9000, 9000-10,000, 10-11,000, 11-12,000, 12-13,000, 13-14,000, 14-15,000, 15-16,000, 16-17,000 or 17-17,500 µS/cm. In certain embodiments, the electrospun fibers have a conductivity of less than 0.90 µS/cm. In certain embodiments, the electrospun fibers have a conductivity of more than 17,500 µS/cm.

In other embodiments, the electrospun fibers have a surface tension of 26-73 mN/m. In other embodiments, the electrospun fibers have a surface tension of about 26-30 mN/m, 30-35, 35-40, 45-50, 55-60, 60-65, 65-70, 70-23 mN/m. In other embodiments, the electrospun fibers have a surface tension of less than 26 mN/m. In other embodiments, the electrospun fibers have a surface tension of more than 26 mN/m.

In various embodiments, the electrospun fibers have a viscosity of about 0.5-4 Pa·s, conductivity of about 0.9-17,500, and a surface tension of 26-73 mN/m, and combinations thereof.

In other embodiments, the release characteristics are modified by the inclusion of an excipient in the solution from which fibers are electrospun. In other embodiments, the release kinetics of a hydrophobic drug agent are not substantially influenced by the presence or amount of a hydrophilic drug agent in the composition. In other embodiments, the at least one said drug agent is released with burst kinetics. In various embodiments, the burst kinetics result in 50, 60, 70, 80, 90 or more % release from the fibers after about 30 minutes or less. In various embodiments, the burst kinetics result in 50, 60, 70, 80, 90 or more % release from the fibers after about 30, 45, 60, 90, 120, or 120 minutes or less.

In other embodiments, at least one said drug agent has sustained release kinetics. In other embodiments, at least one drug agent is released with burst kinetics and at least one drug agent is released with sustained release kinetics. In other embodiments, at least one drug agent is released with an initial burst, followed by sustained release of the same agent.

In other embodiments, one subset or layer of fibers provides burst release kinetics, and another subset or layer of fibers provides prolonged release kinetics. In other embodiments, the at least one drug agent is less than 10% crystalline or amorphous particulate dispersion. In other embodiments, the at least one drug agent is less than 5% crystalline or amorphous particulate dispersion. In other embodiments, the at least one drug agent is less than 2% crystalline or amorphous particulate dispersion. In other embodiments, the at least one drug agent is less than 1% crystalline or amorphous particulate dispersion. Higher proportions of crystalline or amorphous particulate drug agent are specifically contemplated—in general, the more particulate or crystalline agent present, the slower the release kinetics relative to molecularly soluble forms.

For example, the described methods can be applied to achieve slow hydrophobic drug release by incorporating the hydrophobic compound in a hydrophobic matrix fiber. In other embodiments, the elecstropun polymer can be modified by altering crystallinity via freeze/thaw cycles, crosslinking, or increasing thickness. Alternatively, faster hydrophobic drug release could be achieved through the incorporation of excipients to enhance polymer swelling (e.g., salts, polyethylene glycol) or dissolution (e.g., sodium starch glycolate), or drug solubility (e.g., detergents). In addition, described methods can be applied to achieve slow hydrophilic agent release, by for example, using a rate controlling shell membrane via coaxial electrospinning, using excipients to decrease drug solubility in hydrated polymer boundary, increasing fabric thickness, or altering polymer selection (hydrophobicity, crystallinity). Various excipients can included in dosage form to aid manufacture, administration or absorption. For example, polyethylene glycol ("PEG") is a biologically inert, non-immunogenic chemical that confers greater water solubility to proteins commonly available commercially as mixtures of different oligomer sizes in broadly or narrowly defined molecular weight ("MW") ranges, such as "PEG 600" having an average MW of 600, "PEG 10000" denotes a mixture of PEG molecules having an average MW of 10,000 g/mol, with attachment to proteins and other biomolecules decreases aggregation and increases solubility. Sodium starch glycolate is the sodium salt of a carboxymethyl ether of starch, carboxymethylation process increases the ability of the starch to absorb water, making it a rapid distintegrant. Similarly, detergents, such as noncharged detergents are used as excipients in drug formulations, as inert compounds to enhance drug absorption essentially by improving drug solubility.

In various embodiments, the drug agents include an antimicrobial drug and a contraceptive agent. In other embodiments, the antimicrobial drug includes an antiviral drug. In other embodiments, the antimicrobial drug includes an antiretroviral drug. In other embodiments, the antiviral drug includes a drug selected from the group including a viral entry inhibitor, a reverse-transcriptase inhibitor, and an integrase inhibitor. In other embodiments, the antiviral drug is selected from the group including miraviroc (MVC), cyanovirin-N (CV-N), tenofovir (TFV), dapivirine (DPV), etravirine (ETR), azidothymidine (AZT), acyclovir (ACV), raltegravir (RAL) and glycerol monolaurate (GML). As understood to one of ordinary skill, the described antivirals can be sub-classified as entry inhibitors (e.g. MVC, CV-N), reverse transcriptase inhibitors (TFV, DPV, ETR, AZT, ACV), integrase inhibitors (RAL), and immunomodulatory agents (GML). In other embodiments, the contraceptive agent includes a hormonal or non-hormonal contraceptive drug. In other embodiments, the contraceptive agent includes levonorgestrel. In other embodiments, the contraceptive agent includes progestogen, progestins such as drospirenone and desogestrel, other steroidal compounds such as mifepristone, ulipristal, or copper. In other embodiments, the fibers further form a physical barrier to sperm penetration when contacted with the vagina. In various embodiments, the drug agents include an antimicrobial drug and a contraceptive agent that is a combination of any of the aforementioned drugs, such as combinations of antiretroviral drugs miraviroc (MVC), cyanovirin-N (CV-N), tenofovir (TFV), dapivirine (DPV), etravirine (ETR), azidothymidine (AZT), acyclovir (ACV), raltegravir (RAL) glycerol monolaurate (GML), and contraceptive agents levonorgestrel, progestogen, progestins such as drospirenone and desogestrel, other steroidal compounds such as mifepristone, ulipristal, and/or copper.

In other embodiments, the polymer fibers include or are spun from a polymer selected from the group including poly (lactide-co-glycolide) (PLGA), polylactic acid (PLA), poly ε-caprolactone (PCL), polyvinyl alcohol (PVA), polyethylene oxide (PEO), polyvinylpyrrolidone (PVP), poly methacrylic acid (PMAA) and ethyl cellulose (EC). As understood to one of ordinary skill, each of the described compounds can be described as biodegradable polymers (e.g., PLGA, PLA, PCL), synthetic bioeliminable (e.g. PVA, PEO, PVP), synthetic non-biodegradable (e.g. PMAA, ethylcellulose) and natural polymers. In other embodiments, the drug delivery composition is formulated for delivery to the vaginal mucosa. In various embodiments, the drug delivery composition can be used alone or in combination with existing vaginal dosages forms (e.g., as coatings on devices).

In various embodiments, the drug delivery compositions include a range of different polymer and drug combinations for electrospinning as summarized in Supplementary Table 5.

Also described herein is a method of co-delivering at least two drug agents having different physicochemical properties to a mucosal tissue, the method including contacting said tissue with any one of the aforementioned compositions. In other embodiments, the mucosal tissue includes vaginal or rectal mucosal tissue.

Also described herein is a method of simultaneous contraception and antimicrobial prophylaxis, the method including contacting a mucosal tissue of an individual in need thereof with any one of the aforementioned compositions. In other embodiments, the composition includes a contraceptive drug agent and an antimicrobial drug agent that is an antiviral agent. In other embodiments, the mucosal tissue includes vaginal or rectal mucosal tissue.

Further described herein is a method of making a drug delivery composition including electrospinning polymer fibers including at least two different drug agents having different physicochemical properties. In other embodiments, the electrospinning includes electrospinning fibers from a polymer solution including at least two different drug agents having different physicochemical properties. In other embodiments, the electrospinning includes simultaneously electrospinning fibers from different polymer solutions onto a single substrate, said different polymer solutions including different drug agents. In various embodiments, the fibers are degradable fibers. In other embodiments, electrospinning forms a fabric having an interwoven, stacked or combined composite microarchitecture. In the other embodiments, the method further includes stacking the product of one electrospinning around the product of a second electrospinning round to form a stacked microarchitecture, each said product including one or more drug agents. For example, in various embodiments, one can optionally stack spun layers in sequential fashion or manually layer the spun layers after completion of spinning.

Polymers:

A variety of different polymers can be used as the base solution for the preparation of electrospun fibers as described herein. Polyvinyl alcohol is used in the examples below, and is well suited for drug delivery because it is recognized as biocompatible. However, it should be understood that a other polymer compositions can also be employed for electrospun fibers as described herein. Depending upon the drug agents employed, it may be advantageous to use a hydrophilic polymer. Examples include, but are not limited to polyethylene glycol (PEG), polypropylene glycol, PVA, polyethylene oxide, polypyrolidone or polyvinylpyrrolidone (PVP), and the biodegradable PolyActive™, a soft ethylene glycol-terephthalate block copolymer with a hard polybutylene terephthalate manufactured by OctoPlus Zernickedreef Holland. Depending upon the drug agents employed, it may be advantageous to use a hydrophobic polymer. Examples include, but are not limited to polycarbothane, the hydrophobic polymers Shore A 75™-Shore D 72™ manufactured by Thermedics Polymer Products, Wilmington, Mass., polyvinyl acetate, ethyl cellulose, polysulfone, polyvinyl chloride, polyurethane, and polylactide or polylactic acid.

Drug Agents:

Any of a number of drug agents can be formulated for delivery using the fiber compositions described herein. In particular, as described herein, physicochemically diverse drug agents can be co-formulated to provide co-delivery from a single composition. Drug agents can include, but are not limited to, compounds that may be classified as medicines, organic and inorganic drugs, hormones, nutrients, vitamins, food supplements, herbal preparations, and other agents that might benefit a human or animal. In general, such classifications include, but are not limited to, ACE inhibitors, adrenergics and anti-adrenergics, alcohol deterrents (for example, disulfuram), anti-allergies, anti-anginals, anti-arthritics, anti-infectives (including but not limited to antibacterials, antibiotics, antifungals, antihelmintics, antimalarials and antiviral agents), analgesics and analgesic combinations, local and systemic anesthetics, appetite suppressants, antioxidants, anxiolytics, anorexics, antiarthritics, anti-asthmatic agents, anticoagulants, anticonvulsants, antidiabetic agents, antidiarrheals, anti-emetics, anti-epileptics, antihistamines, anti-inflammatory agents, antihypertensives, antimigraines, antinauseants, antineoplastics, antioxidants, antiparkinsonism drugs, antipruritics, antipyretics, antirheumatics, antispasmodics, antitussives, adrenergic receptor agonists and antagonists, anorexics, appetite suppressants, breath freshening agents (including but not limited to peppermint oil, spearmint oil, wintergreen oil and menthol), cardiovascular preparations (including anti-arrhythmic agents, cardiotonics, cardiac depressants, calcium channel blockers and beta blockers), cholinergics and anticholinergics, contraceptives, cough and cold preparations, diuretics, decongestants, growth stimulants, herbal preparations, hormones including but not limited to androgens, estrogens and progestins, steroids and corticosteroids, hypnotics, immunizing agents, immunomodulators, immunosuppresives, muscle relaxants, neurologically-active agents including anti-anxiety preparations, antidepressants, antipsychotics, psychostimulants, sedatives and tranquilizers, sore throat medicaments, sympathomimetics, vaccines, vasodilators, vasoconstrictors, vitamins, xanthine derivatives and combinations thereof.

Additional representative active agents include, by way of example and not for purposes of limitation, bepridil, diltiazen, felodipine, isradipine, nicardipine, nifedipine, nimodipine, nitredipine, verapamil, dobutamine, isoproterenol, carterolol, labetalol, levobunolol nadolol, penbutolol, pindolol, propranolol, solatol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6a-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, isobutamben, lidocaine, mepivacaine, pramoxine, prilocalne, procaine, proparacaine, tetracaine, zolamine hydrochloride, alfentanil, chloroform, clonidine, cyclopropane, desflurane, diethyl ether, droperidol, enflurane, etomidate, fentanyl, halothane, isoflurane, ketamine hydrochloride, mepridine, methohexital, methoxyflurane, morphine, propofol, sevoflurane, sufentanil, thiamylal, thiopental, acetominophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, mesalamine, methyl salicylate, nabumetone, naproxen, oxyphenbutazone, phenacetin, phenylbutazone, piroxican, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, diisopyramide, encamide, flecamide, indecanide, mexiletine, moricizine, phenyloin, procainamide, propafenone, quinidine, tocamide, cisapride, domperidone, dronabinol, haloperidol, metoclopramide, nabilone, prochlorperazine, promethazine, thiethylperazine, trimethobenzamide, buprenorphine, butorphanol, codeine, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, oxycodone, oxymorphone, pentazocine, propoxyphene, isosorbide dinditrate, nitroglycerin, theophylline, phenylephrine, ephidrine, pilocarpine, furosemide, tetracycline, chlorpheniramine, ketorolac, ketorolac tromethamine, bromocriptine, guanabenz, prazosin, doxazosin, flufenamic acid, benzonatate, dextromethorphan hydrobromide, noscapine, codeine phosphate, scopolamine, minoxidil, combinations of the above-identified active agents, and pharmaceutically acceptable salts thereof.

Other representative agents include, but are not limited to, benzodiazepines, such as alprazolan, brotizolam, chlordiazepoxide, clobazam, clonazepam, clorazepate, demoxepam, diazepam, flumazenil, flurazepan, halazepan, lorazepan, midazolam, nitrazepan, nordazepan, oxazepan, prazepam, quazepan, temazepan, triazolan, pharmaceutically acceptable salts thereof, and combinations thereof anticholinergic agents such as anisotropine, atropine, belladonna, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, telezepine, tridihexethyl, tropicamide, combinations thereof, and pharmaceutically acceptable salts thereof estrogens, including but not limited to, 17p-estradiol (or estradiol), 17a-estradiol, chlorotrianisene, methyl estradiol, estriol, equilin, estrone, estropipate, fenestrel, mestranol, quinestrol, estrogen esters (including but not limited to estradiol cypionate, estradiol enanthate, estradiol valerate, estradiol-3-benzoate, estradiol undecylate, and estradiol 16,17-hemisuccinate), ethinyl estradiol, ethinyl estradiol-3-isopropylsulphonate, pharmaceutically acceptable salts thereof, and combinations thereof androgens such as danazol, fluoxymesterone, methandrostenolone, methyltestosterone, nandrolone, nandrolone decanoate, nandrolone phenproprionate, oxandrolone, oxymetholone, stanozolol, testolactone, testosterone, testosterone cypionate, testosterone enanthate, testosterone propionate, 19-nortestosterone, pharmaceutically acceptable salts thereof, and combinations thereof and progestins such as cingestol, ethynodiol diacetate, gestaclone, gestodene, hydroxyprogesterone caproate, levonorgestrel, medroxyprogesterone acetate, megestrol acetate, norgestimate, 17-deacetyl norgestimate, norethindrone, norethindrone acetate, norethynodrel, norgestrel, desogestrel, progesterone, quingestrone, tigestol, pharmaceutically acceptable salts thereof, and combinations thereof.

It is specifically contemplated that any of the aforementioned drug agents may be combined together as incorporated into an electrospun fiber, or combination of electrospun fibers, such as electrospun fibers containing at least two drug agents included in electrospun polymer fibers, wherein at least two of the drug agents have different physicochemical properties, or at least two drug agents includes two, three, four, five, six, seven eight, nine, or ten or more drug agents.

Dosage and Efficacy: As drug agents in the present invention are provided to a subject as incorporated in electrospun fibers, delivered via electrospun fibers, dosages of the drug agent of interest can be described as a % weight of the drug agent/quantity of fiber. For example, dosages can include 0.01%-60% or more by weight. Various exemplary drug dosage ranges can include 0.01-1%, 1-5%, 5-10%, 10-25%, 25-40% by weight. In various embodiments, the drug agent is present in a range of 40%, 50%, 60%, 70% or more by weight. Alternatively, the amount of drug agent delivered can be expressed as the mass of the drug agent quantity, for example, drug agents can be provided in less than 1, 1-10, 10-20, 20-30, 30-40, 40-50, 50 or more mg quantities, delivered hourly, daily or in any other scheduled fashion. Furthermore, drug agents can be provided in 50 or more, 100, 200, 300, 400, 500, 600, 700, 800, 900, 1000 or more mg, delivered hourly, daily or in any other scheduled fashion. In other applications, drug agent dosages are provided in a therapeutically effective dosage quantity.

Determining a therapeutically effective dosage quantity is readily ascertained by any one of many techniques known to one of ordinary skill in the art. For example, as related to contraception, a therapeutically effective quantity may be measured by measuring the amount of spermiostasis, alternatively a transwell migration assay provides an alternative means for establishing an effective dosage for contraception as related to sperm migration. In another example, establishing a therapeutically effective quantity as related to viral infection can measured by measured by any of several relevant in vitro assays. For example, antiviral compounds MVC, AZT, and fibers can be evaluated for toxicity to TZM-bL cells. Alternatively, a therapeutically effective dosage quantity can be measured by the ability of the drug-loaded fibers themselves to inhibit HIV-1 BaL infection in TZM-bL cells.

EXAMPLES

Example 1

Co-Delivery of Physicochemically Diverse Drugs

Generally, a bottleneck in the development of DDS, such as topical anti-HIV microbicides delivered in the vagina, is the need to integrate multiple design criteria into a single product. This includes a relative paucity of materials and fabrication process for delivery of drugs in physically constrained spaces, such as the vagina, other orifices, or inner organ spaces due limitations on size, geometry, and mechanical properties, in addition to the properties of the drug pharmacological agents that can be packaged for delivery. Existing topical drug agents, such as microbicides, can be adapted for use with electrospun fibers for novel topical fiber-based dosage forms.

Electrospinning is a powerful method to produce near 100% drug encapsulation of composite materials produced by simultaneous spinning of multiple solutions and/or layering of multiple types of electrospun fibers. Fiber-based topical DDS, including anti-retroviral ("ARV") drug-eluting fibers constitute an entirely new dosage form, and exhibit unique materials and processing features that distinguish them from existing topical delivery products. Described herein are novel techniques for applying drug-eluting fibers for multipurpose prevention, wherein electrospun fibers represent a platform for expanding options for delivering physico-chemically diverse drug combinations. Some examples include maraviroc, azidothymidine, acyclovir, tenofovir, dapivirine, raltegravir, etravirine and the hormonal contraceptive, levonorgestrel.

In different embodiments, electrospun fibers can provide a platform for modulating drug release, such as that used for both pericoital and sustained protection by deploying rapidly dissolving fibers that quickly establish supersaturated concentrations of drugs within the vaginal cavity that drive rapid drug transport into tissue. Simultaneously, persistent fibers designed to sustain drug release over multiple days can be developed without imposing the macroscopic geometry, such as that of a solid ring or implant. As such, electrospun fibers also allow for specific designs towards user-preferences, as low user adherence is a critical obstacle for development of effective therapies, such as that of HIV microbicides due to poor user perceptions and limited capacity to rationally design products with enhanced user feasibility and acceptability.

Example 2

Electrospinning Parameters for PVA Solutions

The Inventors established a variety of electrospinning parameters for PVA solutions containing 0, 5, 10, 20, or 40% (wt/wt) TFV. Drug precipitate is observed in all pH-unadjusted TFV solutions. Given that TFV has a pKa ~4, it is likely that by increasing the pH, one can increase drug solubility in the polymer solutions. The pH of each of the TFV-containing solutions can be adjusted from pH ~3.3 to a final pH of 7.2-7.5 using 1 or 10 M NaOH, and solution conductivity is measured using a conductivity probe.

A small-scale set up consisting of a 30 kV voltage generator, syringe pump, and flat metal block as a grounded collector was applied. Variable parameters that were applied including adjustable flow rate (10-100 μL/min), voltage (15-20 kV), and distance to collector (9-21 cm). Observations of the formation of fiber meshes on the collector, the presence of a Taylor cone, and dripping solution are recorded for each set of parameters. A single fiber mesh from 500 μL of polymer solution can be electrospun for each pH-unadjusted and pH-adjusted solution using the optimal spinning parameters (i.e., the fastest flow rate possible for which no dripping was observed).

Based on the interest in comparing the properties of fibers spun using a large-scale instrument and with a small-scale laboratory system, one can also electrospin these solutions into nanofiber meshes using a Nanospider™ large-scale manufacturing instrument (Elmarco). The Nanospider™ is a needle-free system employing a free liquid surface electrospinning process in which a high voltage is applied across a rotating metal drum submerged in a bath of polymer solution. Multiple electrospinning jets spontaneously emerge from the solution and are collected in large sheets of fibers. Using such an apparatus, one can scale up production by 1000-fold, spinning fiber meshes from 500 mL of solution for each of the five TFV solutions. Fiber diameter and morphology for each mesh is characterized using scanning electron microscopy ("SEM") and ImageJ. Material efficiency is characterized by massing the amount of fibers recovered. In such instances, actual drug loading is evaluated by dissolving ~6 mg pieces of electrospun mesh in 20 mL of deionized water. Drug content is measured for triplicate mesh samples using high performance liquid chromatography.

Figure 25:
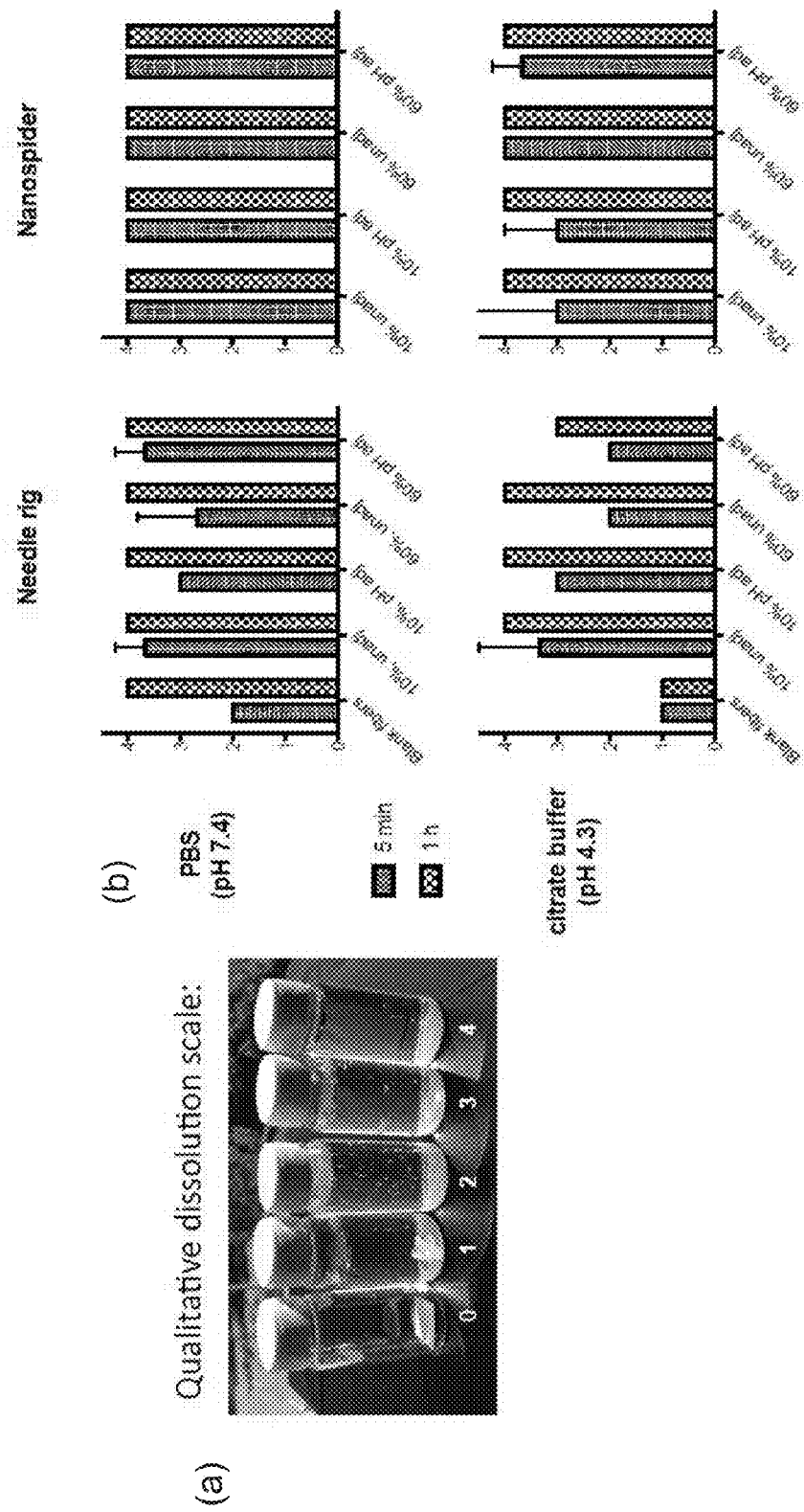
FIG. 25. TFV promotes fiber dissolution relative to blank fibers at pH 7.4 and 4.3. (a) Qualitative scale defining increasing states of dissolution, with 0=not wet out, fiber mesh intact 1=wet out; 2=broken into large pieces; 3=broken into small pieces (less than a pinhead in size); 4=fully dissolved (no mesh visible to naked eye). (b) Dissolution of fibers created using needle rig vs. Nanospider at 5 min and 1 hr, graphed as qualitative dissolution rating versus TFV content. Dissolution was measured at pH 7.4 and 4.3.
Figure 26:
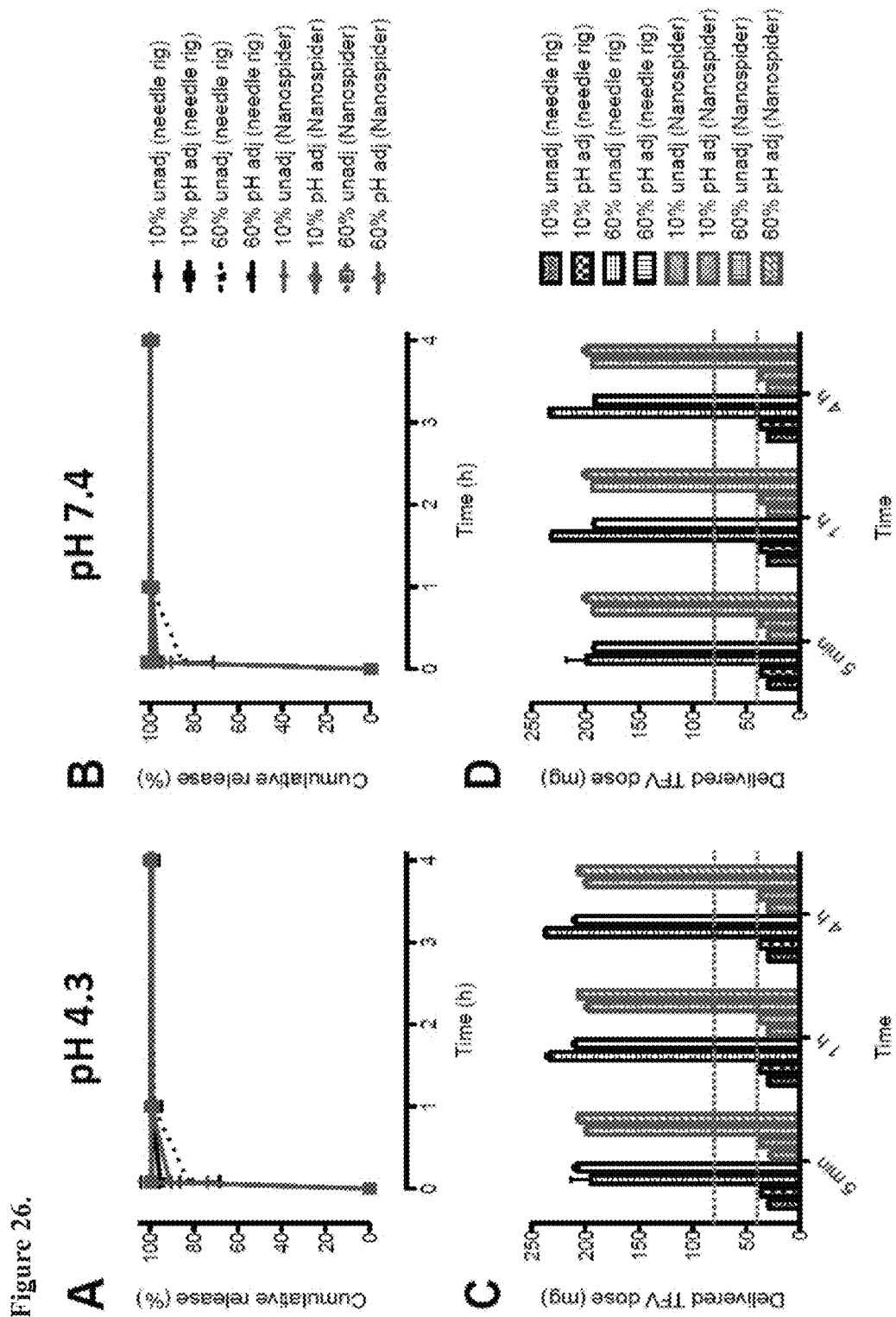
FIG. 26. Burst release of TFV within 5 minutes at pH 4.3 and 7.4 is similar for meshes electrospun on small scale and large scales. Graphs display cumulative release of TFV in pH 4.3 citrate buffer (a,c) or pH 7.4 PBS (b,d) for fibers spun on small scale versus large scale instruments for pH adjusted and unadjusted solutions. In (c) and (d), the y axis shows delivered dose TFV per 400 mg fiber mesh, with red lines indicating the recommended range for daily vaginal application (40-80 mg).
Figure 28:
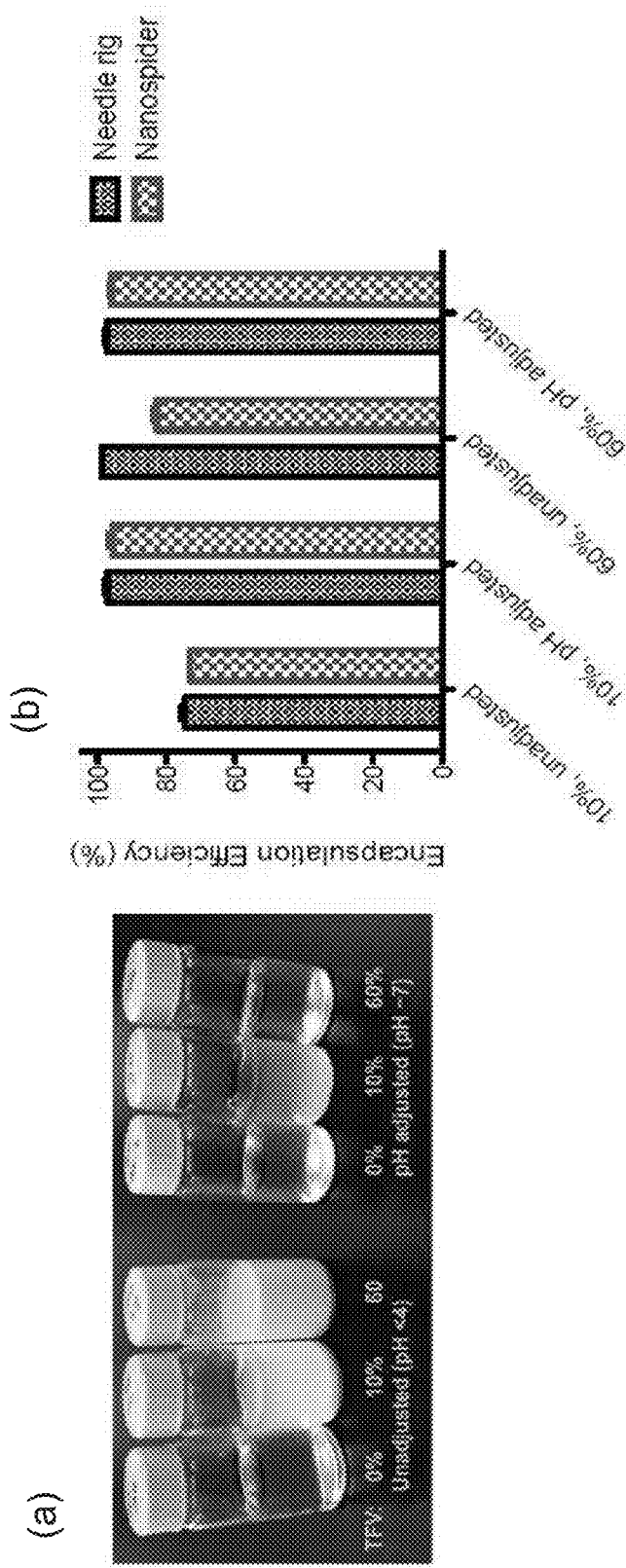
FIG. 28. Encapsulation efficiency is improved by adjusting solution pH. (a) The solubility of TFV in polymer solutions is visibly improved by using NaOH to raise solution pH. (b) The increased solubility of TFV in solution translates to an increased encapsulation efficiency of TFV in PVA nanofibers, measured by analyzing drug content in dissolved fibers with HPLC.
Figure 29:
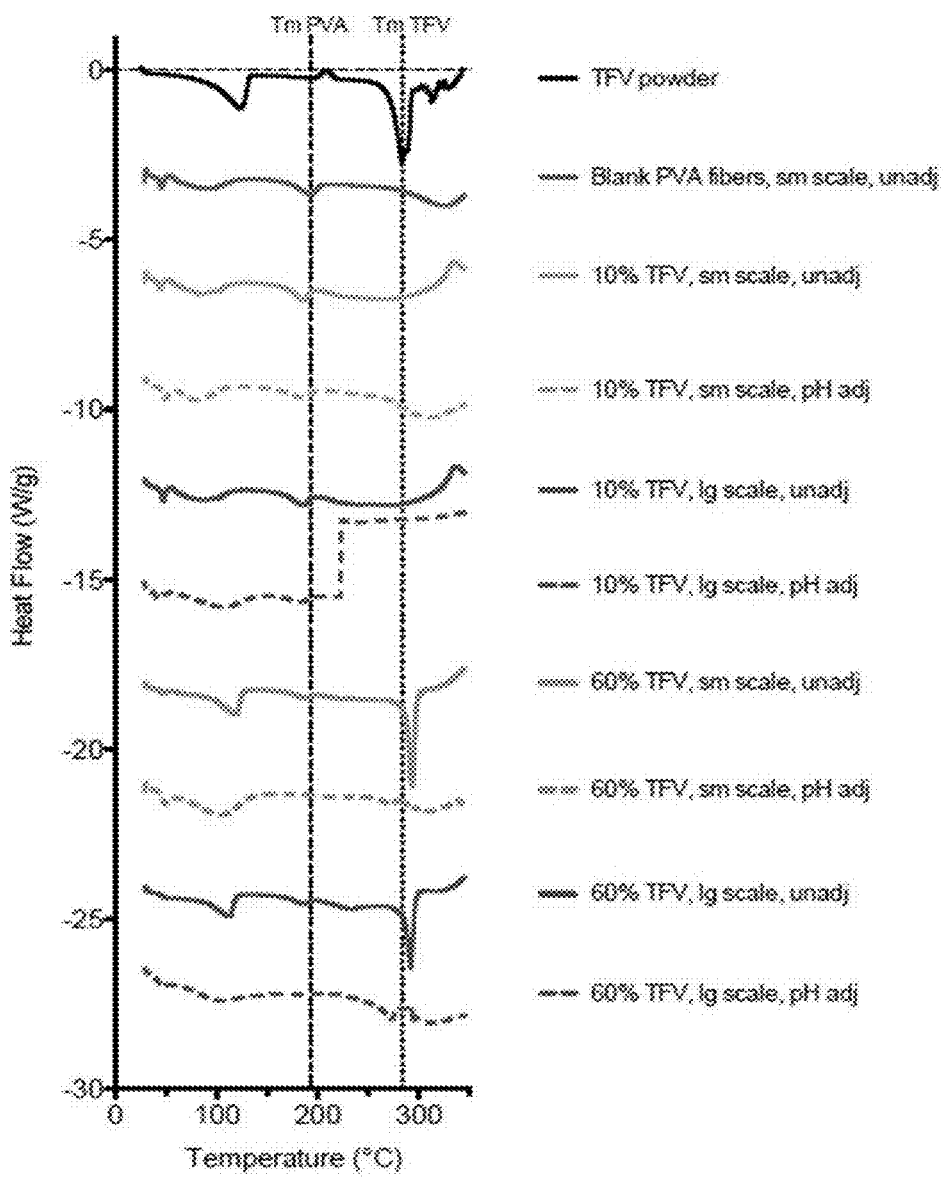
FIG. 29. Increasing TFV solubility prior to electrospinning reduces the final crystalline drug content in fiber meshes. Representative DSC thermograms of TFV-containing fibers and controls (TFV drug standard and blank PVA fibers) are displayed here. While a large peak indicative crystalline is present for unadjusted 60% TFV fibers, fibers made from pH-adjusted 60% TFV solutions do not have this peak. Vertical lines indicate the melting temperatures of PVA (193° C.) and TFV (283° C.) standards.

For PVA/TFV fibers, the conductivity of the electrospinning solution increased greatly upon pH-adjustment using 10 M NaOH. Electrospinning was successful for 0-60% TFV/PVA solutions and produced fibers with diameters ranging from 140-320 nm. (FIG. 24) The fiber could be produced on both on smaller needle-rig apparatus and Nanospider apparatus, it was observed that TFV promotes fiber dissolution relative to blank fibers at pH 7.4 and 4.3, observable both qualitatively and via measurement of dissolution at pH 7.4 and 4.3. (FIG. 25). Burst release of TFV was observed within 5 minutes at pH 4.3 and 7.4 and was similar for meshes electrospun on small scale and large scales, as shown via cumulative release of TFV in various produced fibers (FIG. 26). The Inventors observed that pH-adjusted PVA-TFV fibers containing 60% TFV have less than 2% crystalline drug, compared with 87-91% crystalline drug for unadjusted (FIG. 27). To obtain fibers with reduced crystallinity, TFV-containing PVA electrospinning solutions were pH-adjusted to ~7 using 10 M NaOH and encapsulation efficiency is improved by adjusting solution pH (FIG. 28). Solubility of TFV in polymer solutions is visibly improved by using NaOH to raise solution pH, resulting in increased encapsulation efficiency of TFV in PVA nanofibers, measured by analyzing drug content in dissolved fibers with HPLC. Further, increasing TFV solubility prior to electrospinning reduces the final crystalline drug content in fiber meshes as shown via representative DSC thermograms (FIG. 29).

It appears pH of the electrospinning solution improves actual tenofovir drug loading/encapsulation efficiency because of the pKa of tenofovir, not exclusively due to its hydrophilic/hydrophobic nature. Tenofovir has a pKa around 3.75, so increasing the solution pH to ~7 dramatically increases the amount of tenofovir in ionized form, making it more soluble. Thus, depending on the pKa of the drug, the solution pH could be adjusted either up or down to increase drug solubility. For the PVA/TFV combination, electrospun fibers can be produced from solutions in the range of pH 3.3 to 7.5.

PVA-TFV fibers have been made in the range of 140-160 nm (Nanospider, 10% TFV pH-adjusted and 60% TFV unadjusted), 160-180 nm (Nanospider, 10% TFV unadjusted), 180-200 nm (needle rig, 10% TFV pH-adjusted and 60% TFV unadjusted), and >200 nm (other formulations) (Supplementary Table 5). Solution pH, conductivity, and viscosity were measured for PVA/TFV solutions. All of these solutions were able to be electrospun into fiber meshes, so this provides an exemplary range of these properties that result in electrospinnable solutions. The measured range of pH (3.3-7.0), conductivity (0.075-14.94 mS/cm), and viscosity (0.45-2.51 Pa*s at 10 rad/s) resulted in fibers with similar diameters and drug release kinetics.

Example 3

Physicochemically Diverse Drugs: TFV and LVN

Hydrophilic antiretroviral TFV, and hydrophobic LNG have significantly different physicochemical properties that ordinarily precludes their combination in current vaginal dosage forms. TFV is hydrophilic, with a logP of −1.6 and aqueous solubility of 1.87 g/L, while LNG is highly hydrophobic, with a logP of 2.8 and aqueous solubility of $1.42 \times 10^{-3}$ g/L. PVA can be used as a polymer for drug loaded fibers as it is generally regarded as safe by the FDA, specifically including use in vaginal products. For the current study, the Inventors investigated the in vitro drug release and antiretroviral activity of the TFV and LNG combination in composite electrospun fabrics, including delivery of the two drugs from within the same fiber (combined fibers) or from separate fibers in a stacked or interwoven architecture. In addition, the Inventors investigated the role of fabric thickness on the kinetics of TFV and LNG release from stacked composites. The results described herein demonstrate the feasibility of assembling different micro-scale geometries that are macroscopically indistinguishable but result in molecularly unique medical fabrics for TFV and LNG co-delivery. It was observed that the release of LNG from composite fabrics is largely unaffected by geometry, thickness and drug loading. However, the release of TFV was slower when combined in the in the same fiber with an equal ratio of TFV to LNG when compared to a high ratio of TFV to LNG. It was further observed that TFV drug release decreased with increasing fabric thickness. The antiviral activity of TFV against HIV-BaL infection in TZM-bl cells was similar to the unformulated drug, and was not affected by the architecture of the composite fabrics. These results emphasize the importance of considering fabric microarchitecture, thickness and drug interactions when co-delivering drugs from fibers.

Example 4

Figure 2:
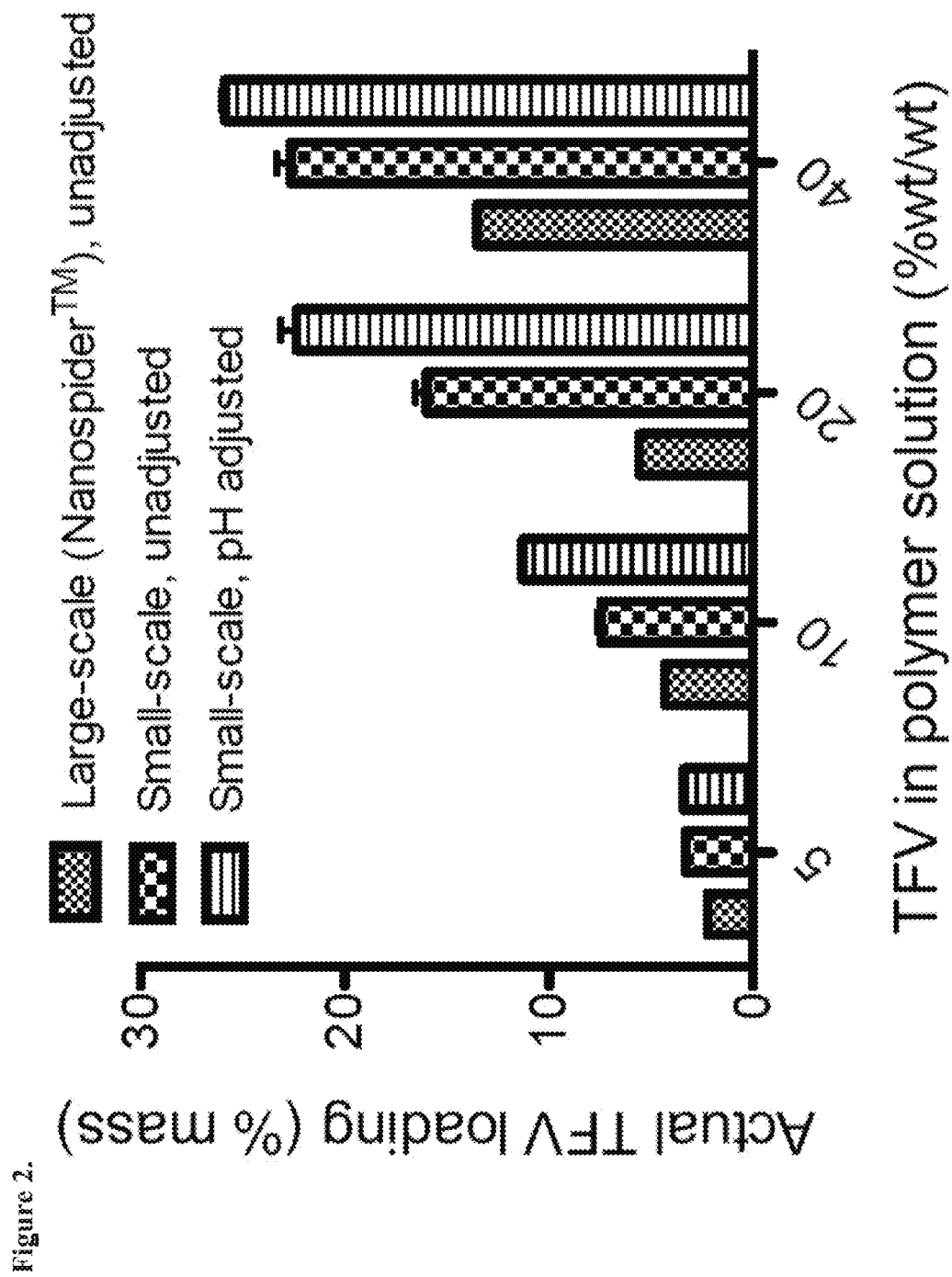
FIG. 2. Drug loading of TFV in PVA fibers. As shown, increasing pH adjustments can improve TFV loading, and production with significant TFV loading can also be achieved using larger scale apparatuses.
Figure 3:
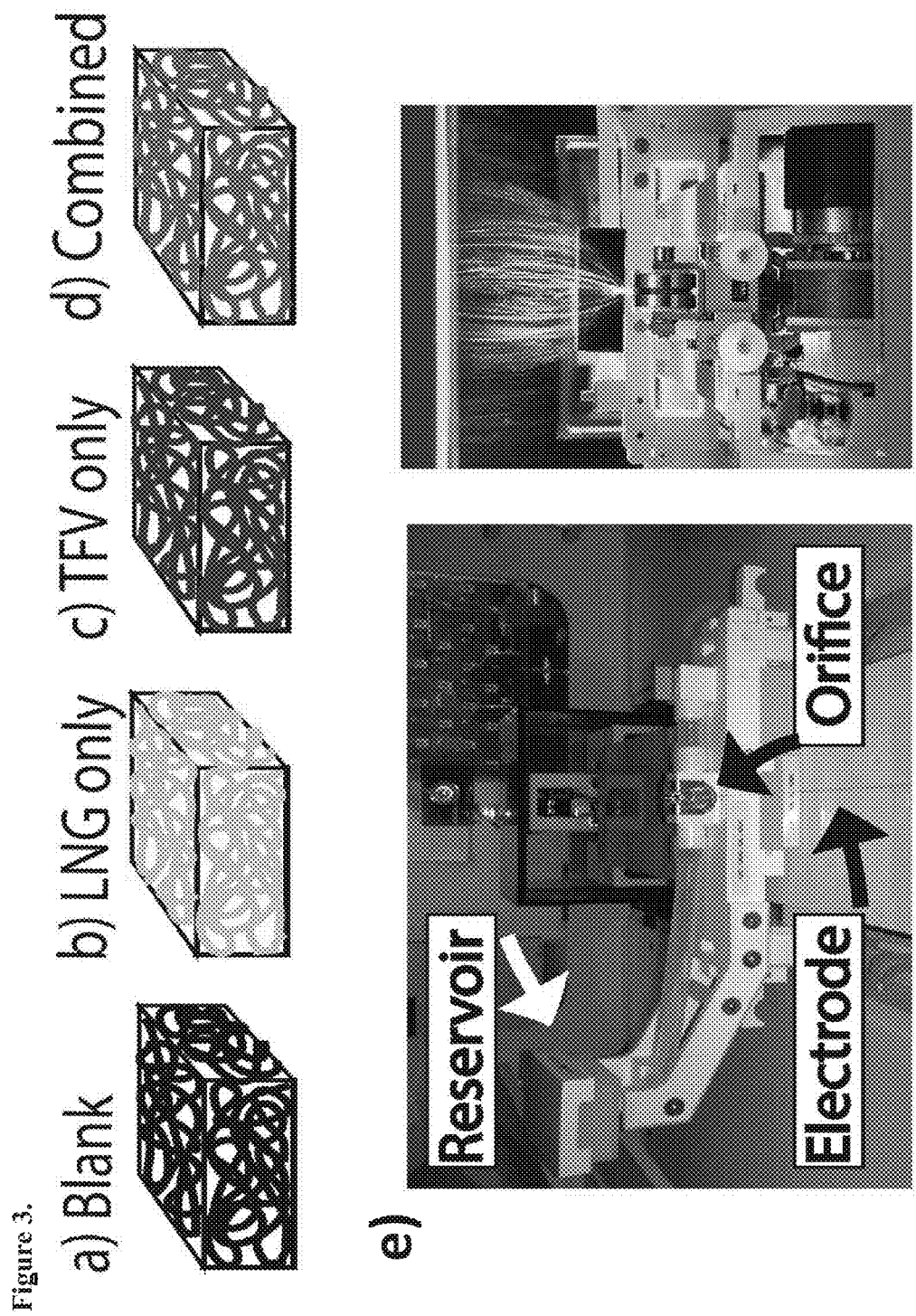
FIG. 3. Comparison co-delivery of drugs in electrospun fabrics. PVA prepared with (a) no drug (b) levonorgestrel ("LNG") (c) TFV (d) the same fiber using an (e) Elmarco NS 1WS500U single 20 mL carriage and free-surface wire electrode, with theoretical drug loading of 20% (wt. drug/wt. polymer).
Figure 6:
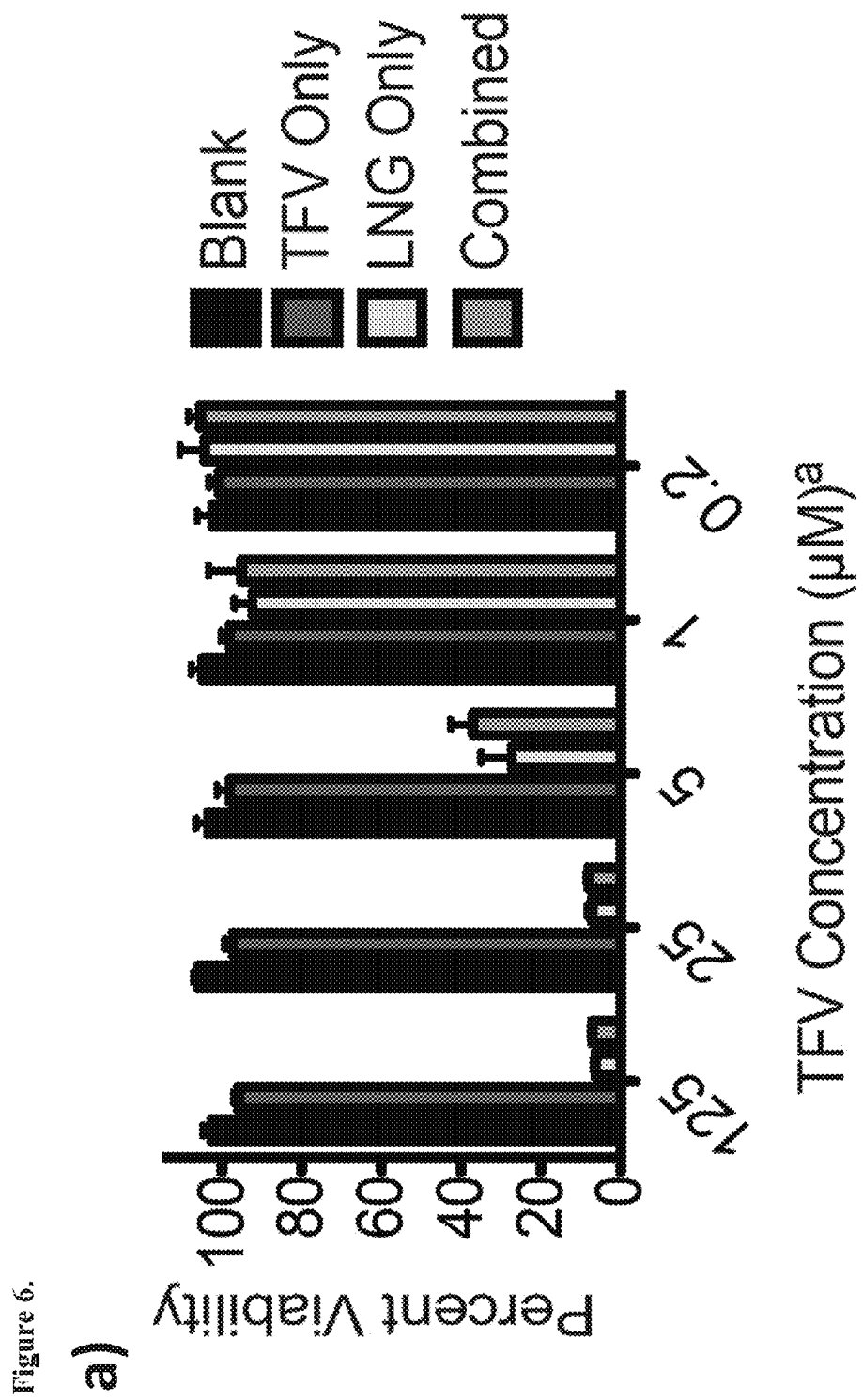
FIG. 6. Cytotoxicity and HIV-1 Inhibition. (a) TZMbl cytoxocity is induced by high concentrations of LNG, but not TFV. (b) TFV IC40 levels of HIV-1 Bal inhibition maintained in electrospun fibers. Concentration labels refer to TFV concentration in the well, except for blank and LNG only fiber, in which comparable polymer or LNG concentration as the combined fibers was used. The ratio of TFV:LNG in the combined fibers was 1:23. Due to high levels of cytotoxicity from higher concentration of LNG, fabrics with relevant daily dosing ratios of LNG and TFV (1:2000) was used for the inhibition assay.
Figure 6:
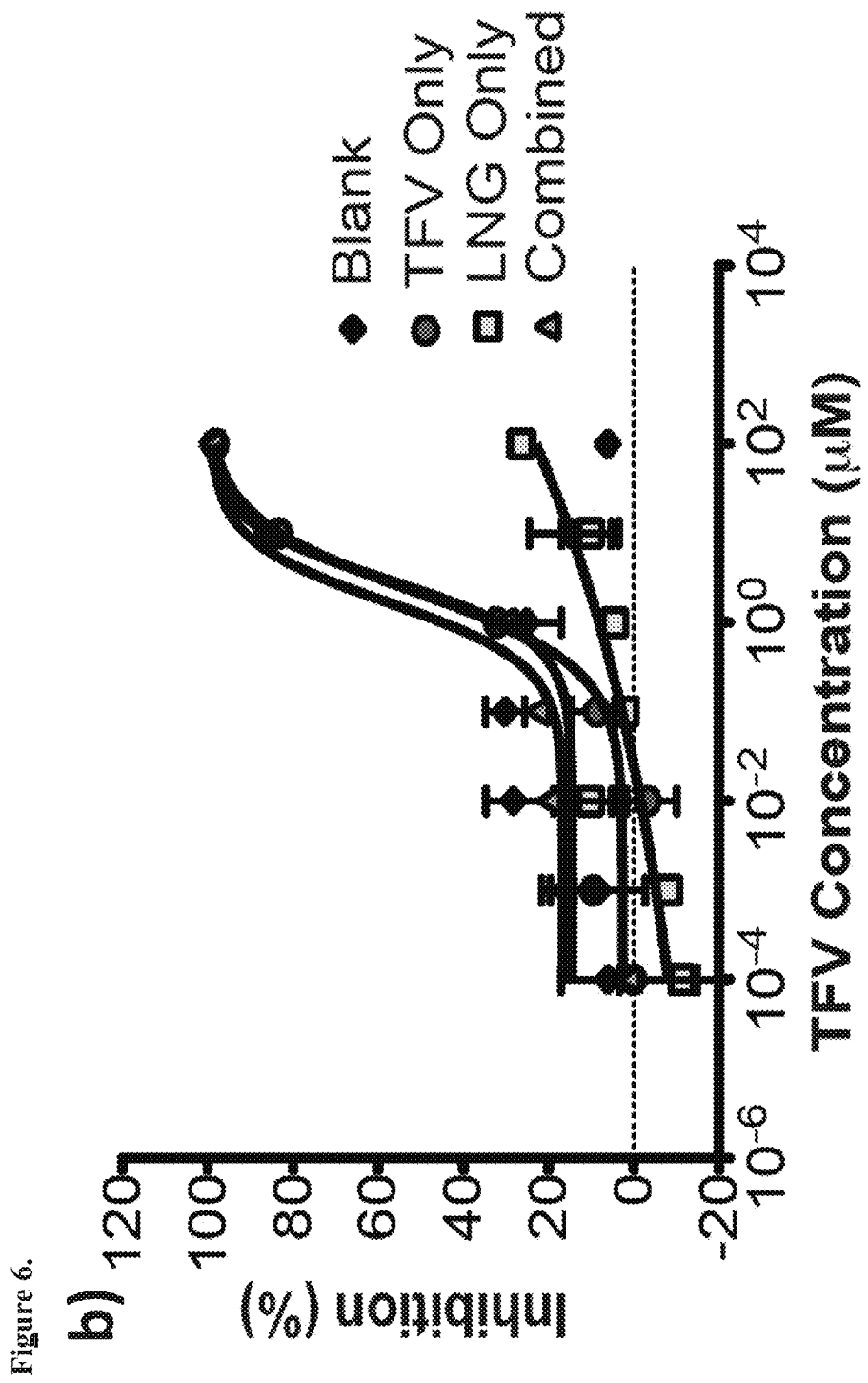
Figure 7:
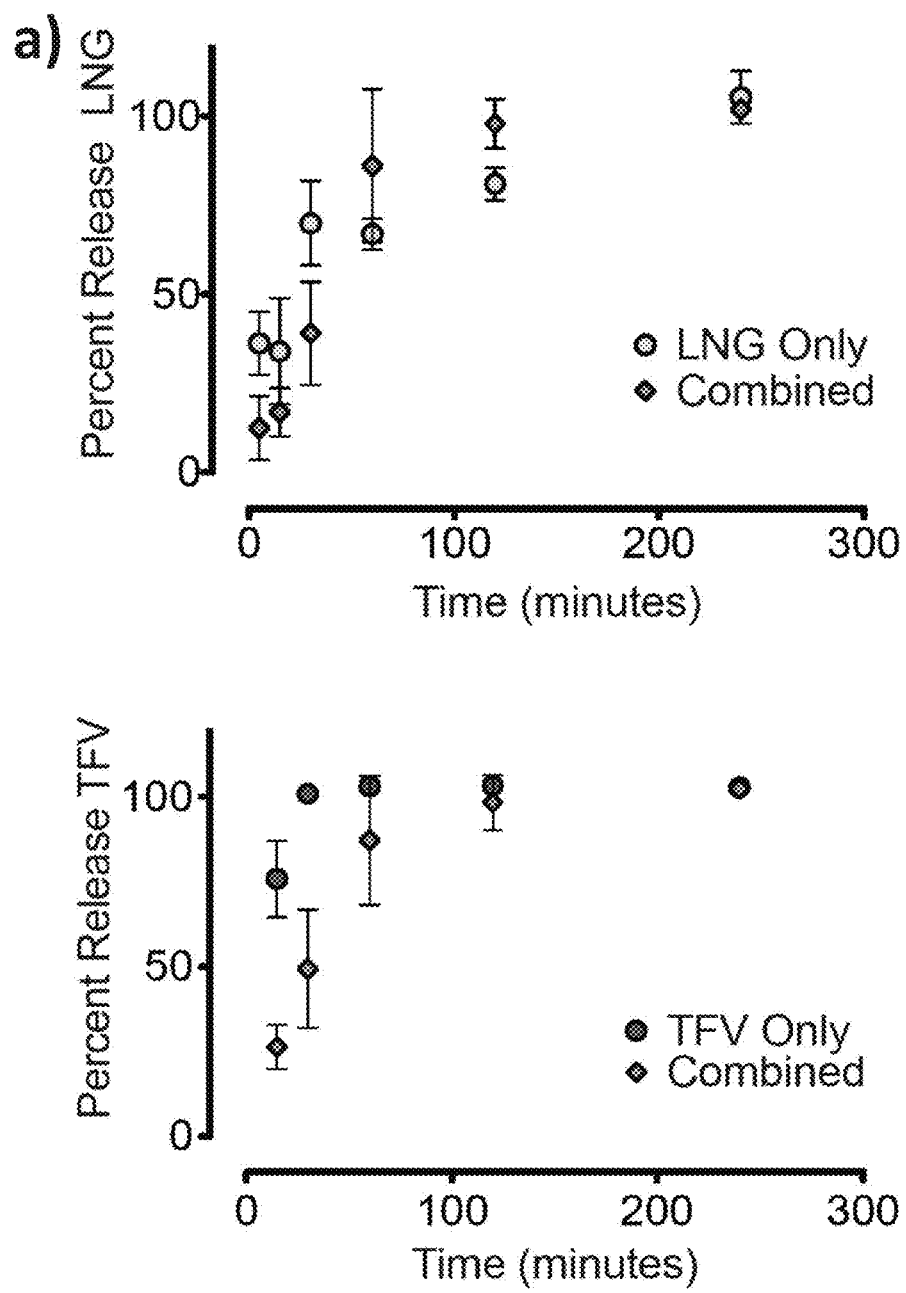
FIG. 7. In vitro release. (a) TFV release is two-fold slower when co-loaded with equal amount of LNG (upper panel), but LNG release is unaffected (lower panel). (b) TFV release is unaltered by co-loading with LNG at a ratio of 2000 to 1 (upper panel), equivalent dose of TFV is released faster than LNG from single- and multiple-drug fibers (lower panel).
Figure 7:
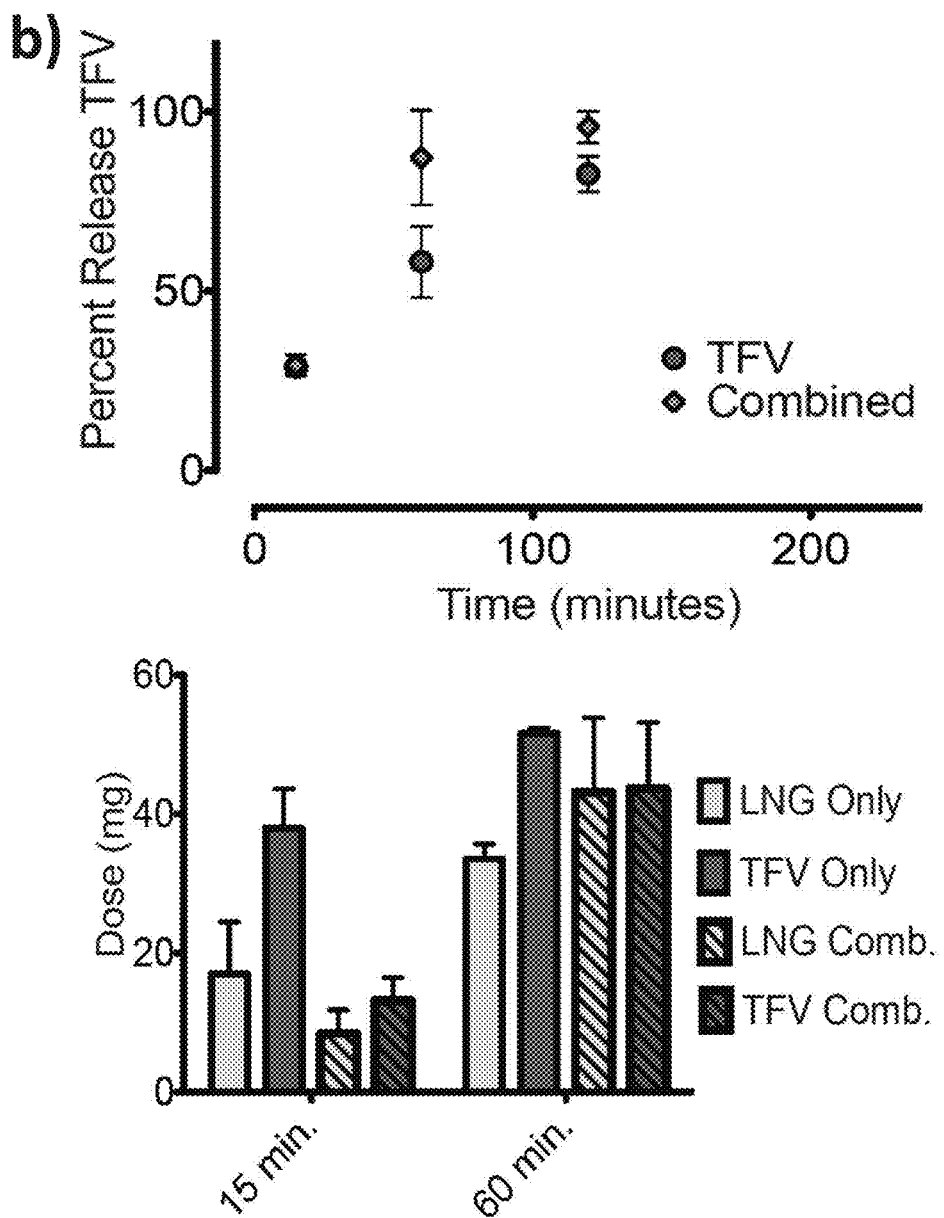

Successful Production of TFV-Loaded PVA Fibers: Enhanced Material Recovery from Increased Solution Conductivity Using both the described small-scale laboratory system and the large-scale Nanospider™ system, all five of the described PVA solutions containing 0-40% (wt/wt) TFV can be produced. SEM images of fibers spun on the small-scale system for pH-unadjusted and pH-adjusted solutions and of fibers spun on the large-scale system are shown (FIG. 1). Consistent fiber-like morphology for all electrospun meshes is observed. Interestingly actual TFV loading was found to increase with increasing wt % TFV in solution (FIG. 2). Furthermore, material recovery was increases with TFV content for both small and large-scale systems. Without being bound by any particular theory, this may be expected to result from increased solution conductivity. Such results support the scale-up of drug-loaded fibers and that the addition of TFV can result in improved yields compared with currently optimized PVA meshes.

Example 5

Successful Production of TFV-Loaded PVA Fibers: Increased pH Improves Drug Loading and Solution Conductivity Raising polymer solution pH may also be a feasible strategy to increase the solubility of TFV, as such conditions can allow for higher actual drug loading and reduced drug crystallinity in the final fibers. For example, 10 M NaOH could be effectively used to raise the solution pH and drug precipitate disappears at pH>7. Actual TFV loading in fibers is significantly increase by raising the solution pH ($p<0.05$). Increasing pH also leads to dramatic increases in conductivity of approximately 5-fold to 45-fold for 5% and 40% (w/w) TFV solutions, respectively (FIG. 2).

Example 6

Polymer Solution for Co-Delivery of Drugs

Polymer solutions re prepared using poly(vinyl alcohol) ("PVA") (Sigma-Aldrich) with MW 85K-124K and 87-89% hydrolysis. Levonorgestrel was purchased from Sigma Aldrich and tenofovir was a gift from CONRAD. The Alexa Fluor 488 and 555 hydrazide sodium salts used in fluorescently labeled fibers were purchased from Life Technologies Corporation. PVA is dissolved in deionized water at 10% wt./vol. Drugs are mixed with polymer solution at 20% wt. drug/wt. polymer (for equal loading fibers) or 0.0067% (LNG) and 15.3% (TFV) wt. drug/wt. polymer (for relevant daily dosage fibers) and allowed to stir for at least 6 hours prior to electrospinning Fluorescent dyes were added to polymer solution at 0.025% wt./vol. and protected from light.

Example 7

Electrospinning PVA for Drug Co-Delivery, Microarchitecture Formation

Polymer solutions are electrospun using an Elmarco NS 1WS500U with a free surface wire electrode. The fabrics are prepared in 50-60% relative humidity, with an air input of ~65 m3/h, air output of 267.8 m3/h, electrode distance of 160 mm, collecting electrode voltage of −25 kV, spinning electrode voltage of 60 kV, wire speed of ~30 mm/h, cartridge speed of ~100 mm/s and cartridge traveling distance of 250 mm using a 0.7 mm diameter orifice, unless otherwise specified. Batches can be halted after no more fibers are visibly spinning.

All fabrics are spun onto polypropylene substrate provided by Elmarco, unless otherwise stated. Fabrics can be stored under vacuum until use in subsequent experiments. Fabrics that contained no drugs or only a single drug are spun using 15 mL of appropriate solution in a single 20 mL cartridge.

For different microarchitectures, the microarchitecture referred to as "stacked" is prepared by spinning 7.5 mL (in the 20 mL cartridge) of polymer solution containing LNG and then 7.5 mL of polymer solution containing TFV on top, to produce a fabric with distinct layers. The "interwoven" microarchitecture is prepared by loading 7.5 mL of LNG-loaded solution into one side of a 40 mL cartridge with dual 20 mL reservoirs, and 7.5 mL of TFV-loaded solution into the other side and allowing both reservoirs to flow simultaneously. "Combined" microarchitecture is spun using 15 mL of a solution that contained both LNG and TFV in the 20 mL cartridge.

Fluorescent fibers are prepared in an identical manner except fluorescent Alexa Fluor dye (488 with LNG, 555 with TFV) is added to the drug-loaded solutions and a slide is attached to substrate during the middle of the run to collect a thin layer of fibers for imaging. Thicker fabrics of the stacked and interwoven microarchitectures are prepared using the same volume of solution, but limiting the distance the cartridge could travel to decrease the total area of fabric. The distance can be shortened from 250 mm to 150 mm and 100 mm.

Example 8

Solution, Fiber and Fabric Characterization

In various applications, solution properties are characterized before electrospinning Density is measured by massing a known volume of solution in triplicate and averaging the measurements. Conductivity is measured using a bench top Thermo Scientific Orion Star A212 Conductivity Meter. pH is measured using a bench top Thermo Scientific Orion Star A111 pH Meter. Surface tension is measured using a Kibron AquaPi Surface Tensiometer according to manufacturer's protocol. Viscosity is measured using a TA Instruments AR-G2 Series Rheometer at a constant strain of 4% with a cone (angle=1° 58' 48", diameter=40 mm) and plate geometry.

Fabrics are sputter coated with a mixture of gold and palladium for 90 s and imaged at magnifications of 500× and 5,000× using a Sirion scanning electron. Fiber diameter is determined using NIH Image J by drawing a diagonal line across the 5,000× image and measuring the diameter of 45 fibers on that line, on three separate micrographs. Thermograms are generated using a TA Instruments Auto Q20 Differential Scanning calorimeter with a run consisting of a ramp from 10 to 350° C. with a sampling interval of 1 s/point. Samples re prepared in a Tzero aluminum pan at a mass of 5-7 mg. Heat flow is normalized to sample weight. Relative crystallinity of drugs in electrospun fibers is calculated using the following equation:

$$\% \text{ Relative Crystallinity} = 100 * \frac{\text{Area under curve}_{drug\ samplepeak} * \text{Mass drug}_{sample}}{\text{Area under curve}_{drug\ standard} * \text{Mass drug}_{standard}}$$

TA Universal Analysis software is used for both rheometry and DSC data collection and analysis. The percent yield and productivity were calculated using the following equations:

$$\% \text{ Yield} = 100 * \frac{\text{Actual total mass fibers}}{\text{Calculated mass solids in volume of solution added to catridge}}$$

$$\text{Productivity} = \frac{\text{Actual total mass fibers}}{\text{Total area fibers} * \text{Spinning time}}$$

The thickness of the fabrics is measured using calipers and averaging three measurements from different locations at the center of the fiber mat. Fluorescent fibers were imaged using a Zeiss Leica TCS NT/SP confocal microscope, and on a DMIRBE inverted microscope with a 40× oil objective.

Example 9

Measuring Drug Loading and Release

Drug loading is analyzed by dissolving approximately 5 mg of fibers in 20 mL of a mixture of 1:1 isopropanol:water in a glass vial. Triplicate samples are allowed to dissolve overnight at 37° C. on a rotational shaker and concentration is quantified using a Shimadzu Prominence LC20AD UV-HPLC system. A Phenomenex Luna C18 column (5 µM, 250×4.6 mm) and LC Solutions software are used to analyze samples.

A method for dual analysis of TFV and LNG is developed using the following gradient method using mobile phase A (0.1% formic acid in water) and mobile phase B (acetonitrile). The run consisted of 0-5 minutes 72% mobile phase A, 5-10 minutes ramp to 15% mobile phase A, 10-20 minutes 15% mobile phase A, 20-25 minutes ramp to 72% mobile phase A, 25-30 minutes 72% mobile phase A. The total method time is 30 minutes, with an oven temperature of 30° C., a flow rate of 1 mL/min, and an injection volume of 20 μL. LNG is detected at 238 nm at a retention time of 18.5 minutes. TFV is detected at 259 nm at a retention time of 2.3 minutes. LNG had a linear standard range from 0.05 μg/mL to 100 μg/mL and TFV had a linear standard range from 0.01 μg/mL to 200 μg/mL.

In vitro release was analyzed in a 1:1 solution of isopropanol:water due to the limited solubility of LNG in water. Sink conditions were maintained throughout the study for both drugs in the release media. Approximately 5 mg of fibers were prepared in triplicate and an appropriate volume of release media was added to maintain sink conditions of 2.6 mg/mL LNG as has been reported. Samples were incubated at 37° C. on a rotational shaker, and 200 μL samples of release media was taken as indicated. Fresh media was added to replace sample volume at each timepoint.

Example 10

Cytotoxicity and HIV Inhibition Assays

TZM-bl cells and HIV-1 BaL isolate are obtained. TZM-bl cells are a HeLa derived cell line that express CD4, CCR5 and CXCR4. Cells re plated in a black 96-well plate at a density of 5,000 cells/well (Corning, Corning, N.Y.) and maintained in Dulbecco's Modified Eagle Medium (DMEM) (Gibco Life Technologies) with 10% fetal bovine serum (Hyclone), 1% 100× penicillin/streptomycin (Invitrogen) and 1% 200 mM L-glutamine. Cells are incubated in 5% CO2 and 37° C. for 24 h prior to exposure to drugs. Fibers were sterilized by UV irradiation for one hour per side prior to use. Treatments were added at a volume of 50 μL. Cytotoxicity is analyzed using the CellTiter Blue assay (Promega) to assess TZM-bl cell viability after 48 h of exposure to drug eluates from fiber release in cDMEM (24 h release, triplicate wells for each sample). Percent viability is calculated by normalizing to the average of media control wells (n=9). For composite fabrics, the drug concentration shown applies to both the amount of LNG and of TFV (1:1 ratio). Positive control (12.5% DMSO) results in 4.6% viability. Data represents triplicate wells with error bars indicating standard deviation.

For the HIV-infectious inhibition assay, 100 μL of HIV-1 BaL (240 TCID50/well) is added to wells 1 h after drug treatment (24 h release eluates). Media is removed from wells after 48 h and 100 μL of phosphate buffered saline (Gibco Life Technologies) and 100 μL of Bright-Glo Luciferase reagent (Promega) were added to wells. Inhibition of infectious activity is quantified by measuring luminescence on a plate reader (Tecan). IC50 values of drug compounds re estimated using sigmoidal regression in Graphpad Prism, version 5.0.

Example 11

Statistical Analysis

Drug release is reported as mean±standard deviation, and values at each timepoint are compared using a two-way ANOVA to compare all microarchitectures and a Bonferonni post-test to directly compare values for two individual microarchitectures. Two-sided tests were used at a significance level of α=0.05 for all hypothesis testing. Statistical analyses are performed in Graphpad Prism, version 5.0.

Example 12

Properties of Electrospun Fibers

Free-surface electrospinning is used to fabricate medical fabrics of various microarchitectures for combination delivery of TFV and LNG. The addition of LNG and TFV, either alone or in combination, to the PVA polymer solution leads to minimal differences in pH, surface tension, conductivity and viscosity.

For example, replacing up to 20 wt. % of the solids content with either drug alone results in an average change of only 10-15% in conductivity, viscosity or surface tension. However, when LNG and TFV are added in combination, this results in larger changes of 20-30% in these same solution properties. A significant reduction in pH for solutions containing TFV is observed, which is a result of the pKa of the phosphonic acid functional group of TFV. However, the magnitude of the changes in these solution properties does not appear to affect either the overall fabric or individual fiber properties.

Figure 8:
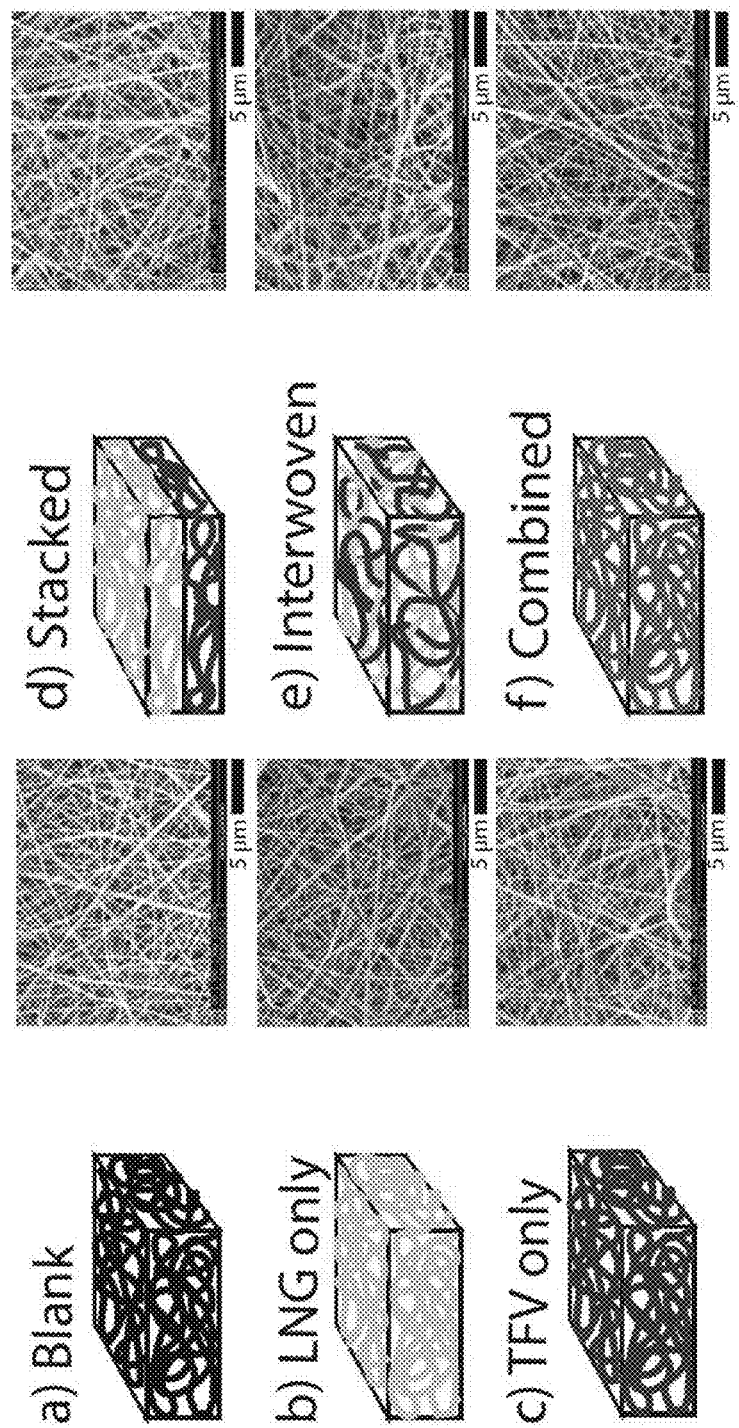
FIG. 8. Medical fabric microarchitectures for topical delivery of single and combination drugs. LNG and TFV were delivered alone (b,c) or together using different composite microarchitectures (d,e,f). Vehicle control fabrics (blank) were prepared with only the PVA polymer (a). Schematic shows micro-scale rendering of idealized dispersions of LNF and TFV in fibers (left), and actual scanning electron micrographs (right) of representative fabrics that were produced.

Importantly, irrespective of the drug loaded (LNG alone, TFV alone, or LNG/TFV combined) or composite microarchitecture (stacked, interwoven, or combined), the fiber fabrics are macroscopically indistinguishable from each other. They appeared white and silky to the touch and were flexible and easily folded. SEM microscopy indicates that the individual polymer fibers have a smooth and rounded morphology and a measured average diameter of ~250 nm (FIG. 4). The fabrics re also free of physical defects, such as beading, except in the case when TFV and LNG were combined together within the same fiber (FIG. 8). One can attribute the minimal amount of beading to the almost two-fold higher drug loading for these fiber formulations compared to the formulations containing only single drugs.

Example 13

Encapsulation Efficiency

Figure 9:
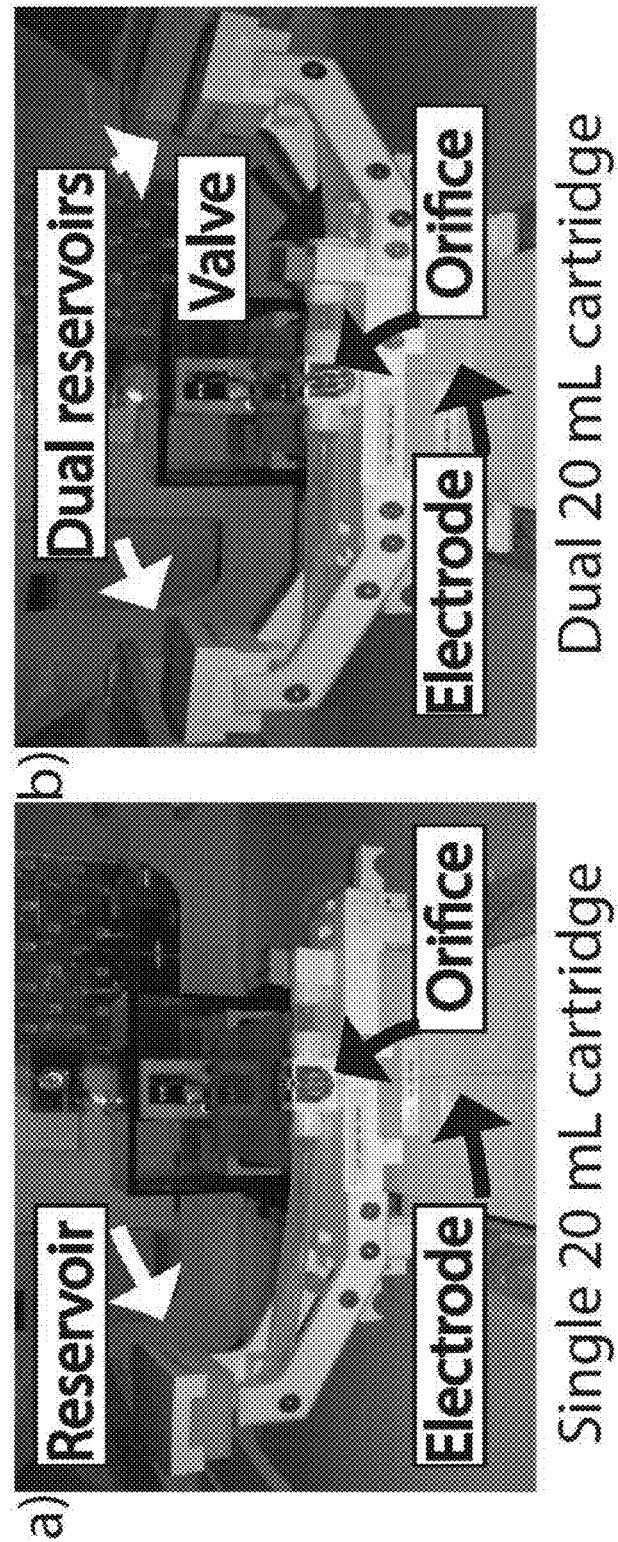
FIG. 9. Photographs of NS 1 WS500U cartridges used to fabricate TFV and LNG medical fabrics. (a) A single 20 mL reservoir was used to electrospin blank, LNG only, TFV only, stacked and combined fibers. (b) A dual 20 mL reservoir was used to electrospin interwoven fibers. Images depict the reservoir housing for the electrospinning solution, which drains via tubing toward an orifice where the solution is deposited onto the wire electrode.

Using the described techniques, one can achieve high encapsulation efficiencies of >80% for virtually all of our fiber formulations, although except for composite interwoven fibers of TFV and LNG, which may possess some limitations. This may be due to a processing artifact leading to TFV encapsulation efficiencies <50% and LNG encapsulation efficiency >150%. In this case, the cartridge used to electrospin interwoven fibers has an asymmetric geometry that includes an extra valve and length of tubing between the solution reservoir and orifice (FIG. 9), resulting in impeded flow and deposition of the TFV onto the wire electrode. The comparatively low yield of electrospun fabrics, ranging from 30-70% of expected recoverable solids, may be due to a substantial amount of residual solution left in the electrospinning cartridge from when the fluid level dropped below the orifice. Other than leftover solution in the cartridge, there is no loss of polymer or drug.

High productivity for all polymer/drug combinations is achieved on the NS 1WS500U, with observed throughput rates of up to 27 g/m2 of fibers per hour. Overall, these results show the capability to incorporate physicochemically diverse agents into a single composite fabric with varying microarchitecture and high encapsulation efficiencies, demonstrating the capacity to produce the fabrics on a production-scale instrument. The solution properties of drug-containing electrospinning solutions re within an appropriate range for electrospinning fibers of varying microarchitecture, and the resulting fabrics were macroscopically indistinguishable from each other.

Example 14

Differential Scanning Calorimetry Analysis of Electrospun Fibers

Figure 10:
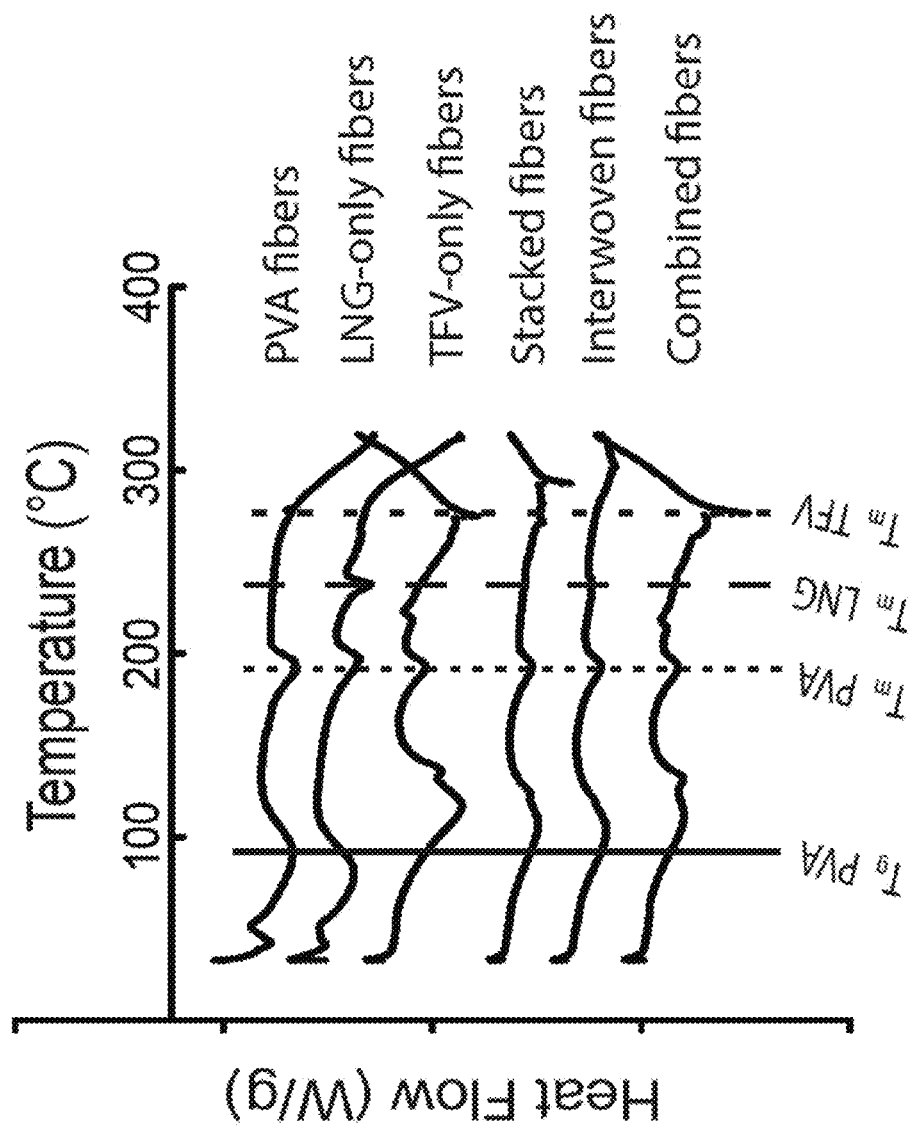
FIG. 10. Thermograms of electrospun fibers of varying microarchitectures as determined by differential scanning calorimetry. The Tg and Tm peaks of the pure components are indicated with the lines.

Differential scanning calorimetry ("DSC") can be used to characterize the solid dispersion of LNG and TFV in the final fiber products produced by electrospinning. By measuring the glass transition temperature (Tg) of the electrospun PVA fibers and melting temperatures (Tm) for the individual fiber components (PVA, TFV, LNG), one can determine the crystalline state of the components and identify interactions between the drugs and polymer. Further, one can quantify the percentage of crystalline drug content by normalizing the enthalpy of melting for the drug in PVA fibers to the enthalpy of melting for the pure drug. The Tm measured for PVA in all of the described formulations is around 195° C. (FIG. 10), which is consistent with measured values reported elsewhere. Likewise, the Tm for pure drug samples of LNG and TFV is 234° C. and 270° C. respectively, which is also consistent with reported values.

PVA is a semi-crystalline polymer and the described PVA fibers had a measured Tg of ~95° C. Incorporation of LNG does not significantly change the Tg of PVA fibers. However, upon addition of TFV, the Tg of PVA fibers does increase by >15° C. to ~110° C. This increase in Tg indicates that TFV, but not LNG, acts as a plasticizer and contributes to a more imperfect crystalline structure of the PVA polymer that makes up the bulk of the fiber. DSC thermograms for LNG fibers also show a unique endotherm at 240° C. that corresponds to the Tm of LNG. This endotherm is only detected in the LNG-only fibers, which also have up to 2-fold higher LNG loading (~17 wt. %) compared to the other LNG fiber formulations. Integrating the endotherm peak for LNG and comparing it with a pure LNG crystalline standard indicates that only ~1% of LNG exists in a crystalline form within the PVA fibers whereas the remainder is amorphous. Likewise, a unique endotherm at ~270° C. is detected in the TFV-only fibers which corresponds to the Tm of TFV. Analysis of total TFV crystallinity in the TFV-only fibers indicates that only 0.2% of the total TFV in the fibers exists in the crystalline state. Crystalline TFV is also detected in the stacked and combined fibers at values of 0.2% and 2.3%, respectively. No crystalline TFV is detected in the interwoven fibers most likely because these fibers had a much lower loading of TFV (~4%) and the amount of crystalline TFV in the fibers is below the detection limit. In summary, electrospun drug-loaded fibers can be prepared on the NS 1WS500U with minimal TFV and LNG crystallinity. Incorporation of TFV into the PVA fibers increased the Tg, indicating an interaction between the PVA and TFV, while incorporation of LNG had no effect.

Example 15

Visualization of Composite Microarchitectures

Figure 11:
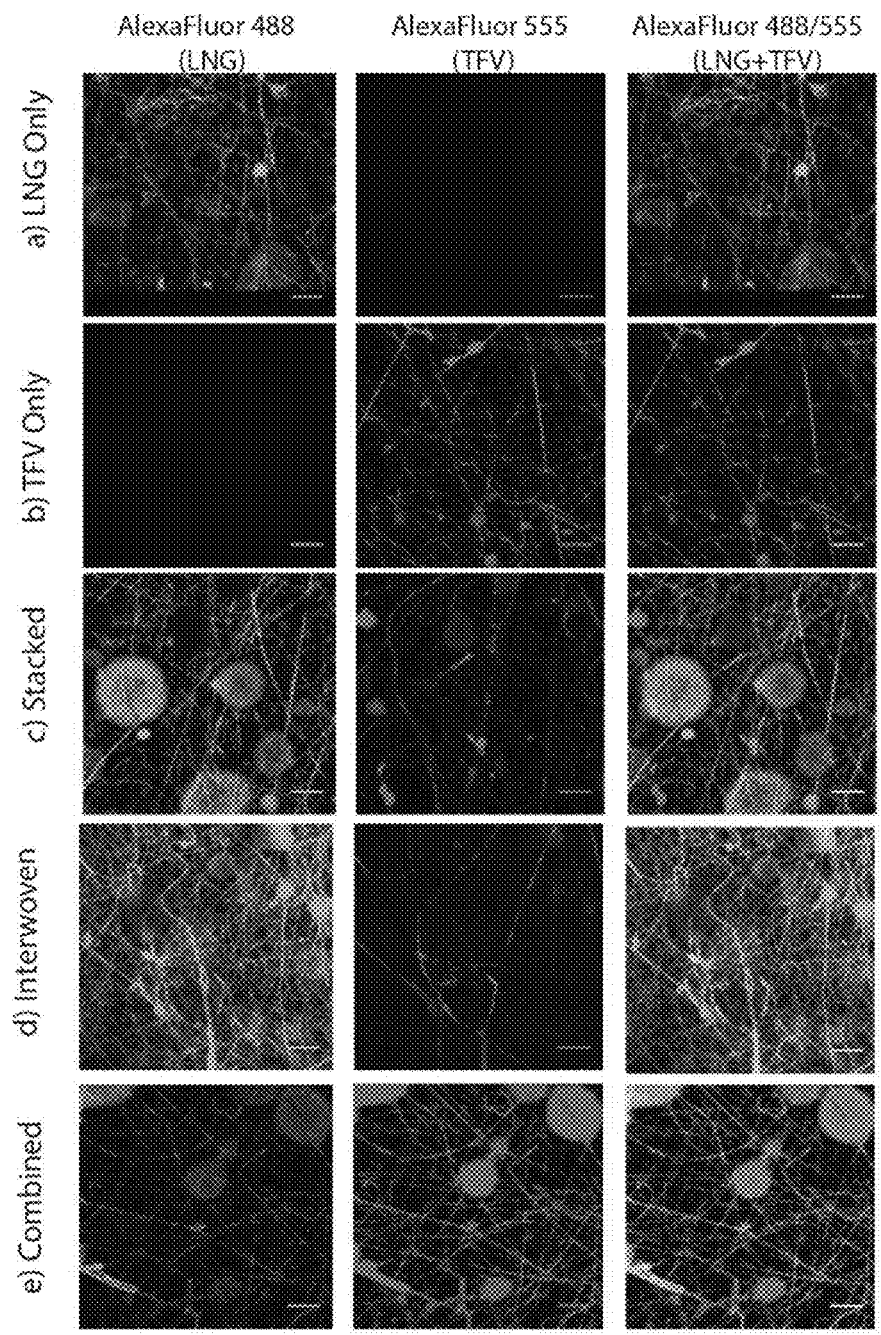
FIG. 11. Confocal images of fabric microarchitectures. LNG and TFV were fabricated alone (a,b) or combined in different composites (c-e). To visualize the underlying fabric microarchitectures, LNG solutions were co-loaded with AlexaFluor 488 and TFV solutions were coloaded with AlexaFluor 555. Fluorescently labeled fibers were analyzed with a confocal laser scanning microscope (Leica TCS NT/SP, Zeiss). Samples were scanned for AlexaFluor 488 (green channel, left), AlexaFluor 555 (red channel, center) and the two channels were merged (right) using NIH Image J to detect fluorescence co-localization.

Confocal microscopy can be used to visualize the stacked, interwoven, and combined composite microarchitectures by co-loading the fibers with drugs and different fluorophores. AlexaFluor 488 is added to the LNG solution whereas AlexaFluor 555 is added to the TFV. In this way, one can visualize LNG-loaded fibers in the green channel and TFV-loaded fibers in the red channel. Mixing of the fluorophores (and drugs) results in an orange color detected in the merge channel. Indeed, LNG-only fibers are observed only in the green channel and had no bleed through in the red channel (FIG. 11*a*). TFV-only fibers were observed only in the red channel and had no bleed through in the green channel (FIG. 11*b*). The stacked composites are imaged at the interface of the LNG/TFV layers, where one observes distinct red and green fibers (FIG. 11*c*). Imaging planes along the z-axis possess regions of only red or only green fibers, suggesting a microarchitecture composed of a distinct layer of LNG-only fibers as well as a distinct layer of TFV-only fibers. Importantly, in the merge image of the stacked composite, distinct green and red fibers are visible, indicating no mixing or co-localization of dyes within the fibers. In contrast to the stacked composites, the interwoven fabrics show intermingling LNG-only and TFV-only fibers, as well as orange fibers that are visible in the merged fluorescent images (FIG. 11*d*). This assortment of fiber compositions may be due to the ability of solutions to mix at the orifice, before fiber formation. The interwoven fibers show very few red fibers compared to the number of green fibers, which supports the observation of low TFV loading in this fabric composition. Combined composite fabrics are expected to show co-localization of the green and red fluorescence. Visualization of both fluorophores in the combined microarchitectures confirmed the presence of both dyes (FIG. 11*e*), as well as the ability to image both dyes in a single fiber. For the fluorescent microscopy, fiber fabrics are collected onto a glass slide rather than the standard backing material. Although composites are processed at identical conditions in both cases, the glass slides may alter the electric field and cause polymer droplets to collect. These droplets are not observed by SEM for fibers collected on the standard backing material. The confocal images indicate that three distinct composite microarchitectures are achievable by varying processing specifications, including preparation of fabrics with distinct layers of single dye (drug) fibers, fabrics with both distinct and mixed dye (drug) fibers, and fabrics with combined dye (drug) fibers.

Example 16

In Vitro Release of TFV and LNG: Differential Release Kinetics

Figure 12:
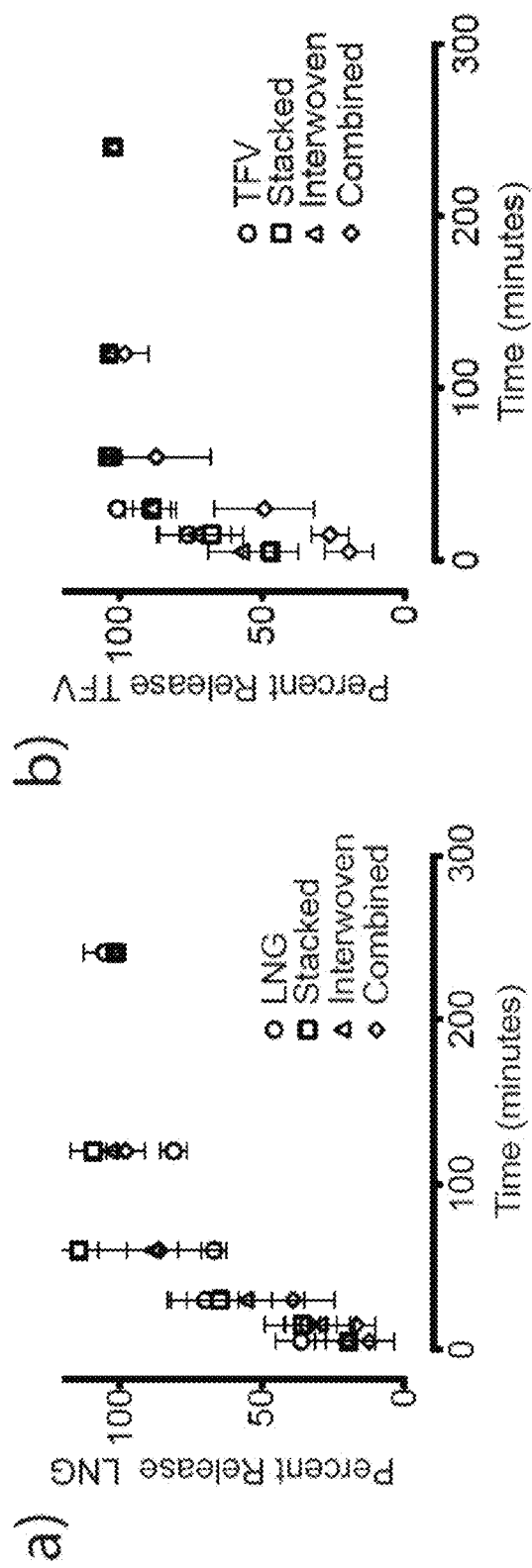
FIG. 12. In vitro release profiles and dosage profiles of LNG and TFV delivered from different composite fibers. Fabrics were prepared at 1:1 equal TFV:LNG mass loading (a-d) or at 2000:1 TFV:LNG mass loading (e-f). The delivered dose was calculated at each time point using the percent release at that time and an assumed delivery of 500 mg of total fabric. Values are reported as mean and standard deviation for n=3.
Figure 12:
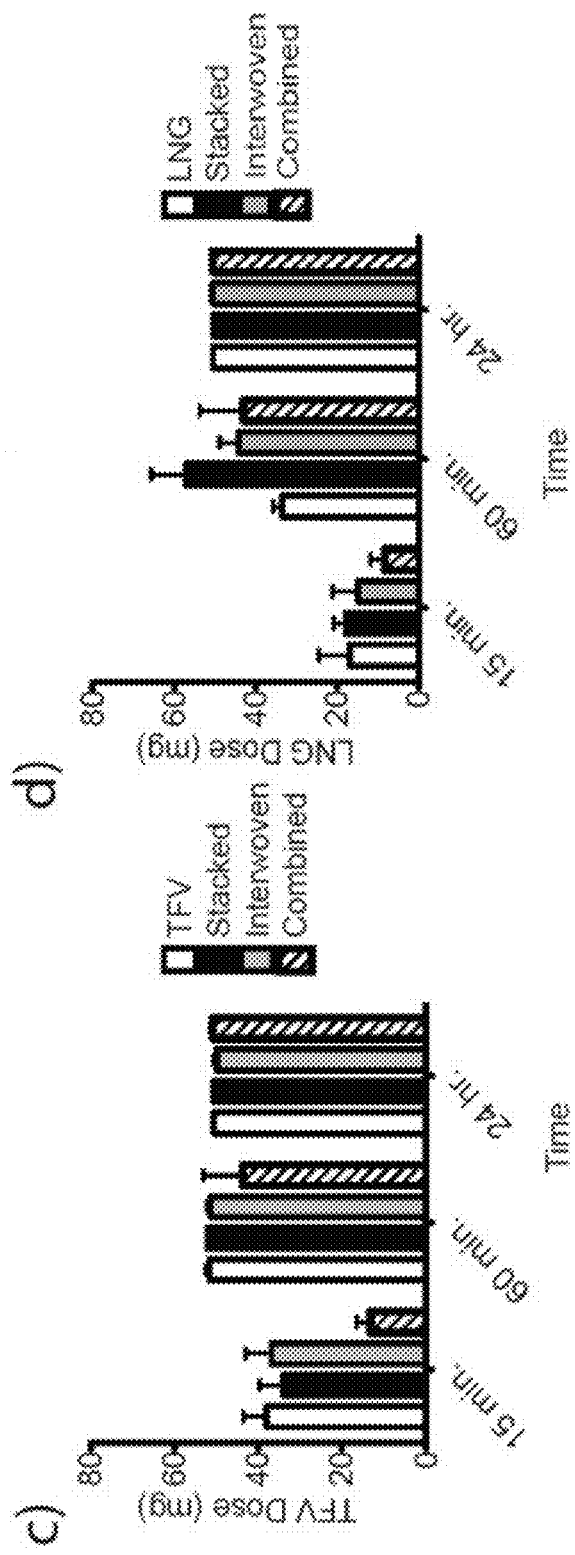
Figure 12:
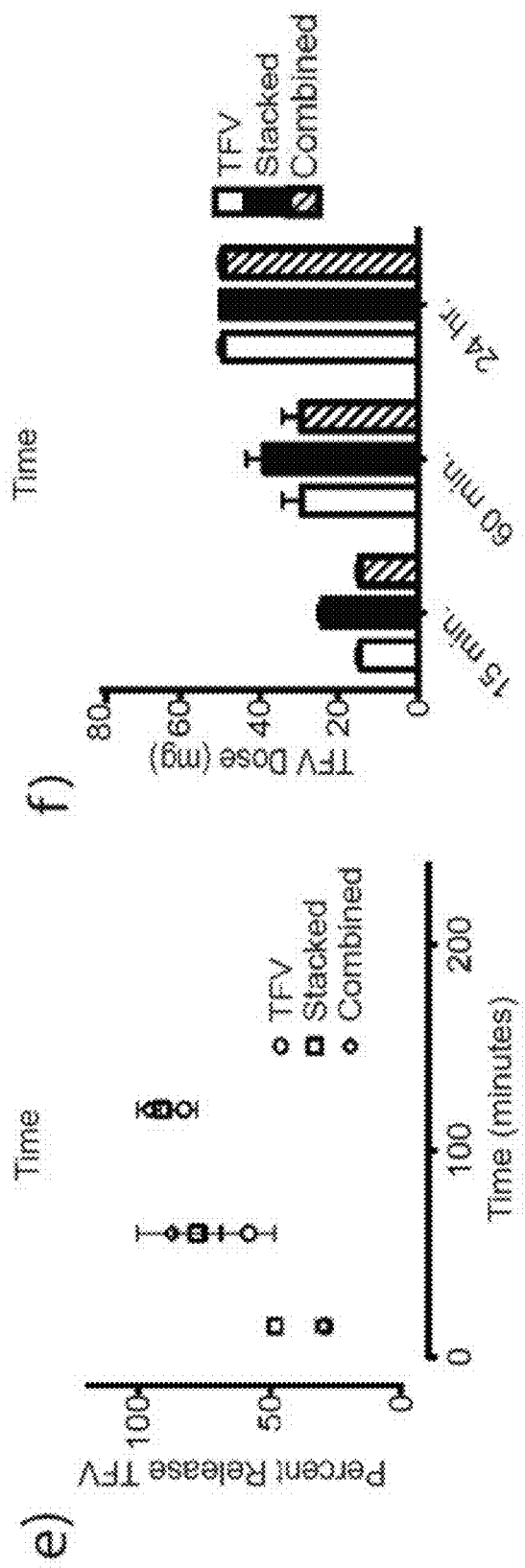

The role of the composite microarchitectures, and effects of drug loading and fabric thickness on release of TFV and LNG in vitro are of great interest. In particular, TFV and LNG are physicochemically different, and initial experiments characterize the release of the drugs individually. TFV or LNG are fabricated at the same 20 wt. % theoretical drug loading to compare the effect of hydrophilic and hydrophobic drug release from PVA fibers (FIG. 12 *a*,*b*). Actual drug loading is roughly equal for the two drugs, with LNG at 16.7% and TFV at 14.3%, but LNG displays much slower release kinetics. TFV reaches 100% release within 30 minutes whereas LNG does not reach 100% release until 240 minutes. The difference in release is reflected also in the cumulative mass of drug released, with ~40 mg of TFV and ~20 mg of LNG released after 15 minutes, and ~60 mg of TFV and ~40 mg of LNG released after 60 minutes. The significant difference in release can be attributed to the highly hydrophobic nature of the fabrics containing LNG, which take longer to wet and dissolve in the release media.

Example 17

Effect of Microarchitecture on Release Kinetics

One can also compare release of TFV and LNG from the three distinct composite microarchitectures and compare the release kinetics to PVA fabrics loaded with TFV- or LNG-only fabrics as a control.

TFV release is similar between the control, stacked and interwoven microarchitectures, where ~50% TFV release after 5 minutes and 100% release after 30 minutes can be observed. In contrast, TFV release from the combined microarchitecture is much slower, with ~50% TFV release after 30 minutes and 100% release after 60 minutes (FIG.

12a), which is also reflected in the lower delivered dose of TFV (FIG. 12c). TFV percentage release is significantly less from the combined microarchitecture, as compared to the TFV, stacked and interwoven microarchitectures, at 5, 15 and 30 minutes ($p<0.05$).

LNG release is the same for all microarchitectures, and showed complete release within 240 minutes (FIG. 12a,d). When comparing the TFV only and combined fabrics directly, the TFV loading is identical (14.3 wt. %) and the only difference between these two systems in the presence of LNG, which was loaded into the same fibers as TFV. The combined fabric had two-fold slower release of TFV than the TFV only fabric (FIG. 12c). Therefore, it appears that the presence of LNG in the fibers is responsible for the observed change in TFV release. Comparison of TFV release from interwoven and combined microarchitectures also supports this conclusion. Interwoven fabrics have lower TFV loading (4 wt. %), but similar LNG loading to the combined fabric (12 wt. %). Despite the similar LNG loading but greater than four-fold difference in TFV loading, both fabrics exhibited similar percent release to the TFV only fabrics. Based on these results, it appears that that the separate LNG fibers did not affect TFV release, and that the microarchitecture plays a role in TFV release from electrospun fabrics.

Example 18

Effect of Drug Loading on Release Kinetics

One can also prepare PVA fabrics containing relative loadings of TFV to LNG of 2000 to 1 to characterize drug release from these materials. This ratio (TFV:LNG=2000:1) is better representative of the dosing requirements of these two drugs and allows testing of whether decreased LNG loading reduces the hindered release of TFV that is described. Indeed, the combined microarchitecture with this ratio had similar TFV release to the TFV control or stacked microarchitecture, with all three achieving 100% release after 120 minutes (FIG. 12e,5f). Compared to the fabrics with 2000:1 TFV to LNG ratio, fabrics loaded with equal TFV to LNG ratios of all microarchitectures released TFV at a slightly slower rate (FIG. 12c, f).

Example 19

Effect of Fiber Thickness on Release Kinetics

Figure 13:
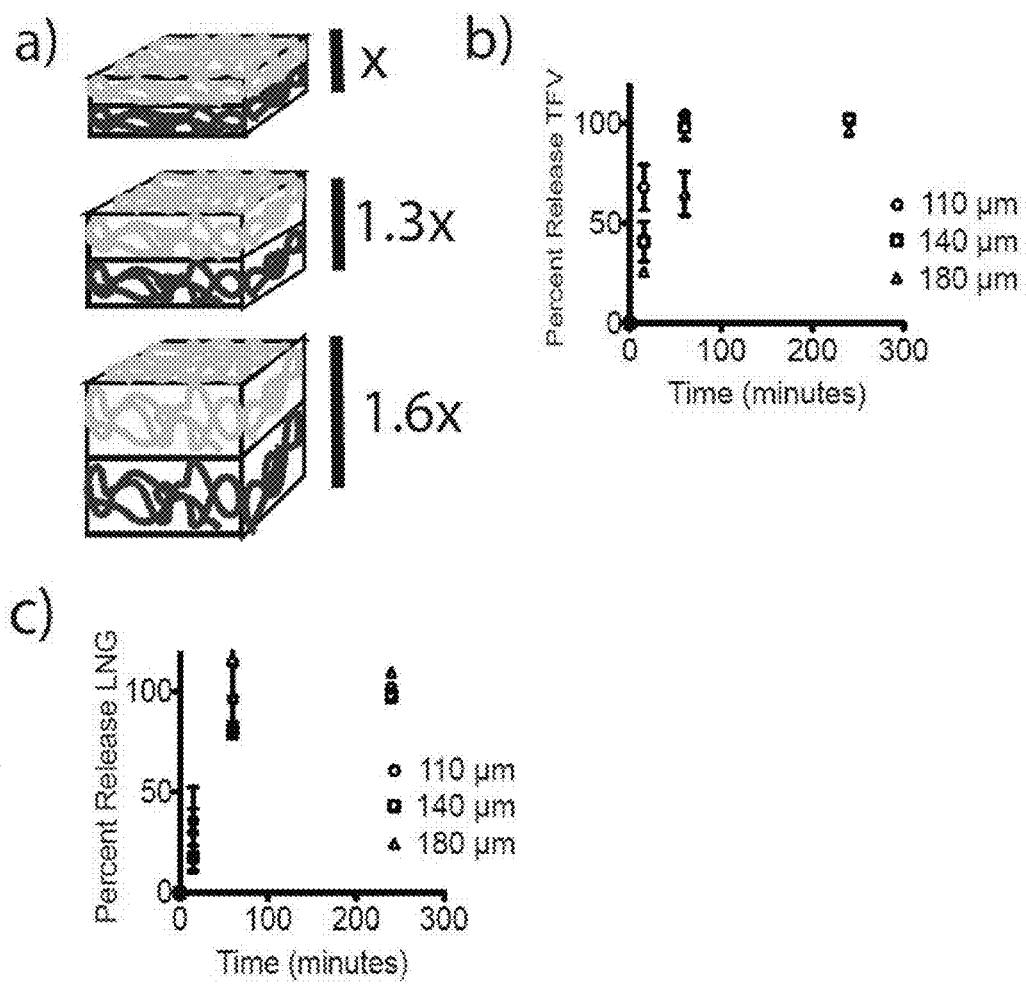
FIG. 13. Effect of LNG and TFV release from stacked composites of different thickness. (a) Schematic of stacked composite fibers with increasing thicknesses, (b-c) in vitro release profiles of TFV and LNG, respectively, from stacked composite fibers of varying thickness.
Figure 14:
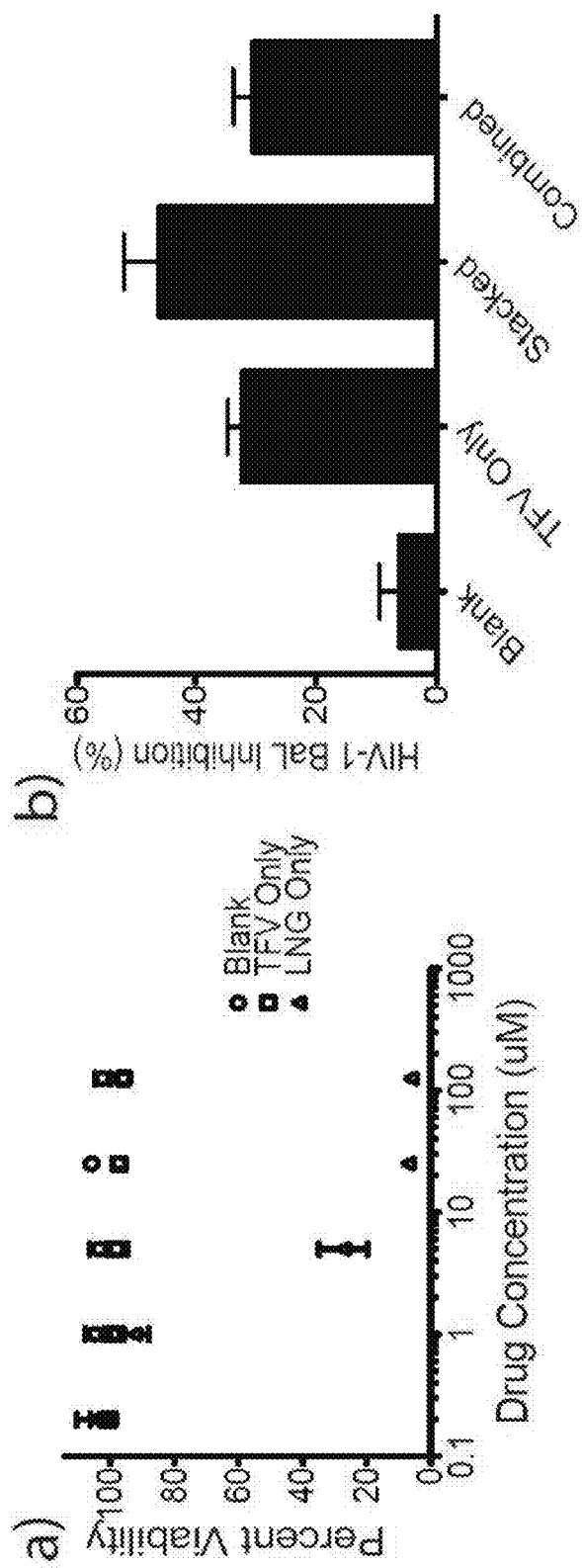
FIG. 14. Cytotoxicity and HIV antiviral activity of drug-loaded fabrics of varying microarchitecture. (a) Cytotoxicity of blank, TFV-only and LNG-only fabrics in TZM-bl cells. (b) Inhibition of HIV-1 BaL infection of TZM-bl cells by blank, TFV-only, stacked and combined fibers at a delivered TFV concentration of 1 µM (IC50 of free TFV was 1.8 µM). Due to toxicity observed for LNG, fabrics with TFV:LNG ratio of 2000:1 were used for testing antiviral activity. Blank fibers were tested based on equivalent polymer concentrations used for TFV only fabrics. Values are reported as mean±standard deviation for n=3.
Figure 15:
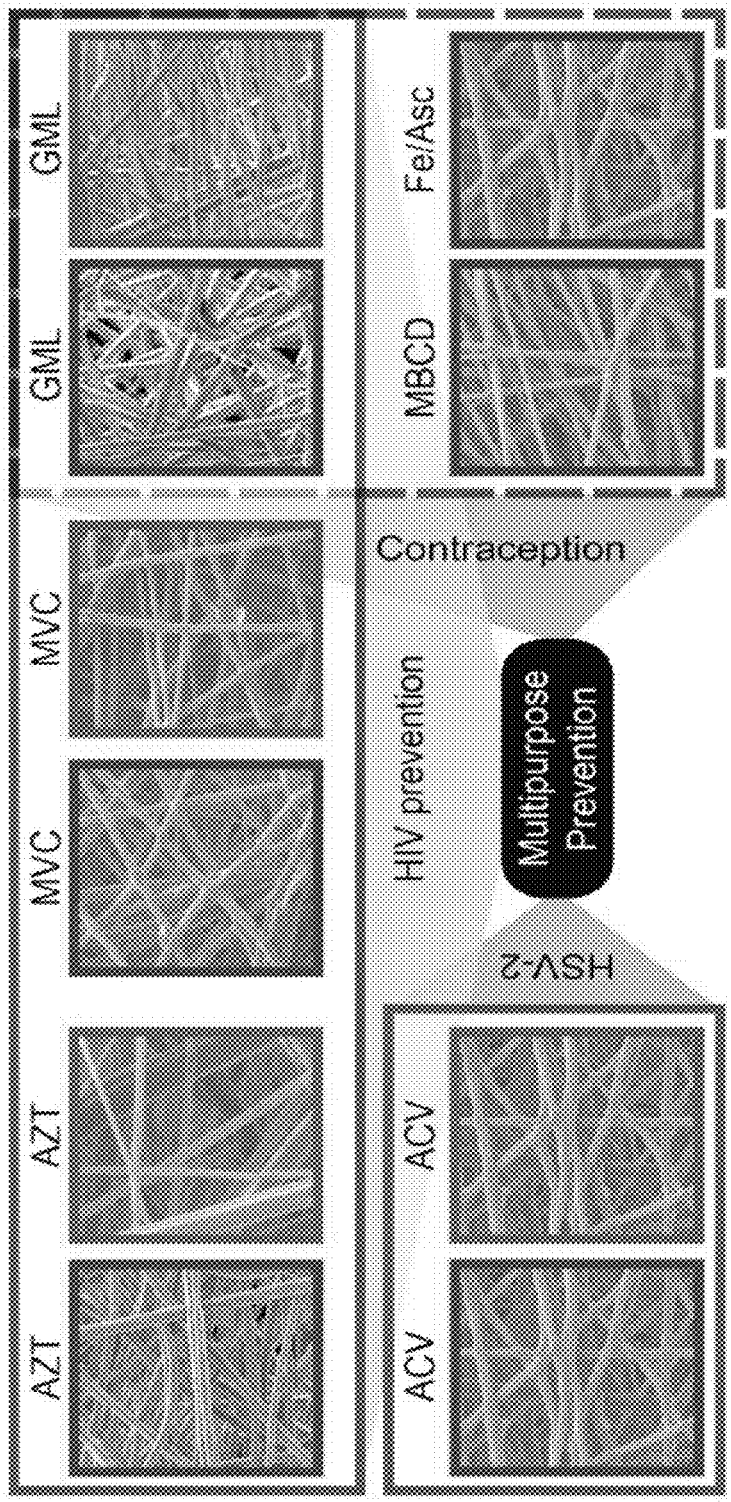
FIG. 15. Drug eluting fibers for multipurpose prevention of HIV, other STIs and unintended pregnancy. (a) Agents with activity against HIV, HSV-2, or sperm were incorporated into PLLA/PEO fibers (PLLA/PEO: 30:70, blue; 70:30, red). (b) Maraviroc release from fibers of different diameter (1,2), hydrophilicity (3-6), and PLA crystallinity (7-10). (c) Dose-response assay indicates that AZT and MVC released from fibers have similar potency to unformulated drug (neat drug=filled, drug eluates=open).
Figure 15:
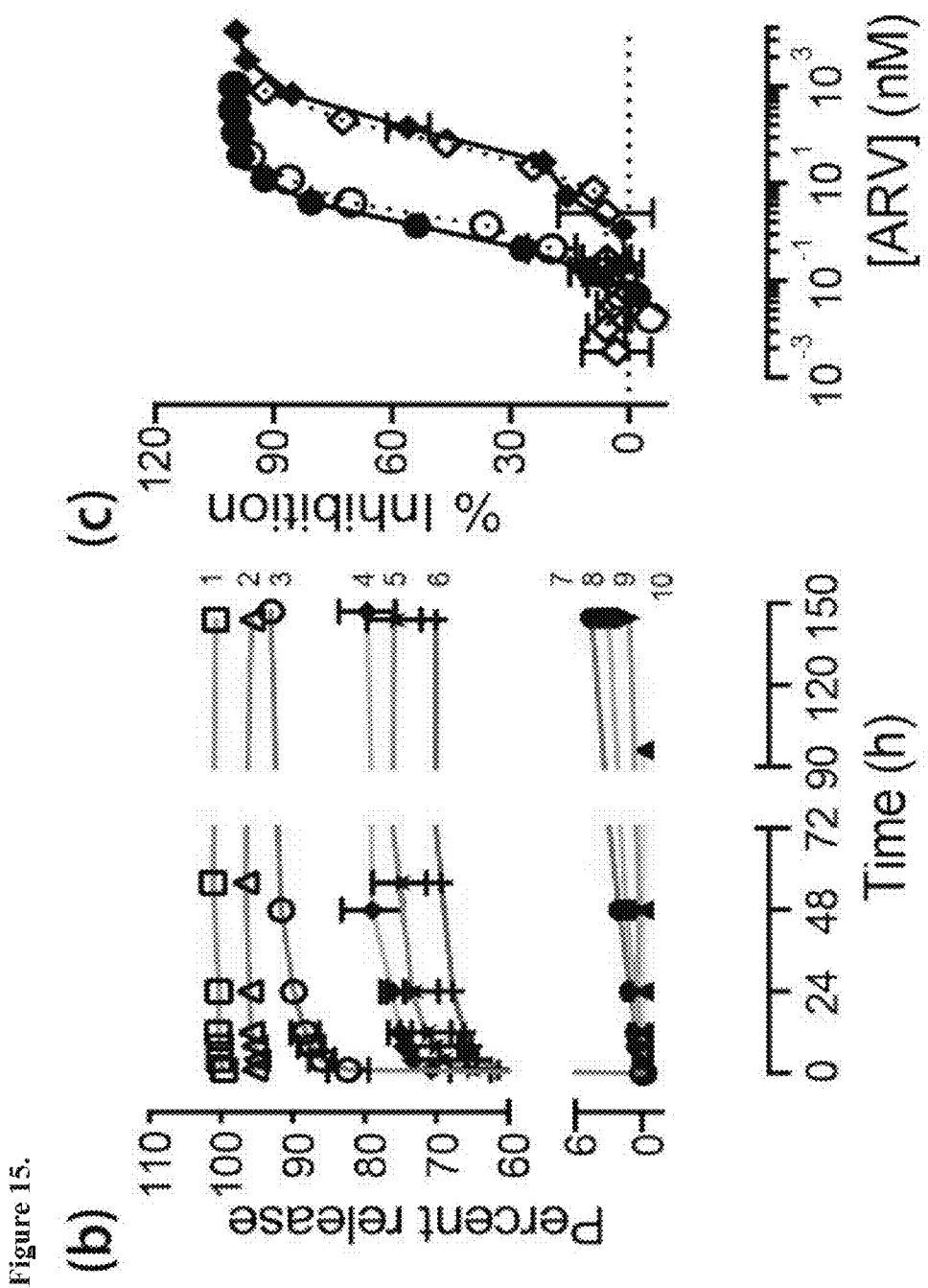

As it is believed that increasing the thickness of electrospun fiber fabrics can slow the release of a single agent, one can investigate how increasing the thickness of electrospun fiber fabrics containing dual, physicochemically diverse agents affects the release of both drugs. Using the stacked microarchitecture, one can prepare three different thicknesses ranging from 110 µm to 180 µm (FIG. 13a). As it is believed that increasing the thickness of the fabrics would slow drug release by increasing the distance required for drug diffusion and increasing wetting time for thicker mats, it is observed that the stacked microarchitecture does not affect release of TFV nor LNG, compared to single drug architecture. Thus, one can assess mat thickness as an independent variable. Consistent with that observation, TFV release is slowest from the thickest fiber fabrics (180 µm), with ~50% release after 60 minutes and 100% release after 240 minutes, while the thinnest fiber fabrics (110 µm) released ~50% within 15 minutes and 100% release after 60 minutes (FIG. 13b). LNG release is not dependent on thickness, probably due to the dominance of its hydrophobicity over the effects of altering physical properties of the fabrics.

The release of TFV from composite electrospun fabrics can be manipulated by changing the microarchitecture, the relative loading of LNG and TFV within the composite microarchitecture, or the thickness of the fabric. In contrast, release of LNG is unchanged by modulating microarchitecture, loading and fabric thickness. These factors play an important role in the development of topical delivery of dual agents from electrospun fabrics.

Example 20

In Vitro Cytotoxicity and Inhibition of HIV-1 BaL Infection

The activity and toxicity of PVA, LNG only, TFV only, stacked and combined fabrics is evaluated using in vitro assays. Drug eluates from fibers dissolved for 24 h in cell-culture media are used to perform the assays. PVA and TFV only fabrics re found to be non-toxic to TZM-bl cells at all concentrations tested. Fabrics containing LNG are toxic at concentrations of 5 µM LNG and higher. The cytotoxicity studies are performed using the fabrics with theoretically equal loadings of TFV and LNG (at 20 wt. % each). Based on these results and the more clinically relevant dosing, activity is assessed using fabrics with the lower loading of LNG (0.0067 wt. %). TFV only, stacked and combined fabrics had IC50 values of 2.2, 1.7 and 2.9 µM TFV, respectively. There is no statistically significant differences in antiviral activity between the fabrics of varying microarchitectures, or between the free drug, which has an IC50 of 1.8 µM, as reported previously. It is observed that LNG-only fabrics inhibited HIV infection at the highest concentrations, which may be associated with the toxicity seen at high doses of LNG, as LNG is not known to have any antiretroviral activity. Activity of TFV is preserved through the electrospinning process and did not depend on composite geometry.

Example 21

Discussion

As described herein, composite fibers containing TFV and LNG of three distinct microarchitectures by free-surface electrospinning can be produced using a production-scale instrument. Variable parameters, such as drug loading, composite microarchitecture and fabric thickness do affect in vitro release of TFV, but not LNG. The pharmacological activity of TFV can be preserved through the electrospinning process and is not hindered by combination with LNG.

The fabrics in these studies were prepared on a production-scale electrospinning instrument, the Elmarco NS 1WS500U, and this is the first instance of producing combination drug-eluting fibers on a scaled-up process using a free-surface, production-scale instrument. Furthermore, high drug loading (up to 20 wt. %) does not negatively impact productivity. Likewise, these are the first descried results for producing a composite fabric with the different microarchitectures using a large-scale instrument. Although the fabrics have distinct composite geometries (FIG. 11), the fiber mats were macroscopically indistinguishable. This is an important aspect for user perception as it is valuable to be able to incorporate drugs without changing the visual and tactile properties of the fibers. The inability to distinguish between fibers also adds another level of discretion for the user, as the fiber could contain solely an antiretroviral or contraceptive, or both, without being able to tell the difference visually. The ability to vary the microstructure on a production scale instrument may also prove to be useful in a number of drug delivery applications.

Only minimal amounts of crystalline drug are detected using DSC (FIG. 10), suggesting that most of the drugs exists in an amorphous state, even at high loading. The detection of crystalline drug at higher loadings of LNG indicates that there may be a potential threshold loading value that leads to crystalline drug in the fibers. This may also be true for TFV as only the fibers with higher TFV loading, including the TFV only, stacked and combined microarchitectures, had detectable TFV crystallinity. Alternatively, it is possible that the amount of drug, be it crystalline or amorphous, in the fibers is below the limit of detection for the drugs on the DSC. Interactions between the TFV and polymer may cause the PVA to adopt a distinct polymorph compared with the pure PVA fibers. The shift in Tg may be due to the greater potential of PVA to hydrogen bond with TFV as compared to LNG, based on the number of hydrogen bond donating and accepting sites on the molecule.

Combination drug delivery remains a challenge as there is still little known about co-delivery and interactions between physicochemically diverse drugs when delivered from a single device. By combining a highly hydrophobic contraceptive, LNG, and a hydrophilic antiretroviral drug, TFV, it is observed that the relative drug loading, composite microarchitecture and fabric thickness affect release of both agents. The release of TFV from fabrics of varied loading and microarchitecture (FIG. 12a,e) differed, but interestingly not in the release of the more hydrophobic LNG (FIG. 12b). Slower release of TFV is seen with increasing fabric thickness likely correlates to hindered release due to slower wetting and increased distance for drug diffusion of the fiber matrix. In contrast, the release of LNG is largely unchanged by the microarchitecture and fabric thickness. The hydrophobicity and wettability of the fabric is the apparent limiting factor in release. Without being bound by any particular theory, one expects that the added hydrophobicity from the LNG to the fibers governs release, as the TFV release was affected by LNG presence in the same fiber.

For example, FIG. 12a shows that when TFV is loaded into PVA fibers with an equal amount of LNG, release is two-fold slower as compared to release of TFV when loaded into PVA fibers alone. The amount of LNG in these fibers is much greater than the combined fibers shown in FIG. 12e, making them more hydrophobic and slower to release. Though one observes differences in release kinetics depending on microarchitecture and co-delivery of multiple agents, there is no impact from these factors on activity. Thus, in designing co-delivery devices, it is important to consider the impact of design on release kinetics, but not necessarily the activity. It is likely that combinations of drugs that are not physicochemically diverse, such as two hydrophobic drugs or two hydrophilic drugs, would be less susceptible to the slowed release kinetics seen in combined composite microarchitecture and high relative drug loading, but may still be affected by increases in fabric thickness.

The composite microarchitectures utilized in these experiments can be used to tailor release for different types of delivery. The stacked composite could potentially be used to asynchronously deliver drugs in the vaginal or rectal mucosal environment by applying the layer with desired quicker delivery directly to the vaginal lumen. This may be useful in a prophylaxis setting when delivering two antiretrovirals with different mechanisms of action that may require different timing based on drug half-life, such as tenofovir, a nucleotide reverse transcriptase inhibitor, and raltegravir, an integrase inhibitor. The combined microarchitecture has the advantage of manufacturing ease, as only one solution is prepared and spun. However the individual drug release properties can be altered when combined in the same fiber, as observed in these studies. Assuming that more symmetric loading is achievable for the interwoven fabric than we observed, this microarchitecture would provide spatially equal distribution within the mucosal environment, while leaving release kinetics of individual drugs unaltered from potential effects of combining them within the same fiber.

Example 22

Conclusions

A production-scale Elmarco NS 1WS500U was used to prepare drug-eluting PVA fibers in novel microarchitectures, including stacked, interwoven and combined composites. The fibers were loaded with LNG and/or TFV, two physicochemically diverse drugs without affecting electrospinning productivity. The resulting electrospun fabrics were macroscopically indistinguishable despite confirmation using confocal microscopy that the micro-scale geometries were unique. In vitro release kinetics of LNG were unaffected by co-delivery with TFV in any of the microarchitectures and increasing fabric thickness. However, TFV release kinetics were slowed when TFV was combined in the same fibers as LNG, and when the thickness of the fabric was increased. This work implicates the importance of considering the microarchitecture and drug properties when designing composite drug-eluting electrospun fibers. These contraceptive microbicidal electrospun fabrics are a promising new vehicle for multipurpose prevention.

Example 23

Extendibility of Electrospun Composite Fibers for Different Applications

Figure 16:
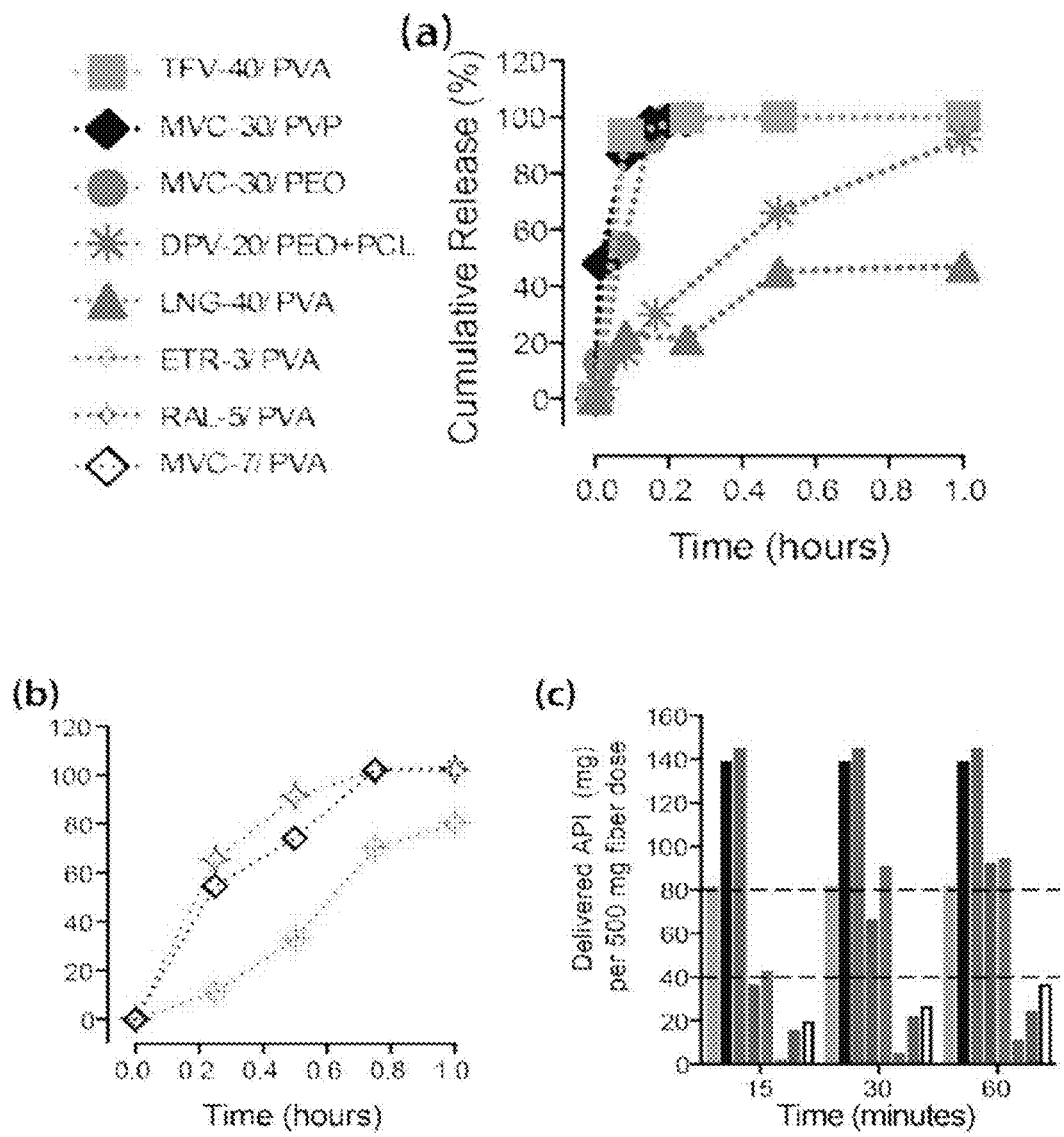
FIG. 16. Pericoital fibers for combination API delivery. Hydrophilic polymers and blends are prioritized for rapid release (<20 min) of the drug payload from fiber fabrics. (a) Release kinetics of physico-chemically diverse ARV drugs (TFV, MVC, DPV) and chemical contraceptives at different loadings from hydrophilic polymer fibers PVA, PEO, PVP, and PCL blends with PEO. (b) Release kinetics of ETR-, RAL-, and MVC-fibers loaded at 3, 5, and 7 wt %, respectively in PVA fibers. (c) A single fiber fabric dosed at 500 mg will deliver a target dose of 40-80 mg ARV drug at 30 min if loaded at >10 wt %.
Figure 17:
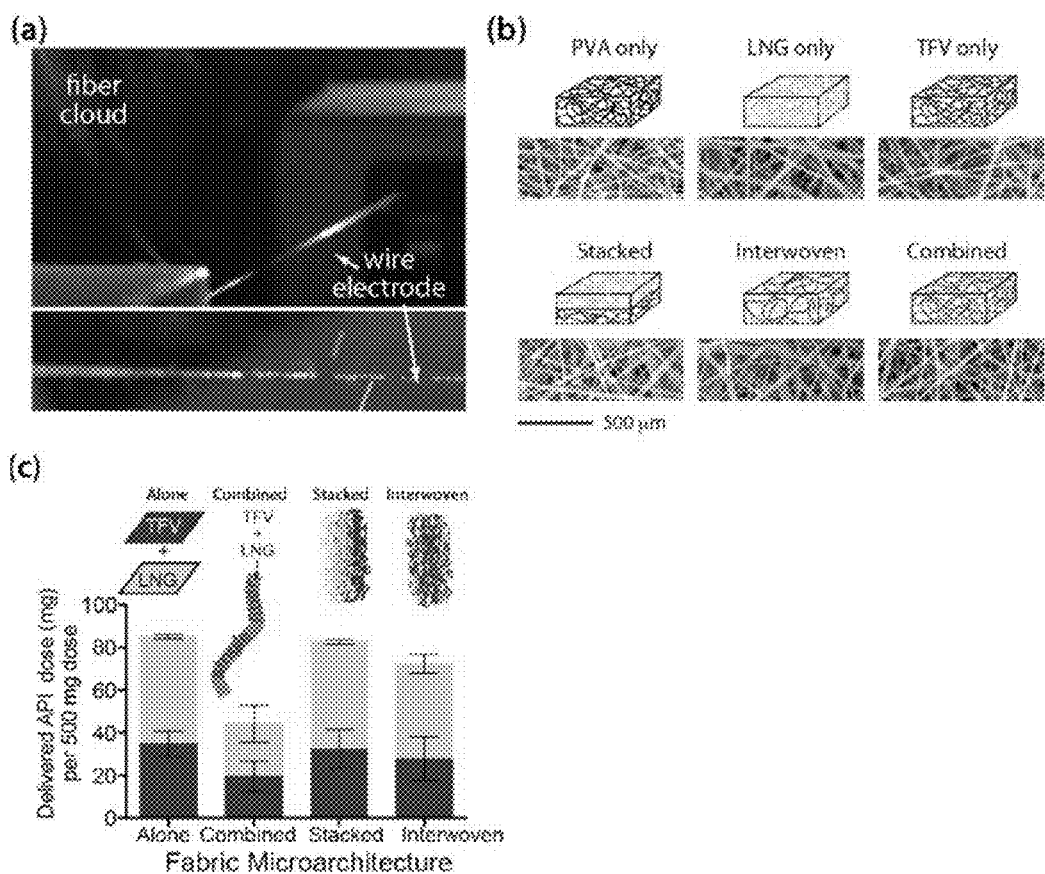
FIG. 17. Scale-up synthesis and fabric microarchitecture for combination ARV delivery. (a) Scale-up electrospinning using the NS1WS500U (Elmarco, Inc.) equipped with a wire electrode. (b) Fabric microarchitectures attainable for composite materials to deliver drug combinations. (c) Effect of microarchitecture on the release of API drug release. Fabrics that combine the APIs in a single fiber show altered drug release dosing compared to when APIs are separated.
Figure 18:
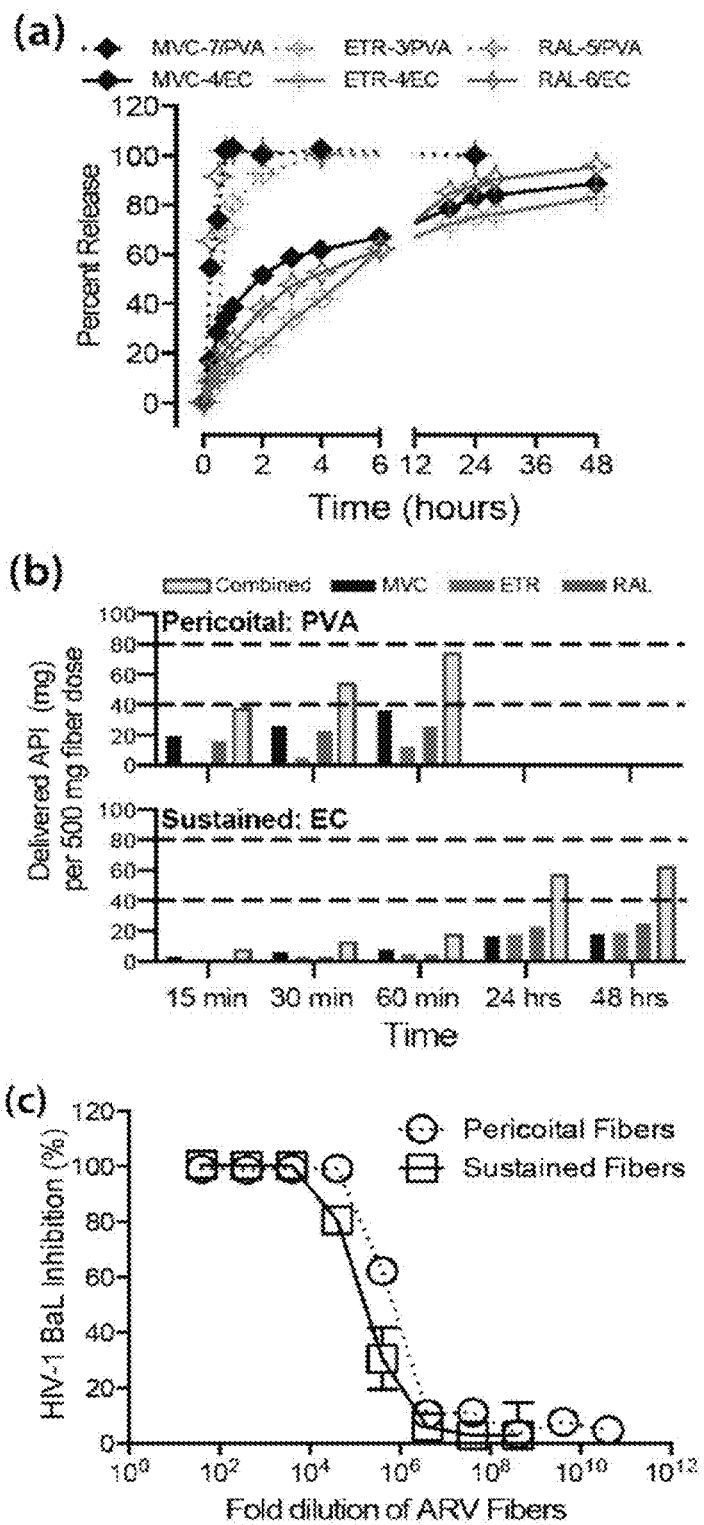
FIG. 18. Sustained fibers for combination ARV delivery. (a) Rapid and sustained release of MVC, ETR and RAL loaded at ~5 wt % from either PVA or EC fibers. PVA fibers rapidly burst release the ARVs whereas EC fibers sustain drug release up to 2 d. (b) Total ARV is delivered at the target dose for both pericoital and sustained fibers. Increased loading of single ARVs will deliver target doses for the individual drugs. Composite materials should provide targeting dosing over the entire time range. (c) ARV drugs released from both PVA or EC fibers inhibit HIV-1 BaL infection of TZM-bl cells in vitro. Final ARV drug concentration at IC50 for ETR, MVC and RAL was 0.7, 1,6, and 1.2 nM (pericoital) and 2.7, 4.2, and 3.8 nM (sustained), respectively.

As the described results demonstrate the application of electrospun fibers for delivering combinations of physicochemically diverse drugs, such as an antiretroviral drugs and non-hormonal chemical contraceptives to inhibit HIV-1 infection and sperm function, in vitro, it is clear that hydrophilic and/or hydrophobic polymers can be delivered from fibers, and of interest is extendibility for drugs with a range of aqueous solubility and partition coefficients. Examples include maraviroc, azidothymidine, acyclovir, tenofovir, dapivirine, raltegravir, etravirine and the hormonal contraceptive, levonorgestrel. Importantly, despite the differences in drug physico-chemical properties, all drugs were fully incorporated into the fibers with encapsulation efficiencies >95%, and one can further efficiently incorporate of cyclic sugars (cylodextrin), inorganic salts (iron gluconate), and fatty acid esters (GML) into fibers based on the same polymer blend of poly lactic acid ("PLLA") and/or poly ethylene oxide ("PEO"). Prototype fibers containing up to 60 wt % drug for tenofovir, dapivirine, raltegravir, etravirine and the hormonal contraceptive levonorgestrel have been produced using the described methods (FIGS. 16-18). These results show polymer fibers can provide a single dosage form that is amenable to encapsulating an array of small molecule hydrophobic and hydrophilic compounds In addition, delivery of drug combinations either from fibers containing multiple drugs or from composite fiber materials made from stacked or interwoven fibers containing individual drugs can be made using the described techniques. In all instances, fiber-based dosage form for combination drug delivery can provide rapid and sustained drug release over several minutes to multiple days. For example, hydrophilic and hydrophobic drugs are rapidly delivered from small diameter fibers.

Example 24

Extendibility of Electrospun Composite Fibers for Different Applications

Further modulation of drug release can be achieved within the same PLLA/PEO polymer blends. Using maraviroc ("MVC") as a model drug and testing effects on drug release by changing fiber diameter, hydrophilicity (PEO content), and polymer crystallinity, it is observed that increasing fiber diameter up to 6× correlated with reduced amounts of MVC released after 6 days (FIG. 16). Reducing the amount of PEO in fibers to 1% (99:1 PLLA/PEO) eliminates MVC burst release and reduces overall MVC release to <2% of total encapsulated drug content after 6 d. In these cases, the drug release appeared to be determined largely by the rate of PEO hydration and the degree to which the drug partitioned into the hydrophilic or hydrophobic polymers, thereby providing a high degree of adaptability in establishing and modulating a particular drug release profile.

In addition, one can exploit the semi-crystalline structure of PLLA occluded water penetration into hydrophobic regions of the blended fibers to prevent MVC release. It is observed that blending a lower molecular weight and amorphous PDLLA with PLLA establishes the resulting material asable to release MVC linearly over 6 days in amounts up to 5% of encapsulated MVC (FIG. 16). Such results can also be applied to achieve sustained drug release from other polymers including polyvinyl alcohol (PVA) and cellulose (FIG. 16-18). In conclusion, we provide strong preliminary data to support the feasibility of achieving pericoital (short-term) and sustained drug release from polymer fibers. Examples of various fibers produced by the described methods are provided in Supplementary Table 5.

Example 25

Electrospun Composite Fibers for Multi-Drug Cocktails

Antitretroviral cocktails, such as with maraviroc ("MVC"), etravirine ("ETR"), and raltegravir ("RAL") triple ARV cocktail are predicted to be sufficiently effective to halt viral replication, which is an important target in the design of drug agents for treatment. In consideration of both the chemical properties of these different drug agents, and the desires of end users to promote adherence, a range of material properties and physicochemical/rheological performance characteristics are deployed. Prototypes for assessing user perception can represent variations in 4 form properties, resulting in 8 original prototypes: geometry (square/rectangular or hollow tube), texture (textured or silky), dissolution time (short, long), and dissolution viscosity (low, high). Other fiber fabric variations of rectangular or tube geometry can be made by altering the substrate containing the collected fibrous material, as to specific dimensions or rolled and sealed into a hollow tube. Fiber fabrics of different textures can be obtained by varying the texture of the collecting substrate. Finally, for fabricating fiber prototypes with varying dissolution times and viscosities, one can vary the composition of the electrospun polymer or the presence of several different excipients approved for oral and topical drug formulations (e.g., fillers, binders, disintegrants). As described, certain materials already demonstrate target ARV loading and release kinetics and these materials can be the focus of manufacturing at larger scale. The described results demonstrate the versatility of polymer fibers for rapid and sustained delivery of diverse ARVs alone and in combination to fabricate composite materials of varying microstructure, and to be manufactured using an industrial-scale electrospinning process. Such an approach can guide the development of sustained-release fibers for combination ARV delivery, in which a chief aim is adjustment of rapid or sustained drug release through control of drug dispersion within select hydrophilic and hydrophobic polymers. In all instances, critical parameters include identification of the impacts of drug polymer interactions and polymer erosion, degradation on safety and outcomes. Ultimately, such parameters can establish a design for safe, quick-(<30 min) and sustained-(up to 7 d) release of a combination of drugs, such as ARVs, with persistent drug concentrations within tissues (>$10^3$ ng/g).

Example 26

Electrospun Composite Fiber Materials

Various composite fiber fabrics can be applied in the described systems and methods, but any material selected must meet minimum target product specifications for drug loading and in vitro release, chemical and functional identity of the released drugs, and physical and stability constraints for the final fiber formulation. Along these lines, a number of hydrophilic materials, such as PVA, PEO, Polyvinylpyrrolidone ("PVP"), and hydrophobic materials such as ethyl cellulose ("EC"), Eudragit®, polyurethane ("PU") polymers that are generally regarded as safe by the FDA.

In brief, assessing polymer performance begins with dissolution in a suitable volume of solvent to obtain solution properties conducive to electrospinning Various drug agents, such as ARVs, can be dissolved directly into the same solvent or a co-solvent that is miscible with the polymer solvent. The ternary mixture (drug-polymer-solvent) is be electrospun using the described techniques to fabricate fiber fabrics that deliver the triple ARV drug cocktail. Fiber fabrics are electrospun on a NS Lab 500 (Elmarco, Ltd.), a scale-up instrument that implements free-surface electrospinning using a wire electrode.

Certain design specifications that could be desirable for multiple drug agent delivery, such as combination ARV drug agents, include drug loading (>10 wt %), drug release kinetics (40-80 mg·d-l per API over 10 min-7 d), and other criterion defining the vehicle features, mechanical/rheological, disintegration, dispersion pH and osmolarity, and stability. As related to these characteristics, one can use UV-HPLC, measure drug loading and characterize the solid dispersions. In vitro release from the fibers can be assessed on a USP IV flow-through dissolution apparatus (CE7 Smart USP4, Sotax) at 37° C. for up to 7 d in sink conditions. Image analysis of SEM micrographs of ARV-fibers is used to measure the mean diameter and morphology of the fibers, and the pore size of the meshes. One can also measure vehicle features such as web area weight and fiber mesh thickness. Other measurements of mechanical properties (tensile strength, elasticity, bioadhesive strength) of dry and hydrated fiber meshes can be performed using a dual-column tabletop universal testing machine (UTM 3365, Instron), and viscosity of hydrated fiber meshes using a rheometer.

Example 27

In Vivo Safety and Pharmacokinetics of Multi-Drug Cocktail Fibers

Safety and pharmacokinetics of multi-drug combination fibers can be evaluated in a variety of parallel studies. In each study, the lead fiber microbicides can be tested against a matched placebo control for safety and toxicity. The matched placebo control is defined as the same formulation as the test product without the active components. In a first study, one can evaluate the safety of the drug combination fibers, as follows: half of the subjects can receive placebo fibers and half can receive fibers encapsulating the multi-drug fiber. In cross-over experiments, conducted at least two weeks after the completion of the first study, each group will receive the opposite fiber type. Measurements for colposcopy, vaginal pH, microflora and cytokine analysis are performed. Fiber formulations can be applied daily during the first five consecutive days and again on days 8-11, with swabs (microflora, pH, cytokine) taken prior to and 30 min after each fiber administration. Safety testing of sustained release fibers will be performed in a similar manner except for different dosing times and time points for safety and PK analysis. The diffusion coefficient for small molecule drugs (~$10^{-8}$ cm$^2$·sec$^{-1}$) predicts that they will diffuse a distance of ~0.5 mm in 30 min, and the partition coefficients for these ARV (logD ~2-4, pH 4) predict they will partition into tissues.

Example 28

Electrospun Fibers Incorporate Antiviral Compounds with High Drug Loading

The Inventors adapted the described techniques to produced nanofiber meshes eluting small molecule agents targeting HIV-1, HSV-2, and sperm function. One can electrospin fibers from mixtures of hydrophilic polyethylene oxide ("PEO") and hydrophobic poly-L-lactic acid ("PLLA"), two polymers with proven biocompatibility and FDA approval for use in medical implants. It was found that fibers with partially hydrophilic and partially hydrophobic composition would permit encapsulation of agents with high and low aqueous solubility, respectively. Other studies with PLLA-PEO polymer blends found that blends act as a single material with averaged properties when mixed at a ratio up to 30:70 or 70:30 (wt/wt), but act as a composite of two materials with discrete properties when mixed at ratios approaching 50:50 (wt/wt). To fabricate homogeneous fibers with uniformly blended hydrophilicity/hydrophobicity, the Inventors electrospun 70:30 (wt/wt) PLLA/PEO and 30:70 (wt/wt) PLLA/PEO meshes, and also pure PLLA and pure PEO meshes.

Figure 19:
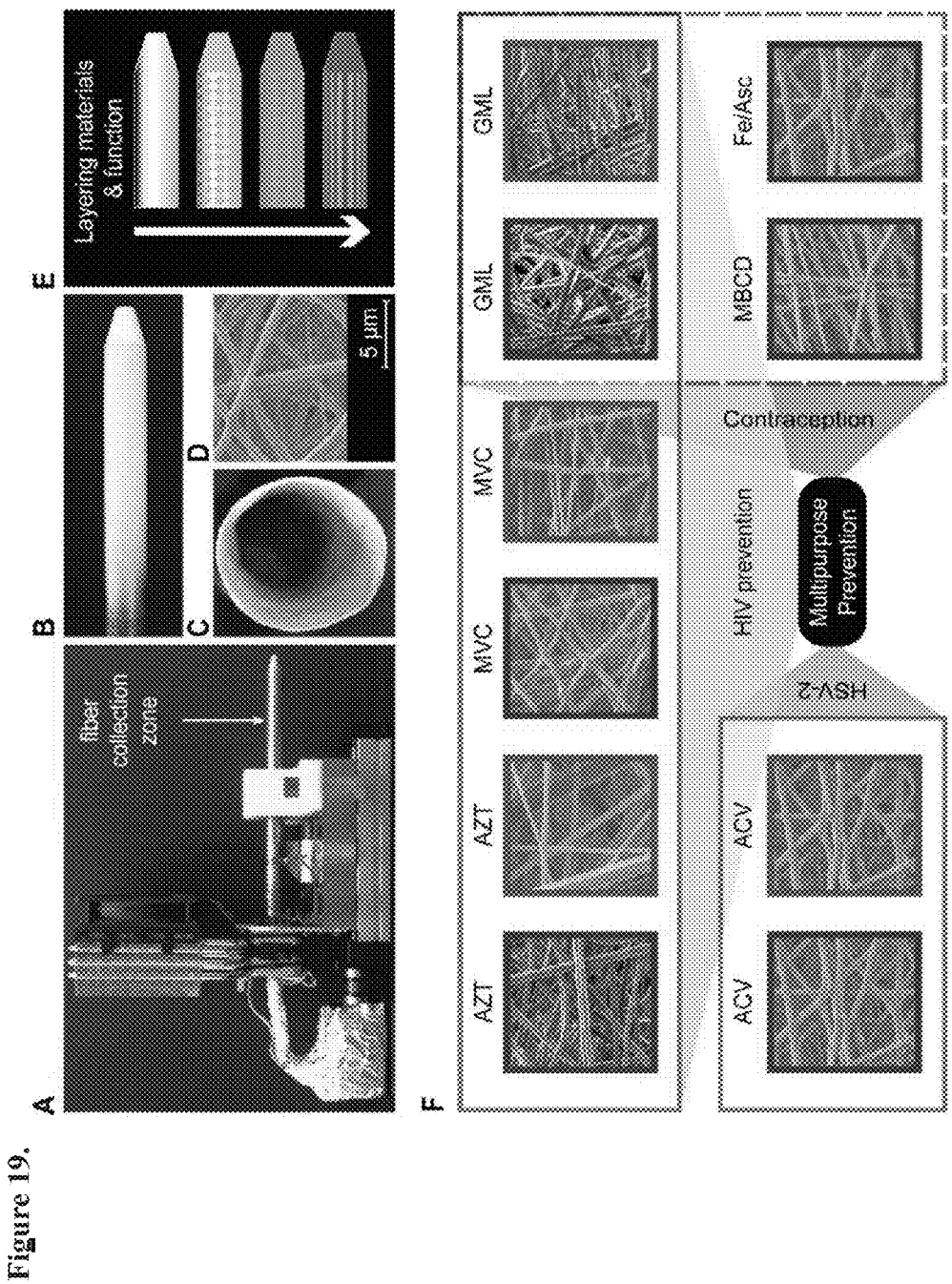
FIG. 19. Electrospun fibers incorporate drugs for multipurpose prevention. (a) Two-axis mandrel electrospinning rig for fiber collection. (b) Controlled fiber deposition along a grounded aluminum collector produces a geometry that may be suitable for vaginal drug delivery. (c) Mesh abstracted from mandrel has a hollow interior. (d) Fiber meshes have porous microstructure. (e) Combining fiber meshes produces a multifunctional material. (f) Diverse agents with action against HIV, HSV-2, or sperm are incorporated into blends of PLLA and PEO. PLLA/PEO (30:70, blue) and PLLA/PEO (70:30, red); AZT=1 wt % 3'-azido-3'-deoxythymidine, MVC=1 wt % maraviroc, ACV=1 wt % acycloguanosine, GML=10 wt % glycerol monolaurate, MBCD=10 wt % methyl-β-cyclodextrin, Fe/Asc=10 wt % iron (II) D-gluconate with 10 wt % ascorbic acid.

Polymer concentration in the electrospinning solution has a significant impact on the resulting fiber diameters between formulations with the same PLLA/PEO ratio and solvent choice, as assessed by ANOVA (P, 0.0001) Electrospinning parameters are modified to yield fibers with reproducible size and high polymer recovery, and two blends are identified for further study: 70:30 PLLA/PEO in 1:1 chloroform/2,2,2-trifluoroethanol and 30:70 PLLA/PEO in 3:1 chloroform/2,2,2-trifluoroethanol. These compositions produced fiber diameters of 200-700 nm and polymer recovery of 0.50% The fibers are collected on a mandrel designed in the geometry of a tampon applicator (FIG. 19a-b) and resulting in fiber meshes in the shape of a hollow tube (FIG. 19c), which can be incorporated into a standard tampon applicator. By controlling the axial deposition of the fibers near the apex of the collector, one can also form a thick barrier mesh (2-3 mm thick) that is continuous with a thinner inner mesh (down to 10 mm thick).

There are several model compounds that can demonstrate the versatility of electrospun fibers to deliver agents with differing solubility and mechanisms of action against either HIV-1 or HSV-2 (FIG. 19f). Fibers containing either 1% (wt/wt) maraviroc (MVC), which inhibits CCR5-mediated HIV fusion, 1% (wt/wt) 39-azido-39-deoxythymidine (AZT), which inhibits viral reverse transcriptase, or 1% (wt/wt) acyclovir (acycloguanosine), which has antiviral activity against HSV-2 were all prepared. Collectively, these compounds vary in aqueous solubility (0.01-50 g/L) and span a wide range of log P values (−1 to 4).

One assesses drug loading of MVC or AZT-loaded fiber meshes stored at room temperature (19-22° C.) for at least five months by dissolving the fibers in acetonitrile and measuring drug content with HPLC. MVC and AZT are incorporated successfully into fibers at 95% drug encapsulation efficiency for both PLLA/PEO blend compositions. ARVs eluted from the polymer fibers were identical to the unformulated drugs as measured by UV-HPLC. This suggests that the compounds are stable during electrospinning and during shelf storage for at least five months. Fiber meshes retained the same white color and soft, flexible texture over five months. While electrospinning did not compromise drug integrity, it is observed that drug incorporation into polymer fibers can influence fiber size, fiber alignment, and polymer recovery.

Example 29

Figure 20:
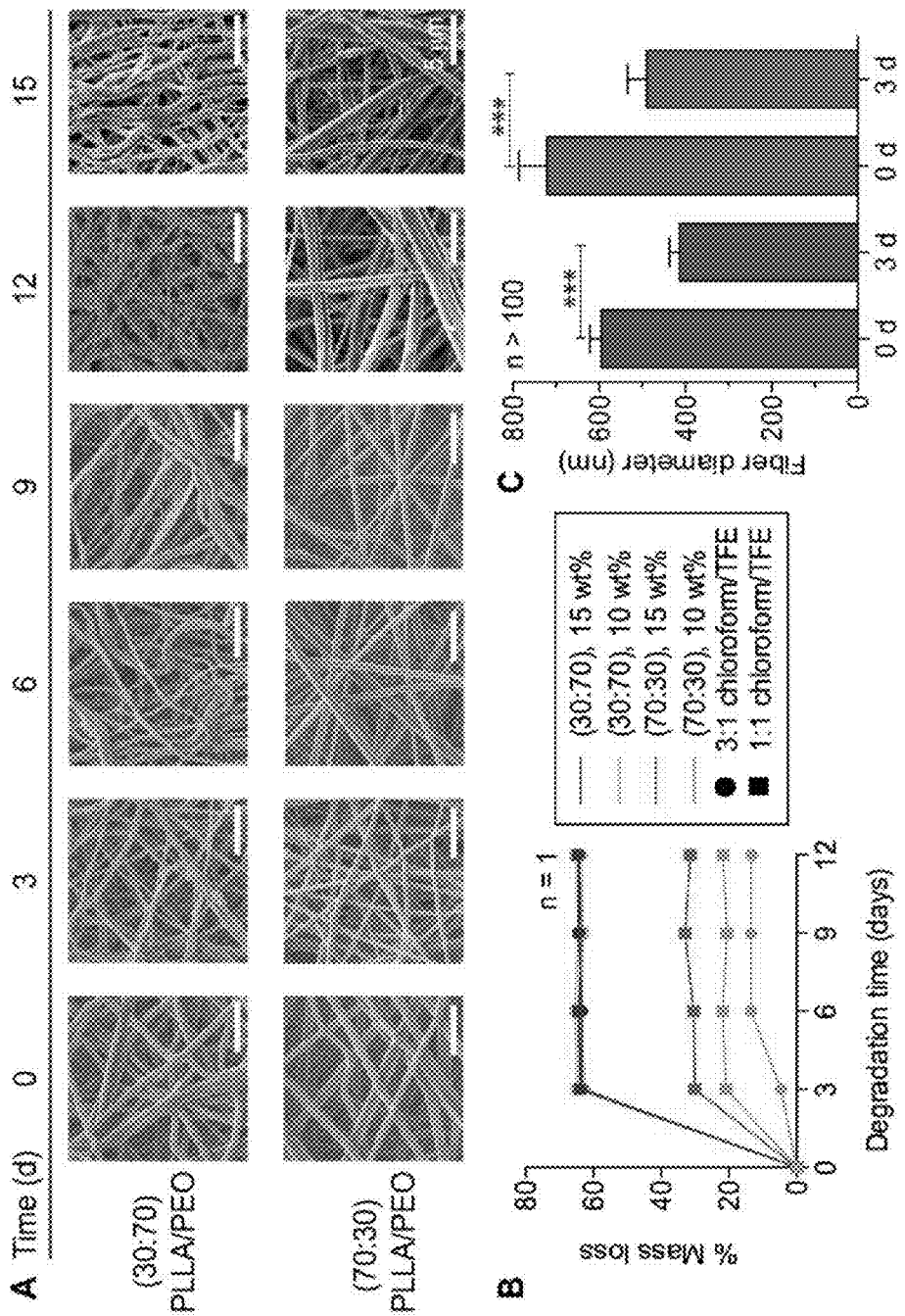
FIG. 20. Fiber composition influences degradation properties. (a) SEM micrographs show that fiber and mesh morphology changes markedly over 15 d in VFS. (b) Mass loss of fibers over time is controlled by PEO content in fibers. (c) Fiber diameters, displayed as geometric mean with 95% confidence interval, and decrease significantly over three days of degradation in VFS (p<0.0001 for 30:70 and 70:30 PLLA/PEO fibers). 30:70 PLLA/PEO (blue) and 70:30 PLLA/PEO (red) for (b) and (c).

Drug-Loaded Fibers Erode and Release Agents to Potently Inhibit HIV-1 Activity In Vitro Sustained drug release over weeks to months has potential for greater adherence whereas burst release of active agents may be desirable for pericoital prevention. Since degradation of polymeric delivery systems can influence drug release properties, one can fabricate fibers with varying degradation rates by modulating the hydrophilic and hydrophobic content of the fibers. Using SEM, one can monitor fiber degradation in VFS over two weeks by recording mass loss and imaging (FIG. 20). Fiber meshes with greater hydrophilic content show the most pronounced change in individual fiber and overall mesh morphology (FIG. 20a). One observes that fibers decrease in diameter within hours to days, and then appeared to fuse into large fiber bundles. These observations re confirmed by measuring a 30% (95% CI=25% to 35%, n=117) reduction in 30:70 PLLA/PEO and a 32% (95% CI=23% to 40%, n=103) reduction in 70:30 PLLA/PEO fiber diameters after 3 days and over 30% mass loss of the meshes within one week (FIG. 20b, c). The percent mass loss corresponded with the percent PEO composition in the fibers (FIG. 20b). Pure PLLA fibers show no mass loss after a one-hour incubation in VFS, whereas pure PEO fibers dissolve in less than 10 minutes upon contact with water.

Figure 21:
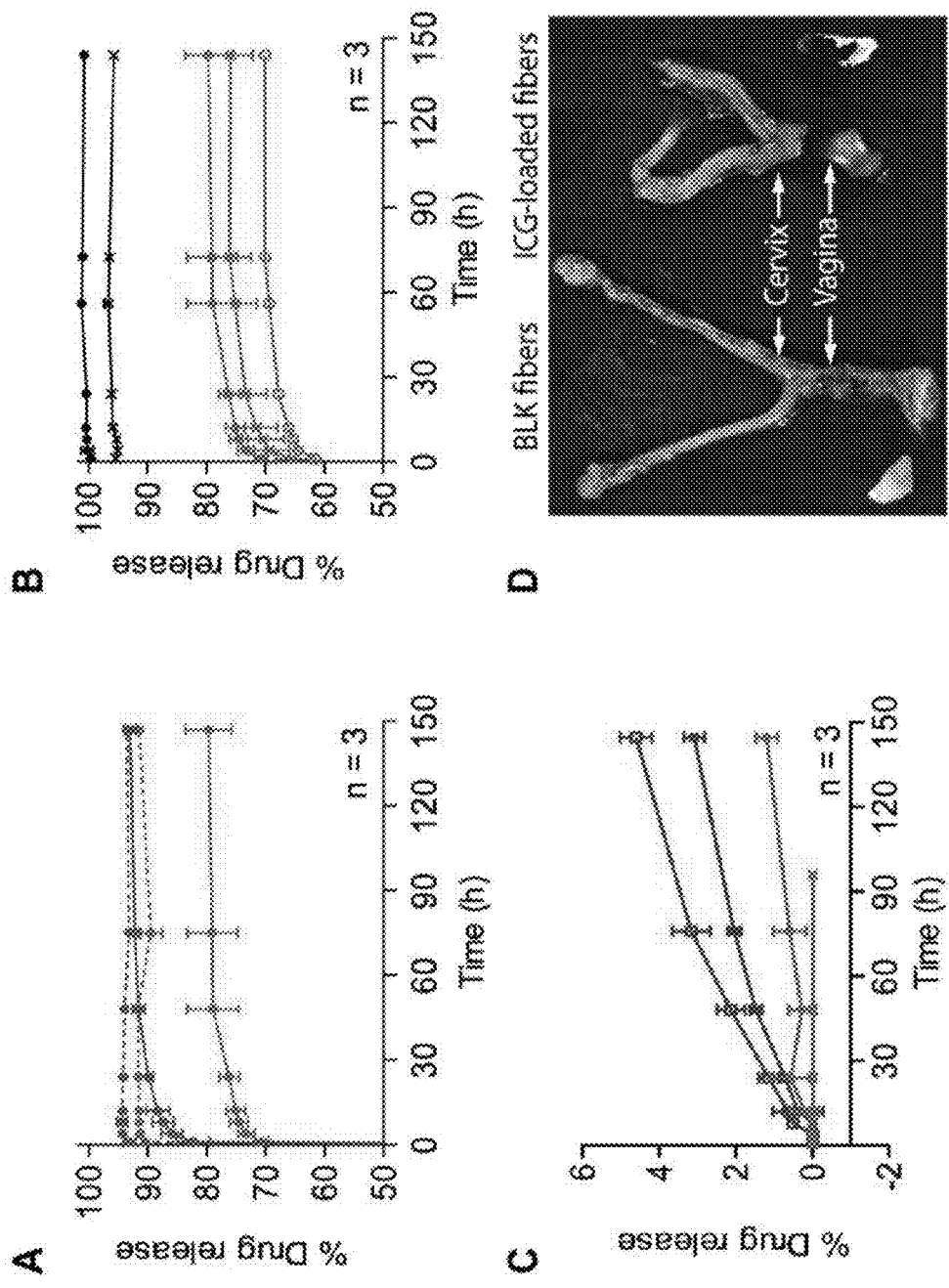
FIG. 21. Fibers release active antiretroviral agents. (a) Cumulative drug release in VFS was measured for 30:70 PLLA/PEO (blue) and 70:30 PLLA/PEO (red). AZT (dashed line) and MVC (solid line) showed rapid burst release from blended fibers within 1 h. (b) Varying fiber diameter resulted in MVC burst release from PCL fibers (black) and 70:30 PLLA/PEO fibers (red). PCL meshes with two fiber diameters (●=370 nm and ⊥=1.3 µm) and 70:30 PLLA/PEO fibers with three fiber diameters (●=560 nm, ○=1.5 µm, ⊥=3.4 µm) were tested. (c) Sustained release of MVC is achieved from PDLLA/PLLA blends and from 99:1 PLLA/PEO, but not from PLLA fibers. 50:50 PDLLA/PLLA (□), 25:75 PDLLA/PLLA (■), 99:1 PLLA/PEO (●), and 100% PLLA (⊥). (d) Insertion of fibers into mouse vagina and subsequent fluorescent imaging reveal release of dye within 30 minutes for ICG-loaded fibers (right) compared with blank fibers (left). Fiber meshes are shown next to excised reproductive tracts.

To investigate if drug release kinetics recapitulated polymer degradation kinetics, the Inventors monitored drug release from meshes incubated in VFS (FIG. 21). It was observed that AZT and MVC burst released from fibers within 1 h, but that the drug release profiles differed based on PLLA and PEO content of the fibers. For example, fibers with greater hydrophilic content (30:70 PLLA/PEO) released 2.1% more AZT (95% CI=0.68% to 3.5%, n=3) and 13% more MVC (95% CI=6.8% to 20%, n=3) over 6 d than corresponding meshes with greater hydrophobic content (70:30 PLLA/PEO) (FIG. 21a). In 6 d, 70:30 PLLA/PEO fibers released 92±.075% of encapsulated AZT and 80±3.9% of MVC into VFS (n=3). The 30:70 PLLA/PEO fibers released 94±.048% of encapsulated AZT and 93±.098% of MVC into VFS (n=3). The Inventors did not detect MVC release from pure PLLA fibers over 96 h in VFS (FIG. 21c). These results suggest that controlling polymer-drug interactions and the rate of polymer swelling and dissolution may alter the release kinetics of different active agents. Given the burst release of AZT and the aqueous solubility of indocyanine green (ICG) dye, the Inventors chose to electrospin ICG-loaded fibers to investigate the extent of fiber coverage and agent release in mice. After inserting 30:70 PLLA/PEO fibers loaded with 1% (wt/wt) ICG into mice, it was observed that dye completely coated the vaginal tract after 30 minutes (FIG. 21d).

These results provide evidence that fibers can sufficiently hydrate and release agents to coat the vaginal mucosa in vivo. Testing multiple strategies to obtain sustained release of MVC from fibers by increasing fiber diameter, reducing hydrophilic polymer content, and modulating PLA crystallinity are each important variations on the production of electrospun fibers. Controlled release of MVC is of interest because it was less hydrophilic than AZT. In different variations on fiber construction, content and design, the effect of increasing fiber diameter to slow release of MVC from 70:30 PLLA/PEO fibers was measured. This included increasing fiber diameters by raising the polymer concentration in 70:30 PLLA/PEO solutions. Despite three- and six-fold increases in fiber diameter, all 70:30 PLLA/PEO fibers burst released MVC within one hour in VFS (FIG. 21b). Comparison of mean MVC release from variably sized 70:30 PLLA/PEO fibers with ANOVA showed that the fibers released significantly different amounts of MVC based on fiber size (P=0.0261). The data suggested a trend for larger fiber diameters to release less MVC into VFS over six days, and 3.4 mm diameter fibers released 9.6% less MVC (95% CI=1.17% to 18.1%, n=3) than 560 nm fibers.

In another variation on fiber construction, content and design is to reduce hydrophilic polymer content by electrospinning fibers from a 99:1 PLLA/PEO blend containing containing 1% (wt/wt) MVC. The resulting fibers are smooth, regular, and similarly sized to 70:30 and 30:70 PLLA/PEO fibers. When placed into VFS, these fibers showed no burst release of MVC. Rather, the fibers provided sustained release over six days, eluting an average of 1.19% of encapsulated MVC into VFS (95% CI=0.51 to 1.88%, n=3) (FIG. 21c).

In an additional variation on fiber construction, content and design Thirdly, we encapsulated 1% (wt/wt) MVC into fiber meshes made from polycaprolactone (PCL) or blends of poly-(D, L)-lactic acid (PDLLA) and PLA to investigate the influence of polymer crystallinity on release rate. PCL is a bioabsorbable hydrophobic polymer with a long history of use in electrospinning PCL has a much lower melting temperature than PLLA, reflecting lower crystallinity and greater molecular flexibility in the polymer strands. The Inventors electrospun PCL meshes containing 1% (wt/wt) MVC with two different fiber diameters: 371 nm and 1.3 mm. Upon incubation in VFS, all PCL meshes burst released more than 95% of the encapsulated MVC within 1 hour (FIG. 21b). Larger PCL fibers released 5.04% less MVC over 6 days (95% CI=3.92% to 6.17%, n=3) than small PCL fibers.

One can also modulate the crystallinity of pure PLA fibers by blending PLLA with varying amounts of lower molecular weight poly(D, Llactide) ("PDLLA"). PDLLA is chemically identical to PLLA, but displays key structural differences. In particular, PDLLA is amorphous, and allows for greater penetration of water into PLA meshes. The Inventors electrospun 25:75 and 50:50 PDLLA/PLLA blends containing 1% MVC. The resulting fibers showed regular morphology with similar fiber size (265±145 nm and 190±159 nm, respectively) to pure PLLA fibers (478±6287 nm). When placed into VFS, these PDLLA/PLLA meshes show no burst release, and released MVC linearly over six days. The amount of encapsulated MVC released after six days was 3.09±0.27% from 25:75 PDLLA/PLA fibers and 4.61±0.41% from 50:50 PDLLA/PLLA fibers. 50:50 PDLLA/PLLA meshes released significantly more MVC than 25:75 PDLLA/PLLA meshes (P value=0.0059, n=3). Therefore, modulating the polymer crystallinity by blending PDLLA with PLLA provided small, but sustained, linear release of MVC from electrospun fibers.

One can evaluate the activity and toxicity of our drug-loaded fibers in several relevant in vitro assays. MVC, AZT, and fibers re shown to be nontoxic to TZM-bL cells, and no difference between treated cells and media controls is observed (Bonferroni post test, a=0.05). One can test the ability of both the drug eluates released from 70:30 PLLA/PEO and 30:70 PLLA/PEO fibers and the drug-loaded fibers themselves to inhibit HIV-1 BaL infection in TZM-bL cells. First, the Inventors determined the specific antiviral activity of drug eluates released from the fibers to confirm that the absolute drug activity was not diminished by electrospinning. The Inventors measured an IC50 value of 0.90 nM and 2.3 nM for unformulated and eluted MVC, respectively. The IC50 of unformulated and eluted AZT was found to be 120 nM and 84 nM, respectively (FIG. 22a). The order of magnitude agreement between drug IC50 values before and after spinning suggests that the stabilities of MVC and AZT are maintained during electrospinning. Incubating TZM-bL cells with drug-loaded fiber discs significantly inhibits HIV-1 infection compared to blank fibers (P value, 0.0001) (FIG. 22b).

The polymer composition of the mesh at this dosing does not impact their anti-HIV activity, and one can observed equivalent viral inhibition for both drugs using the 30:70 and 70:30 PLLA/PEO meshes (Bonferroni post test, a=0.05). Fiber toxicity is evaluated in an ex vivo tissue explant model using macaque cervical tissue. In contrast to tissue treated with N-9, one observes no reduction in tissue viability due to exposure to blank fibers or fibers loaded with 10% (wt/wt) GML as determined using an MTT assay and by histological examination of tissue morphology (FIG. 22c, d).

Example 30

GML Fibers are a Chemical and Physical Barrier Against Sperm Function

To identify whether electrospun fibers can provide a contraception mechanism, particularly in a multipurpose prevention strategy, the Inventors sought to identify non-hormonal chemical alternatives to N-9. The spermicidal capabilities of ferrous D-gluconate ("FeGluc") and ascorbic acid ("Asc") are investigated to corroborate findings that the metal compound and ascorbic acid cause rapid spermiostasis due to lipid peroxidation of sperm. Another molecule of interest is methyl-bcyclodextrin ("MBCD"), which is suggested to sequester cholesterol from semen and lead to premature sperm capacitation. FeGluc and MBCD are readily incorporated into electrospun fibers (FIG. 19), but these agents are ineffective at inhibiting sperm function as assayed by measuring motility of purified (swim-out) human sperm.

Based on the amphiphilic properties of glycerol monolaurate ("GML") and its reported function to interact with lipid bilayers, it is of interest to evaluate GML activity on sperm function. It was suggested that GML could potentially interact with sperm plasma membranes to reduce sperm viability and motility. Related techniques are described in U.S. provisional patent application No. 61/723,024, filed Nov. 6, 2012, which is herein fully incorporated by reference.

Using human swim-out sperm, GML inhibited sperm motility at concentrations of 0.05-0.5% (wt/vol) (FIG. 22a). At these concentrations, complete spermiostasis was measured in 5 min. Reduction in motility is also observed at concentrations down to 0.00005% (wt/vol) but does not result in complete spermiostasis during the measurement time (FIG. 22a). GML also reduces viability of human sperm in whole semen by 33.1% (95% CI=24.0% to 42.2%, n=2) when tested at a 5% (wt/vol) concentration and by 19.6% (95% CI=10.7% to 28.9%, n=2) (FIG. 22b). One can also fabricate fibers loaded with 1% or 10% (wt/wt) GML using both PLLA/PEO blends. GML fibers re reproducibly electrospun to achieve polymer recoveries of 70% and fiber diameters between 600-800 nm. Fibers loaded with 10% (wt/wt) GML released 100-200 mg/mL into VFS within 1 h, suggesting that 100% GML released from fibers within 1 hour of incubation with VFS (FIG. 22c).

In addition to encapsulating agents that chemically inhibited sperm function, the fibers serve to physically block sperm penetration. Using transwell assay, one can measure the ability of sperm to penetrate electrospun meshes in the absence of drugs. The thicknesses of the tissue insert controls and electrospun meshes used as barriers were 30 mm and 150 mm, respectively. It is observed that motile sperm placed onto electrospun mesh are unable to swim through the fiber meshes despite the presence of numerous pores greater than 3 mm (FIG. 22d-e). In contrast, tissue culture insert controls with 3 mm diameter pores allowed sperm to penetrate into the bottom chamber. Approximately 58,000 sperm/mL (1.7% of sperm) penetrated the commercial membranes in 2 h, whereas no sperm penetrated the fiber meshes. This is unexpected as the size of the fiber mesh would not be expected to stop sperm passage. SEM image analysis confirmed these results, as we observed sperm on the underside of the control membranes but not the electrospun fiber meshes (FIG. 22f-i). To assess the material strength of the electrospun meshes, one can perform uniaxial tensile testing on samples of PCL containing 1% MVC that were spun at 5, 50, or 100 mL/min (n=2). It is observed that all materials had a Young's modulus between 25-120 MPa. In addition, materials were able to withstand at least 50% strain before failure. There was a statistically significant difference in Young's moduli between fibers spun at different flow rates, as determined by ANOVA (P=0.048). A Bonferroni corrected t test was used to compare 5 mL/min and 50 mL/min fibers. It was found that fibers spun at a flow rate of 50 mL/min were on average 68 MPa stiffer than those spun at a flow rate of 5 mL/min (95% C.I=2.8 to 130 MPa stiffer).

Example 31

Electrospun Fibers Deliver Agents that Inhibit Both HIV and Sperm In Vitro

Also described herein the Inventors show that electrospun fibers can deliver agents that inhibit both HIV and sperm in vitro in addition to physically preventing sperm penetration. In addition, a novel function of GML is described to act as a spermicide and potential non-hormonal chemical contraceptive. This finding adds to the characteristics that make GML an attractive candidate for use in topical microbicides for multipurpose prevention. Unlike existing vaginal drug delivery systems, polymer fibers provide a single dosage form that is readily amenable to encapsulating an array of small molecule hydrophobic and hydrophilic compounds. The diversity and number of polymers that can be electrospun should permitted a correspondingly large number of active agents to be encapsulated for sustained delivery. Drug-eluting fibers formulated with a single agent can be assembled into a composite mesh to deliver drug combinations. Combined with the ability to control device geometry, one expects that layered chemical function will permit delivery of specific drugs to defined regions within the lower female reproductive tract. The application of drug-eluting fibers for drug delivery to prevent HIV-1 and inhibit sperm function is unprecedented, and has wide implications for the design of next generation multipurpose prevention technologies.

Topical delivery systems that combine potent and broadly active inhibitors have the greatest likelihood of protecting against Nanofibers for HIV-1 Inhibition and Contraception. The compounds that incorporated into the described fibers have different mechanisms of action against HIV and HSV-2. MVC prevents HIV entry by binding to CCR5 and is already in clinical trials for use as a microbicide (MTN-013/IPM 026). While AZT is not currently a leading candidate for use in topical microbicides, its physicochemical properties are similar to those of tenofovir, which has been used in recent and ongoing clinical trials of microbicide gels. GML, which is described herein as having activity against sperm function, and has also been shown to inhibit HIV infection in vitro and SIV infection of macaques in vivo by inhibiting the production of MIP-3a and other pro-inflammatory cytokines Finally, also described herein is ACV incorporated into fibers, since HSV-2 infection is of great concern in its own right and in relation to risk of acquiring HIV and other STIs. Together, these four compounds demonstrate that electrospun fibers may be a useful platform for vaginal drug delivery and topical prevention of STIs.

Using the techniques described herein, one can electrospin fibers from mixtures of PEO and PLLA. PEO appears to possess the capability to rapidly hydrate and dissolve in vaginal fluid and that PLLA would degrade slowly via hydrolysis at low pH into lactic acid, a natural component of vaginal fluid important for maintaining vaginal homeostasis. The Inventors also found that the magnitude of MVC release from PLLA/PEO blends was highly dependent upon the amount of PEO present.

Over six days, 78% of encapsulated MVC is released from 70:30 PLLA/PEO fibers, compared with 93% of encapsulated MVC from 30:70 PLLA/PEO fibers. In contrast, approximately 90% of encapsulated AZT was released from both 70:30 and 30:70 PLLA/PEO fibers (FIG. 21). This suggests that MVC can disperse evenly throughout both PEO and PLLA, while the majority of AZT partitioned into PEO. Small diameter hydrophilic fibers represent an improvement on current film devices that provide coitally dependent protection against STIs and pregnancy. This data shows that substantial amounts of hydrophilic and hydrophobic drugs can be delivered very quickly from nanometer diameter fibers. Meshes made from hydrophilic polymers have previously can dissolve and release encapsulated agents more rapidly than films cast from the same materials Due to the high surface area-to-volume ratio of electrospun fiber meshes, water may ingress more rapidly into hydrophilic electrospun materials than into cast films. Rapid hydration and a shorter diffusion distance offered by a nanofiber can create a very steep concentration gradient of encapsulated molecules, thus enhancing the rate of mass transport into mucosal tissues.

As a result, it is clear that nanofibers can enhance the dissolution and mucosal delivery of ARVs. The ability to hydrate rapidly upon insertion can aid in fast drug release and effective spreading of dissolved materials along the vagina. Material spreading can result in more complete coverage of the mucosal tissue that is vulnerable to infection by HIV and other pathogens. Insertion of indocyanine green loaded 30:70 PLLA/PEO fibers into the vagina of a mouse resulted in high levels of fluorescence throughout the vaginal tract. This suggests that fibers can sufficiently hydrate in small volumes of vaginal fluid and release encapsulated agents within 30 minutes in vivo. Hydrophilic polymer-based fiber meshes, including those made from PEO, can therefore provide a useful dosage form for pericoital prevention methods.

While rapid release of antivirals and contraceptives is desirable for pericoital prevention, sustained release of agents is desirable for providing extended periods of coverage that may increase user adherence. In contrast to PEO, PLLA is significantly hydrophobic, and fibers with high PLLA content more closely resemble solid depots like IVRs or drug-eluting diaphragms. Polymer fibers with a partially hydrophobic composition would permit encapsulation and sustained release of hydrophobic agents. While the described results demonstrated that partially hydrophobic fibers could successfully incorporate MVC and GML (two hydrophobic agents), 70% and 30% PLLA content did not provide sustained release as expected (FIG. 21), The Inventors therefore evaluated multiple strategies for controlling the release of MVC from electrospun fibers by increasing fiber diameter, reducing hydrophilic polymer content, and modulating polymer crystallinity.

Our first strategy for sustaining release of MVC was to electrospin larger diameter fibers. While increasing PDLLA fiber diameter from 212 to 551 nm can lead to slower release of the highly water-soluble compound acetaminophen, the Inventors that MVC release from 70:30 PLLA/PEO fiber meshes was not altered by increasing fiber diameter six fold from 560 nm to 3.4 mm. If the release of MVC from 70:30 PLLA/PEO fibers were diffusion controlled, an increase in diameter by a factor of six should have decreased release rates by a factor of approximately 36. No significant slowing of drug release, although it was noted that increasing fiber size resulted in a 9.64% (95% CI=1.17% to 18.1%) reduction in the amount of drug released after 6 d (FIG. 21$b$).

Another variation includes reducing the hydrophilic content in PLLA/PEO blends to mediate sustained release of MVC by reducing the amount of PEO at the surface of the fibers. The release data from 70:30 and 30:70 PLLA/PEO fibers containing 1% (wt/wt) MVC showed that the extent of MVC release was related to PEO content. In fact, one could not detect any MVC release from 100% PLLA fibers in VFS. Electrospun 99:1 PLLA/PEO fibers were evaluated to ascertain if much smaller amounts of PEO could still allow for hydration of the mesh and release of MVC, but prevent burst release. One observes that fibers composed of 99:1 PLLA/PEO provides a linear release of 1.19 60.28% of encapsulated MVC over six days. This amount of MVC corresponded to an average concentration of 3606 120 nM (n=3) MVC, two orders of magnitude greater than MVC's IC50 in vitro. Nevertheless, much of the MVC remained trapped within the PLLA, highlighting that the PLLA/PEO blends that were tested may not be optimal for sustained release applications for MVC. However, these results demonstrate that controlling the relative amounts of polymers in blended fibers can modify not only the magnitude of release, but also the kinetics of release. The addition of porogens, acid catalysts, or glycolic acid groups in future.

Different formulations may enhance water penetration and polyester degradation, thereby improving the magnitude of drug release. It is unlikely that the hydrophobic nature of PLLA alone is responsible for the lack of MVC release from PLLA. The semi-crystalline structure of PLLA may be responsible for preventing MVC release from the hydrophobic portions of blended fibers by occluding water penetration. To measure such a phenomenon, one can modulate the crystallinity of PLA fibers by blending PDLLA with PLLA and looked for sustained release of MVC in VFS over six days (FIG. 21$b$). PDLLA is comprised of a racemic mixture of the D- and L-stereoisomers of lactic acid and has an amorphous microstructure that allows increased water entry and accelerated polymer degradation compared to PLLA. It was observed that electrospinning 25:75 and 50:50 blends of PDLLA and PLLA allows the ingress of water and the subsequent linear, sustained release of MVC over six days. 25:75 and 50:50 PDLLA/PLLA fibers had similar sizes; 25:75 fibers were around 20% larger than 50:50 fibers.

The rate of MVC release from PDLLA/PLLA fibers can increase with the PDLLA content, but remained small. It was observed that 50:50 PDLLA/PLLA fibers only released 4.6±0.41% of MVC into VFS over 6 d. Thus, electrospun fibers can sustain release of ARVs over multiple days and it is likely that encapsulating MVC in pure PDLLA would result in greater release of MVC due to reduced crystallinity and accelerated polymer degradation.

Figure 22:
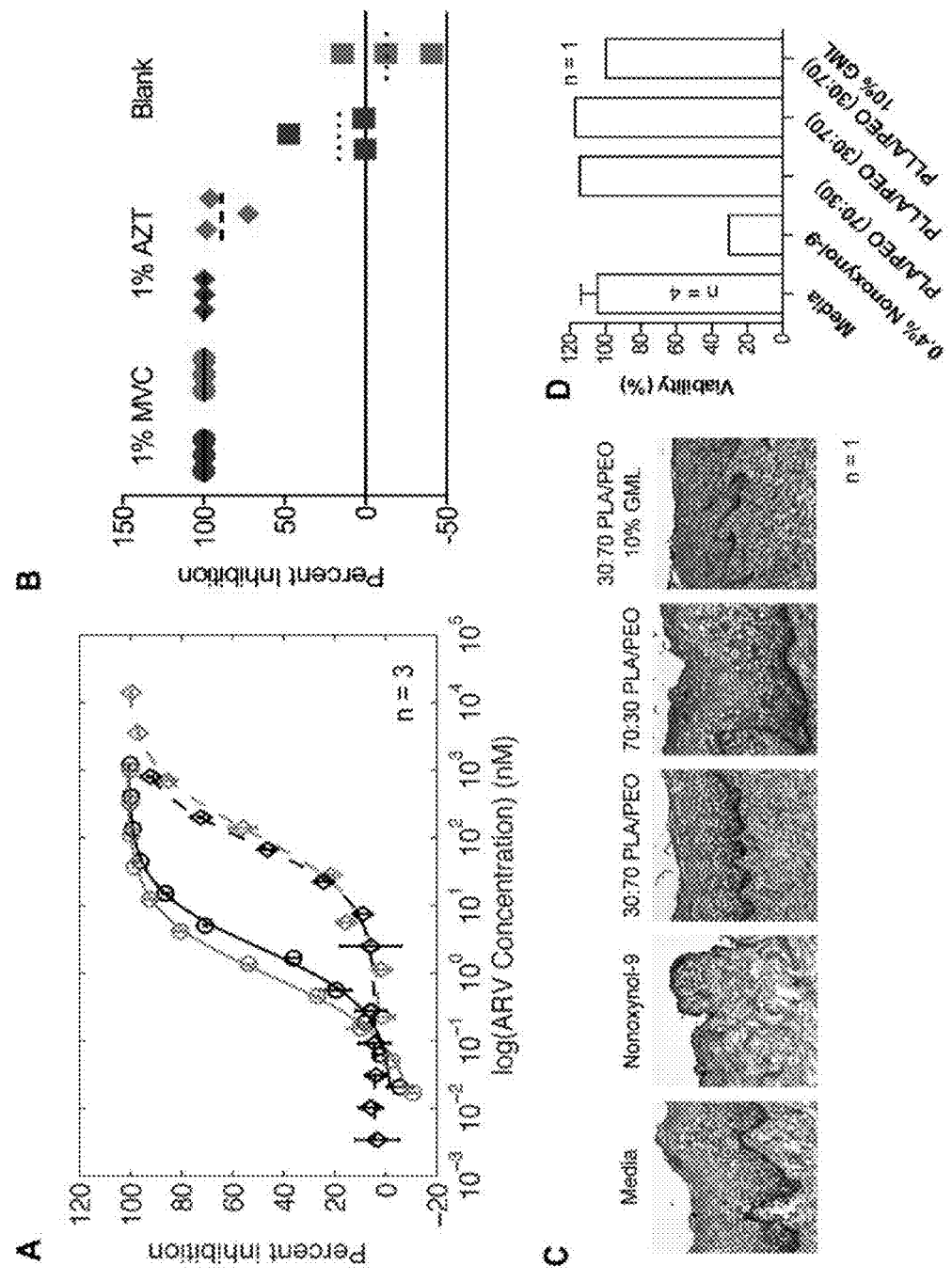
FIG. 22. Fiber meshes inhibit HIV in vitro and are nontoxic to macaque cervical tissue explants. (a) Dose-response assay indicates that AZT and MVC released from fibers have similar potency to unformulated drugs (drug eluates, black and unformulated drug, gray). (b) Drug loaded fiber blends (30:70 PLLA/PEO (blue) and 70:30 PLLA/PEO (red)), but not blank fiber controls, show equivalent inhibition of HIV infection. (c) Histology indicates that 30:70 PLLA/PEO, 70:30 PLLA/PEO, and 30:70 PLLA/PEO fibers with 10% (wt/wt) GML are nontoxic to macaque cervical tissue explants compared to nonoxynol-9 control. (d) MTT assay confirms fibers, including those containing 10% (wt/wt) GML, are nontoxic to tissue explants. Note that for media controls n=4, and for all other groups n=1.
Figure 23:
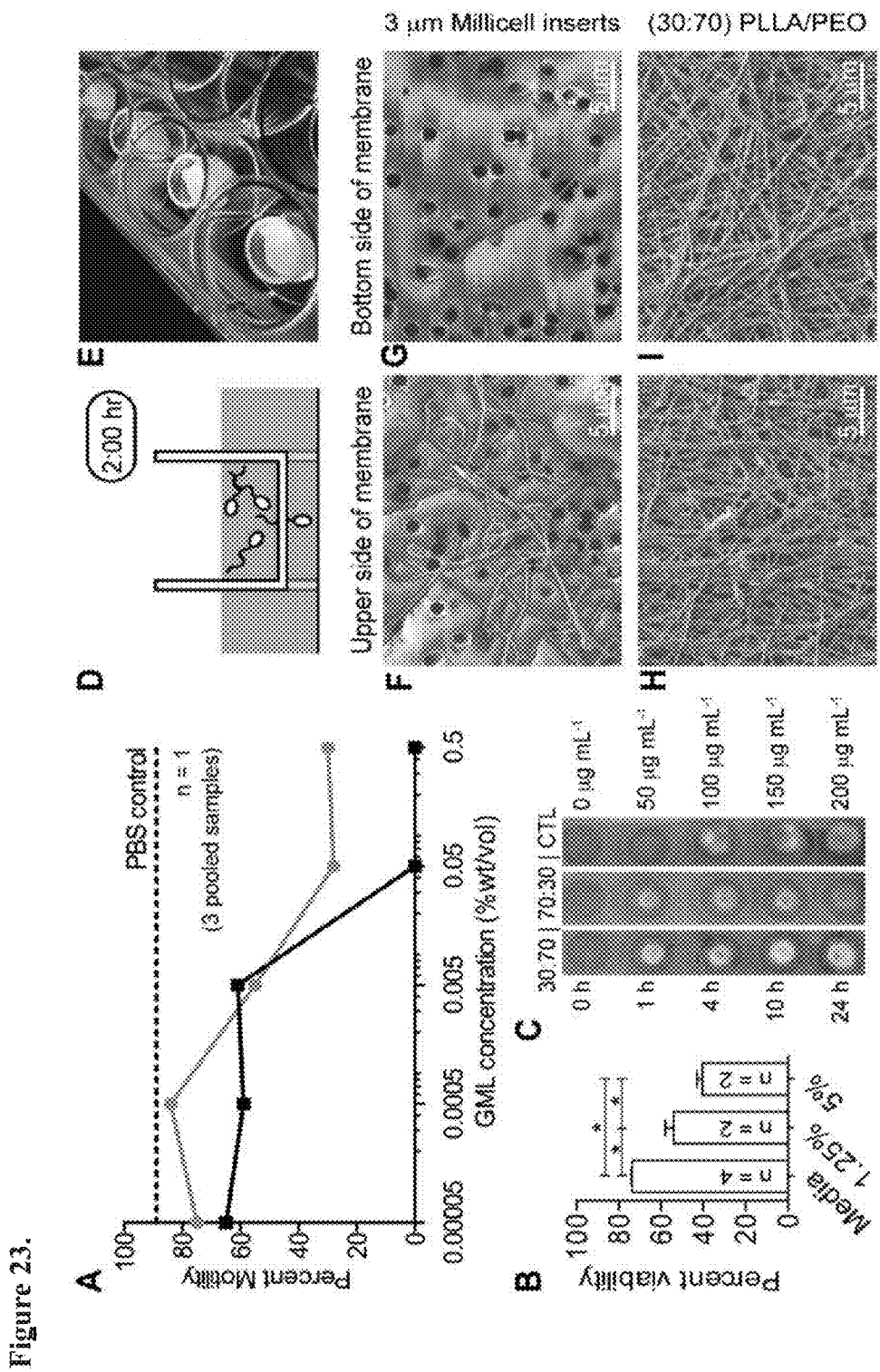
FIG. 23. Fiber meshes are a physical and chemical barrier against sperm. (a) Motility of human swim-out sperm was completely inhibited within 5 min for 0.05 and 0.5% GML. Data show counts of motile and immotile sperm at 2 min (gray line) and 5 min (black line). Baseline sperm motility (~89%) was measured at the beginning and end of experiment using a PBS control (dotted line). (b) Sperm viability is reduced in whole semen incubated with GML compared with media control. (c) GML release from fiber meshes was qualitatively measured using TLC. (d, e) A transwell assay was used to test the physical barrier properties of the fiber meshes by replacing Millicell cell culture insert membranes (3 μm pore diameter) with a blank fiber mesh (n=3). (f, g) SEM micrographs of the upper (f) and lower (g) side of Millicell control membrane. (h, i) SEM micrographs of upper (h) and lower side (i) of fiber mesh show that no sperm penetrate through the fiber mesh.

In addition to releasing ARVs, it is critical that fibers are safe and effective in biological systems. One can evaluate the antiviral activity of fibers loaded with either AZT or MVC using an in vitro TZM-bL assay. This model has previously been used to evaluate drug candidates for topical microbicides. Both the drug eluates from in vitro fiber release studies and drug-loaded fibers themselves were found to potently inhibit HIV compared to blank fibers. The IC50 values of unformulated ARV versus eluted ARV were of a same order of magnitude (FIG. 22$a$). These results suggest that fibers are able to release sufficient levels of drug in cDMEM to prevent HIV infection in TZM-bL cells over 48 hours, which is consistent with the release profiles obtained from in vitro release studies in VFS (FIG. 22$b$). Furthermore, these studies demonstrate that both drugs are in a bioavailable form after the electrospinning formulation process. The toxicity of fibers was measured with a macaque cervical explant model using histological examination and an MTT viability assay (FIG. 22). Tissue exposed to either 30:70 or 70:30 PLLA/PEO fibers is observed to have similar epithelial layer integrity and cell viability compared with untreated control tissue, indicating the biological suitability of the polymer blends for additional studies in vaginal drug delivery.

Long-term shelf stability is another quality imperative to the design of effective dosage forms for multipurpose prevention. The Inventors detected 0.95% of the initially-loaded AZT and MVC in fiber meshes stored at room temperature for at least five months and observed that fiber meshes retained similar appearance and texture over this period. This data suggests that ARVs remain stable in PLLA/PEO fiber meshes under standard storage conditions; solid dosage form of drug-loaded fibers will be advantageous for long-term stability compared with semisolid dosage forms like vaginal gels.

Example 32

GML Activity on Sperm Function

GML's activity on sperm function it of interest based on its amphiphilic properties and its reported interaction with lipid bilayers. GML, a glycerol ester of lauric acid that is used commonly as an emulsifier in foods and cosmetics, is regarded by the FDA as safe for topical use at doses up to 100 mg/mL. Additionally, GML is inexpensive, possesses documented anti-inflammatory properties, and is antimicrobial for a number of vaginal pathogens. Described herein, GML potently reduces sperm motility in a dose-dependent manner (EC50, 0.005% wt/vol at 2 min) and significantly lowers sperm viability at concentrations equivalent to those used in recent microbicide studies with macaques (5% wt/vol). Although its spermicidal mechanisms are as yet unknown, interference with signal transduction by incorporation into plasma membranes has been suggested as a mechanism for its antibacterial and anti-inflammatory properties] and may also be involved in sperm inhibition. Future studies should perform an in-depth characterization of how GML causes spermiostasis. Our findings add to the list of properties that make GML an attractive candidate for use in topical microbicides for multipurpose prevention, including anti-inflammatory mediated prevention of SIV infection in macaques and the capacity to prevent bacterial infections. The low aqueous solubility of GML (50-100 mg/mL at pH 7) precludes evaluation of activity of higher concentrations of GML on human sperm in whole semen, but provided a strong rationale to formulate GML in polymer fibers. A dosage form that enhances the bioavailability of GML could potentially would clearly enhance the spermicidal potency of the compound. In addition to the chemical inhibition provided by GML, blank fibers block sperm migration in a transwell assay (FIG. 22). Relying upon a porous mesh to block sperm penetration differs from current barrier approaches, which rely on nonporous materials to block sperm entry into the cervix. These results show that a porous, tortuous mesh fabricated by electrospinning can efficiently block sperm entry. This suggests that, if fabricated in the appropriate geometry and given the appropriate mechanical strength, electrospun fibers can serve as an effective barrier contraceptive. The mechanical properties of electrospun fibers as a barrier device, suggests their application in contraceptive use. For example, the Young's moduli of electrospun materials made from 70:30 PLLA/PEO fibers with 1% (wt/wt) MVC were around 50-100 MPa, and electrospun meshes withstood at least 50% extensional strain before failure. For comparison, latex rubber condoms have a Young's modulus of approximately 2 MPa and can withstand inflation to volumes greater than 20 L. Dapivirine films have a tensile modulus of 5.4 to 7.8 MPa. Based on the mechanical properties of these electrospun materials, it is unlikely that they would be effective as a condom-like device, but they may be suitable as devices similar to vaginal sponges or diaphragms.

Example 33

Polymer Preparation

Polymers used for electrospinning included poly(L-lactide) with an inherent viscosity of 0.90-1.20 dL/g (MW, 117 kDa) (Lactel Absorbable Polymers), poly(ethylene oxide) with MW 100 kDa (Sigma-Aldrich), polycaprolactone of Mn 70-90 kDa (Sigma-Aldrich), and acid terminated poly(D, L-lactide) of Mw 18-24 kDa (Sigma Aldrich). Maraviroc was obtained from the NIH AIDS Research & Reference Reagent Program, Division of AIDS, NIAID, NIH. 39-Azido-39-deoxythymidine, methyl-b-cyclodextrin (Mn=1310), acyclovir, iron(II) D-gluconate, and L-ascorbic acid were purchased from Sigma-Aldrich. Glycerol monolaurate was purchased from MP Biomedicals, LLC. VFS was made according to methods described in the art. Potassium hydroxide, calcium hydroxide, lactic acid, acetic acid, and glycerol were purchased from Fisher Scientific. Bovine serum albumin, urea, and glucose were obtained from Sigma-Aldrich. Sodium chloride was purchased from Mallinckrodt Chemicals. The pH for VFS was adjusted to 4.2 with HCl and filter sterilized.

Example 34

Electrospinning

PLLA and PEO are dissolved at 5%, 10%, 15% (wt/vol) in mixtures of 1:1 or 3:1 (vol/vol) chloroform (EMD Chemicals) and 2,2,2-trifluoroethanol (Sigma-Aldrich). PCL is dissolved at 10% and 15% (wt/vol) in 2,2,2-trifluoroethanol. PDLLA and PLLA are dissolved at 15% (wt/vol) in 1:1 chloroform and 2,2,2-trifluoroethanol. Drugs are mixed with polymers at 1 or 10% (wt/wt) prior to addition to solvent. Polymer solutions re loaded into glass gastight syringes (National Scientific) and set into a precision syringe pump (KD Scientific Inc.). Unless otherwise specified, fibers are produced with the following parameters.

One can dispense 500 mL at a flow rate of 5 mL/min through a gauge 22 stainless steel dispensing needle (Integrated Dispensing Solutions, Inc.) that is clamped to +15 kV using a high voltage generator (Gamma High Voltage Research). The aluminum mandrel collector is machined at the University of Washington to have a diameter of 1.27 cm. The collector is placed 12 cm horizontally from the tip of the needle and set to 3,000 r.p.m. (linear rotational speed of 200 cm/s at the surface of the collector) with a 5.08 cm horizontal travel at a speed of 2.54 cm/s. A copper or graphite brush electrically grounded the mandrel. 3.4 mm 70:30 PLLA/PEO fibers is produced as above except polymers were dissolved at 25% (wt/vol) and spun at 100 mL/min at 1,200 rpm. 1.5 mm 70:30 PLLA/PEO fibers are produced as 3.4 mm fibers except a 20% (wt/vol) solution of polymer is used.

PDLLA/PLLA fibers are produced as above except for the flow rate and mandrel speed, which are 100 mL/min and 1,200 rpm, respectively. PCL fibers are produced by dispensing 500 mL at a flow rate of 100 mL/min from a 25 G needle clamped to +12 kV voltage and set 8 cm from the collector, which was rotating at 1,200 rpm. Electrospun meshes re removed from the collector and lyophilized for at least 24 h before imaging or use in biological assays thickness was measured using calipers. Dog bone shaped samples re cut from collected meshes with a D1708-96-MET die (ODC Tooling and Molds) such that the long axis of the dog bone corresponded to the circumferential direction of the mandrel collector. Uniaxial tensile testing was performed with an Instron model 5543 instrument and model 2712-03 grippers (Instron). Samples were stretched at a rate of 10 mm/min until failure. Young's modulus was estimated by fitting stress-strain curves with a line for 0-15% of maximum stress.

Example 35

Drug Release and Loading

Triplicate samples of mesh approximately 10 mg each containing AZT or MVC re placed into 6 mL glass vials, immersed in 6 mL of VFS, and incubated at 37° C. on an orbital shaker at 200 r.p.m. At set time points (1 h, 4 h, 8 h, 12 h, 24 h, 48 h), 500 mL of buffer is removed and replaced with fresh VFS. A Shimadzu Prominence LC20AD UV-HPLC system equipped with a Phenomenex Luna C18 column (5 mm, 25064.6 mm) and LCSolutions software is used to quantify drug levels in samples. Methods for MVC are based on those techniques known to one of ordinary skill in the art. The mobile phase consisted of HPLC grade 0.01M KH2PO4 buffer and acetonitrile (60:40, vol/vol) (EMD Chemicals) at isocratic flow rate of 1.0 mL/min for 10 min. Column oven temperature was 25° C. Standards re made in VFS, with linearity established from 0.001 to 0.02 mg/mL with 20 mL injection volume. MVC is detected at 193 nm with a retention time of 3.1 to 4.1 min. AZT is detected using an isocratic mobile phase was composed of HPLC grade water with 0.045% trifluoroacetic acid and acetonitrile with 0.036% trifluoroacetic acid (72:28) at a flow rate of 1.0 mL/min for 15 min, with column oven temperature of 30° C. AZT is detected at 265 nm at retention time of 4.4 min.

Standards are prepared in water, with a linear range from 0.001 to 0.5 mg/mL with 10 mL injection volume. GML release from fiber meshes is detected using thin-layer chromatography (TLC). 10 mg pieces of either 30:70 PLLA/PEO or 70:30 PLLA/PEO with 10% (wt/wt) GML are added in triplicate to 6 mL of PBS at pH 4.2. Samples were incubated at 37° C., and 500 mL were removed at periodic intervals and replaced with fresh PBS (pH 4.2) or 48 h. mL of release media (n=3) were added onto duplicate TLC plates. After drying, plates were baked at 100° C. for 10 min, then allowed to cool to room temperature. Plates re then immersed in 0.025% (wt/vol) Coomassie blue (Fisher) in 20% (vol/vol) methanol for 10 s and allowed to dry for 1 h.

Plates were then digitized using a scanner. Drug loading and stability is measured using fibers stored at room temperature (19-22° C.) for at least five months. 10 mg pieces of fiber mesh were dissolved in 2.5 mL acetonitrile, centrifuged for 10 min at 10,000 g, and added to 0.01 M KH2PO4 buffer or water at a 1:1 ratio for MVC or AZT fibers, respectively. UV-HPLC is used to quantify amount of drug in samples as previously described. Encapsulation efficiency is calculated as the amount of drug in drug-loaded fibers relative to the amount of drug detected in dissolved blank fibers spiked at 1% (wt/wt) drug loading.

Example 36

Mouse Fiber Coverage Study and HIV Inhibition Assay

Two eight-week old female Balb/cByJ mice (Jackson Laboratories) were cycled with injections of medroxyprogesertone acetate (Greenstone LLC) four days prior to fiber insertion. Fiber meshes of dimensions 262 cm were folded around an applicator and inserted into the mouse vagina. The control mouse received blank 30:70 PLLA/PEO fibers, and the experimental mouse received 30:70 PLLA/PEO fibers electrospun with 1% (w/w) indocyanine green (Sigma-Aldrich). Mice were anesthetized during the procedure with isoflurane administered through nose cones. Mice were sacrificed after 30 minutes, and reproductive tracts were excised for imaging. Fiber meshes were removed after dissection and imaged with excised reproductive tracts. A Xenogen in vivo imaging system (IVIS) was used to measure fluorescence at 745/820 nm as a surrogate for fiber coverage.

TZM-bl cells and HIV-1 BaL isolate re obtained from the NIH AIDS Research and Reference Reagent Program, Division of AIDS, NIAID, NIH (http://www.aidsreagent.org/). TZM-bL cells, a derived HeLa cell line that expresses CD4, CCR5, and CXCR4, were added to black 96-well plates (Corning, Corning, N.Y.) with Dulbecco's Modified Eagle Medium (DMEM) (Gibco Life Technologies) with 10% fetal bovine serum (Hyclone), 1% 100× penicillin/streptomycin (Invitrogen), and 1% 200 mM L-glutamine (Invitrogen) with 50 mL/well at a density of 5,000 cells/well. Cells are incubated in 5% CO2 and 37° C. for 24 h prior to exposure to drugs or fibers. Fibers re sterilized by UV irradiation for 2 h (1 h per side). Treatments were added in 50 mL volumes. For the HIV-infectious inhibition assay, 100 mL of HIVBaL (240 TCID/well) are added to wells 1 h after drug treatment. Media is removed from cells after 48 h post-treatment, and 100 mL of phosphate buffered saline (Gibco Life Technologies) and 100 mL of Bright-Glo Luciferase reagent (Promega) were added to wells. Infectious activity is quantified by measuring luminescence on a plate reader (Tecan). IC50 values of drug compounds are estimated using sigmoidal regression and bootstrapping in MATLAB version 7.11 (Mathworks).

Example 37

Explant Toxicity Assay

Macaque ectocervical tissues (Tissue Banking and Distribution Program, University of Washington National Primate Research Center) are processed for polarized explant cultures in duplicate on the day of surgery. Briefly, a circular tissue punch is inserted through the transwell membrane with the luminal side up. The edges around the explant are sealed with Matrigel™ (BD Biosciences, San Jose, Calif.). A 0.6 mm diameter disc of either 30:70 PLLA/PEO, 70:30 PLLA/PEO, or 30:70 PLLA/PEO with 10% (wt/wt) GML fiber is placed on the apical side of the tissue with 200 mL of culture media (DMEM with 10% fetal bovine serum, 1% 100× penicillin/streptomycin, and 1% 200 mM L-glutamine). For controls, explants are untreated (culture media) or treated with a 0.4% dilution of nonoxynol-9 (N-9) gel. The explant cultures were maintained at 37° C. in a 5% CO2 atmosphere. After 18-24 h, the explants were washed and one of each duplicate was incubated in RPMI containing 250 mg/ml MTT [1-(4,5-dimethylthiazol-2-yl)-3,5-diphenylformazan] for 4 h. The explants are removed and placed in 1 mL of methanol overnight to extract the formazan dye produced by live tissue. The next day, the explants are removed from methanol and placed on a marked paper towel to dry and be weighed. The color extracted in the methanol is read for optical density at 595 nm. The percent viability of the treated explants was determined by correcting the optical density (OD) with the weight of the corresponding explant. The other explant is frozen in an embedding medium (Tissue-Tek, Sakura Finetek USA Inc., CA) and processed for histology by cryosectioning and hematoxylin-eosin staining.

Example 38

Sperm Motility, Viability, Migration Assays

Sperm is obtained from two donors for sperm motility experiments. A third donor is recruited for sperm viability assays with glycerol monolaurate. Swim out sperm are obtained as described previously. Briefly, one can place 0.5 mL aliquots of semen below 3 mL of Ham's F-10 media (Sigma-Aldrich) with 0.5% human serum albumin (Sigma-Aldrich) for 75 min in 5% CO2 and 37° C. The aspirate, enriched for motile sperm, was centrifuged at 300 RCF for five min and resuspended in fresh Ham's F-10 to a concentration of $20 \times 10^6$ sperm/mL. The effect of drug dilutions on sperm motility are performed both in whole semen and in swimout sperm by adding 5 mL each of sperm and drugs to a slide and observing sperm motility with phase contrast either at 200× and 37° C. (ECLIPSE Ti, Nikon), or by adding 200 mL of drug to 100 mL of semen and quantifying sperm motility with computer aided motility analysis for up to 7 min after the addition of drug. Multiple media only controls are run to ensure that any observed change in motility was minimally dependent upon time since ejaculation. Sperm viability was measured by adding 20 mL of semen to 20 mL of Trypan blue (Sigma-Aldrich) and counting 100 live or dead sperm based on head staining after a 10 min incubation using brightfield microscopy.

For migration assays, Millicell cell culture insert membranes (Millipore) with 3 mm pores were removed with forceps and replaced with square pieces of electrospun mesh. The mesh was attached to the inserts by applying firm pressure with a gloved finger. The thicknesses of cell culture insert membranes and electrospun meshes were measured using a micrometer. Modified and unmodified inserts were placed in a 12 well plate. Swimout sperm were diluted 1:10 in Ham's F-10 with no protein. 600 mL of Ham's F-10 was added to each of the twelve wells, and 400 mL of diluted sperm was added to each insert. Sperm were incubated for 2 h at 37° C. and 5% CO2. The solutions from the inner and outer chambers of the wells were aspirated and used for counting to measure sperm concentration in media inside and outside of the inserts. Sperm were fixed by dipping membranes into ice cold ethanol and were then lyophilized for 24 h. Meshes were imaged using SEM with the same settings used to image blank meshes.

Example 39

Maraviroc Loading in Drug Eluting Fibers

Maraviroc ("MVC") is of interest for use in a microbicide due to its effectiveness at treating HIV, high potency in animal models, and favorable toxicity profile. Maraviroc works by binding to CCR5 coreceptors on HIV target cells, thereby inhibiting viral entry. Since the majority of new HIV infections are CCR5-tropic, maraviroc may be particularly suited for use as a microbicide. Maraviroc is also not a first-line HIV medication, so the development of HIV resistance to maraviroc would not necessarily preclude the use of frontline treatments, such as fixed dose tenofovir and emtricidabine tablets. Maraviroc has been loaded into a HEC gel, two vaginal rings (one also containing dapivirine), and a silicone based elastomer gel for microbicide delivery. Maraviroc is a small molecule that is fairly soluble (>1 mg/mL) in mildly acidic pH. While previous microbicide formulation studies have shown that the drug can be delivered and absorbed intravaginally, researchers have not characterized the potential impact of the drug's physical state (crystallinity, spatial distribution in materials) on its release properties. While not yet tested in vivo, electrospun fibers offer potential advantages over existing pericoital dosage forms related to adherence and retention. Described herein is are methods demonstrating that maraviroc may be loaded at high levels into hydrophilic polymer nano- and microfibers for rapid intravaginal drug delivery, specific formulation parameters that affect the distribution and physical state of the drugs within the fibers and the rate of drug release, further including verification of full retention of the compounds' biological activity following release from fibers.

Example 40

Materials and Methods

Extraction and recrystallization of maraviroc from Selzentry® (ViiV Healthcare) was purchased through the University of Washington's Investigative Drug Services facility. Maraviroc is purified and recrystallized from Selzentry in a simple 7-step process. First, Selzentry tablets re crushed 6 at a time (1.8 g of maraviroc) by hand using a mortar and pestle. Due to the brittle nature of the pill's core and the more flexible properties of the pill's film-coat, the core is ground into a fine white powder while the film-coat remained in larger blue flakes. Second, a fine copper mesh (Home Depot) is used to separate the film-coat fragments from the interior powder. Third, 100 mL of dichloromethane (Sigma Aldrich) and 1 g of anhydrous MgSO4 (Fisher Scientific) are added to the powder and stirred with a magnetic stir bar for 10 minutes to dissolve the MVC into the dichloromethane. Fourth, this suspension is filtered through cellulose filter paper (Whatman) into a 250 mL round bottom flask. The filtrate is clear and colorless. Fifth, the dichloromethane is evaporated using a rotary evaporator (Rotovap) to produce a white foam (maraviroc-DCM polymorph). Sixth, refluxing ethyl acetate (Sigma Aldrich) is added slowly to the white foam while keeping the round bottom flask at a temperature of 70° C. Gentle swirling helped dissolve the maraviroc foam into the ethyl acetate. Once all of the maraviroc was dissolved, the round bottom flask was allowed to cool slowly to room temperature, then again to 4° C. White maraviroc crystals form in the ethyl acetate. Finally, the ethyl acetate is removed under vacuum using a rotary evaporator to yield pure and completely crystalline maraviroc. Yield is ~75%. Identity and purity is confirmed by proton-NMR on the sample dissolved in CDCl3 (University of Washington Chemistry Supplies Store). Common contaminants (<1% molar composition) are polyethylene glycol (from pill film-coat fragments) and ethyl acetate, identified by peaks on NMR spectra. Calorimetry measurements are taken to further verify crystallinity and purity using differential scanning calorimetry (see below).

Example 41

Preparation and Composition Characterization of Electrospinning Solutions

Polyvinylpyrrolidone ("PVP") with a MW of 1,300,000 Da is purchased from Sigma Aldrich (St. Louis, Mo.). Poly (ethylene oxide) (PEO) with a Mw of 400,000 Da is purchased from Scientific Polymer Products, INC (Ontario, N.Y.). 100% ethanol (USP grade) is purchased from the University of Washington's biochemistry supplies store. Distilled, deionized water is obtained using a Milli-Q-water purifier (Millipore). Polysorbate 20 (Tween 20) is purchased from Fisher Scientific. PVP, PEO, Tween 20, maraviroc, and solvents are added to pre-massed 20 mL glass scintillation vials with gas tight lids. The vials are massed after the addition of each ingredient so that the exact composition of the mixture could be determined after formulation. Solutions are mixed by gentle tumbling overnight on a rotisserie shaker (Labquake, Thermo Scientific). Solution density is measured by massing triplicate 500 µL, samples, taking the mean of the measurements, and dividing by the sample volume. The density of water and ethanol are measured as controls to ensure the accuracy of the method. Ingredient mass measurements, combined with a final solution density, re used to calculate the final solution volume. Then, the composition of the solution in terms of weight % and volume % re easily determined for all ingredients in both the solution and the solvent-free electrospinning product. Solution conductivity is measured using a calibrated conductivity probe (Thermo Scientific). Solution surface tensions are measured using an AquaPi surface tensiometer (Kibron). Rheological data are measured using an AR G2 series rheometer (TA Instruments) with a 40 mm 2° cone geometry in frequency sweep oscillation mode with a constant small strain of 4%. Measurements of G" are converted to viscosity measurements by dividing the angular frequency into G".

Example 42

Electrospinning and SEM Characterization

PVP solutions are electrospun at 15 kV over a 20 cm gap using flow rates of 25, 50, and 100 μL/min. PEO solutions are electrospun at 15 kV over a 25 cm gap using flow rates of 10, 25, and 50 μL/min. Solutions are spun either with or without a charged metal screen at the base of the needle to promote a spatially homogeneous electric field and increase polymer recovery. For each run, 1 mL of solution is spun from a glass syringe fitted with a 2.54 cm long 25 G stainless steel blunt dispensing needle. Fibers are collected onto a flat, grounded, aluminum surface covered with a single layer of wax paper. The wax paper substrate facilitates easy removal of the fiber samples from the collector with tweezers. After electrospinning, fiber samples re lyophilized for at least 24 hours. Then their final mass was recorded to determine yield. Materials are stored on the lyophilizer before use.

Electrospun fibers are examined by SEM using a Sirion SEM (NTUF, UW). Fibers are examined after sputtering with gold and palladium for 90 seconds to minimize charge buildup on fibers. Imaging settings of 5 kV, spot size 3, and working distance of 6.5 were used to obtain images. Fields of view are randomly selected in order to eliminate bias in selecting which fibers to image. Fiber diameters are measured in ImageJ (NIH) by bisecting the SEM image diagonally with a line and manually measuring the diameters of fibers that intersected that bisecting line. At least 25 fibers are measured per sample.

Example 43

Measuring Drug Loading by HPLC

A Shimadzu Prominence LC20AD UV-HPLC system equipped with a Phenomenex Luna C18 column (5 μm, 250×4.6 mm) and LCSolutions software is used to quantify drug levels in samples. The actual loading of maraviroc in electrospun fibers is measured with UV-HPLC (Shimadzu) by dissolving 2.5 mg pieces of mesh (n=1, containing 0.25 mg to 1 mg of maraviroc) in 50 mL of the HPLC mobile phase, which consisted of a 60% 10 mM KH2PO4 buffer and 40% acetonitrile, filtered through 0.45 μm, 0.22 μm, and glass frit filters to remove particulates. Polymers and maraviroc are freely soluble in the mobile phase. A fresh maraviroc standard curve is prepared by dissolving 20 mg of MVC in mobile phase to a concentration of 1 mg/mL and diluting serially at 1:2 until at concentrations of approximately 10 ng/mL. Spiked samples are prepared by adding MVC from 1 mg/mL stock solution to dissolved blank fibers with and without polysorbate-20. The maraviroc standard, spiked samples, and unknown samples re detected by UV-HPLC as described previously [6,16]. The calibration curve is prepared in Prism using 1/C2 weighting to minimize residuals. The linear range is found to be from 64,000 ng/mL to 400 ng/mL.

Example 44

Thermal Analysis by Differential Scanning Calorimetry (DSC)

Samples with a mass of 5-10 mg (n=1) are placed into aluminum pans (T-Zero, TA Instruments) and analyzed with a TA Auto Q20 DSC instrument (TA Instruments). Samples were heated from 30° C. to 250° C. at a rate of 10° C./min with a nitrogen flow of 50 mL/min. Peak integration was performed using TA Thermal Analysis software and sigmoidal tangential integration. Percent crystallinity of the polymer or the drug is calculated by normalizing the measured enthalpy per unit mass of polymer or drug to the measured heat of fusion of the pure substance.

Example 45

Fiber Surface Analysis by X-Ray Photoelectron Spectroscopy (XPS)

XPS is performed using a Surface Science Instruments S-Probe at the University of Washington's NESAC/BIO surface analysis recharge center. Due to the surface sensitivity of XPS measurements, care is taken to prepare samples with no surface contamination. Freshly electrospun materials recollected onto aluminum foil and immediately lyophilized. Samples are analyzed in triplicate and illuminated with low intensity electrons to reduce charging of the insulated materials. In addition to survey scans, high-resolution carbon scans and detailed nitrogen and fluorine scans are taken for all materials. Peak assignment and integration were performed using XPS analysis software (CasaXPS). Theoretical atomic percentages for C, N, O, and F are calculated assuming a uniform distribution of materials within electrospun fibers. The percent of the fiber surface covered by maraviroc molecules is calculated by normalizing the total fluorine content in each fiber sample to the fluorine content in pure maraviroc crystal. Enrichment of Tween 20 in PVP materials is assessed using atomic % oxygen, and was calculated only for blank PVP fiber materials.

Example 46

In Vitro Drug, Maraviroc Solubility Following Release from Fibers, Release into Sink Conditions To determine in vitro maraviroc solubility following release from fibers, measurement of drug release from fibers into saturated drug conditions is carried out to assess the solubility limit of maraviroc following release from electrospun fibers loaded with approximately 30 wt % maraviroc. Crystalline maraviroc or maraviroc-loaded fibers are added to citrate buffer at 50 mg of drug per 1 mL of buffer. Fibers are vortexed for 1 min, heated to 37° C. for 24 h, vortexed again for 1 min, and centrifuged to pellet insoluble drug and polymer. A clear, viscous supernatant is present in all samples. This supernatant is diluted 1:1000 into citrate buffer for quantification of drug concentration by UV-HPLC.

Sink release is studied in ambient conditions (20° C., 50% RH) in a pH 4.0 10 mM citrate buffer with 154 mM ionic strength. The release media is prepared by adding 2.101 g citric acid monohydrate and 8.066 g NaCl to a final solution volume of 1000 mL with distilled water. PBS (pH 7.0) is also used to assess the effect of drug ionization on release rate from highly loaded PVP fibers without Tween 20. Media is filter sterilized before use. Studies are carried out by adding 5 mg of fiber to a 50 mL conical tube secured to a rotisserie shaker (Labquake, Thermo Scientific). 25 mL of media re added (maximum [maraviroc]=0.06 mg/mL, >50 times lower than the drug's solubility limit) and a timer is started when fibers first touched fluid. Materials are tumbled gently at 7 RPM, and 50 μL samples were removed at 2 min intervals for 20 min (total of 500 μL). A 24 h time point is taken the next day as an approximation of infinite time. Spiked samples as well as pure drug crystal controls are also analyzed to validate quantitative methods. Purified maraviroc is micronized using a mortar and pestle, and particle size was assessed by SEM and imaging software (ImageJ, NIH). Release samples are thawed prior to quantification by UV-HPLC as described above.

Example 47

In Vitro Dissolution of Electrospun Fibers on a Moist, Porous Surface

Electrospun fibers are cut into 1.27 cm diameter circles using a metal die (Grainger) and gently dropped onto black agar plates (1.5% agar with 1% v/v of India ink) incubated at 37° C. No pressure is applied to fibers to force contact with the gels. When the fibers absorbed water from the gels, the black plate clearly shows through the dissolved fibers (opaque and white prior to swelling and dissolution). The degree of fiber dissolution is assessed visually every 30 seconds from time-lapse photos taken on a smartphone (iPhone 4, Apple).

Example 48

In Vitro Anti-HIV Activity of Dissolved Electrospun Fibers

TZM-bl cells and HIV-1 BaL isolate re obtained from the NIH AIDS Research and Reference Reagent Program, Division of AIDS, NIAID, NIH (http://www.aidsreagent.org/). TZM-bL cells, a derived HeLa cell line that expresses CD4, CCR5, and CXCR4, are added to black 96-well plates (Corning, Corning, N.Y.) with Dulbecco's Modified Eagle Medium (DMEM) (Gibco Life Technologies) with 10% fetal bovine serum (Hyclone), 1% 100× penicillin/streptomycin (Invitrogen), and 1% 200 mM L-glutamine (Invitrogen) with 50 µL/well at a density of 5,000 cells/well. Cells were incubated in 5% CO2 and 37° C. for 24 h prior to exposure to drugs. Treatments are diluted serially and randomly assigned to treatments A-E. A second operator, blinded to the identity of the treatments, added each in 50 µL volumes into duplicate wells (n=1 was used for PVP (D) and PEO Tween 20 (E) formulations only due to space limitations on the 96-well plate). 100 µL of HIV-BaL (240 TCID/well) was added to wells 1 h after drug treatment. Media was removed from cells after 48 h post-treatment, and 100 µL of phosphate buffered saline (Gibco Life Technologies) and 100 µL of Bright-Glo Luciferase reagent (Promega) were added to wells. Infectious activity was quantified by measuring luminescence on a plate reader (Tecan). IC50 values of the 5 drug formulations were estimated using sigmoidal regression in Prism (GraphPad Software, Inc.) and compared using an extra sum-of-squares F-test ($\alpha=0.05$).

Example 49

Preparation and Composition Characterization of Electrospinning Solutions

The salient properties of PVP or PEO solutions prepared with maraviroc are available in a supplementary table (Supplementary Table 1). PVP solutions loaded with maraviroc re mostly transparent, colorless, and viscous. The PVP solution containing both Tween 20 and 40% wt drug/wt polymer, however, developed a white colloidal haze upon storage without continuous mixing for 1 week, suggesting saturation of the maraviroc in the ethanol-based solution. The viscosity, conductivity, and surface tension of each solution were measured. The null hypothesis of no difference between PVP polymer solution parameters with and without Tween 20 is tested using paired, two-sided T-tests with $\alpha=0.05$. There was a significant decrease (95% CI=−0.15 to −0.23) in the viscosity of solutions with Tween 20 compared to solutions without Tween 20 at the same maraviroc concentration. There is a significant increase (95% CI=0.12 to 0.42) in the conductivity of solutions with Tween 20 compared to solutions without Tween 20 at the same maraviroc concentration. There is a slight decrease in surface tension with the inclusion of Tween 20, but the decrease was not statistically significant (P=0.12). This decrease in surface tension may be related to the decrease in viscosity; both characteristics may depend upon how strongly neighboring ethanol molecules cohere to one another. A Pearson's correlation test is run on conductivity data for polymers with and without Tween 20 as a function of maraviroc concentration in % wt drug/wt polymer. Correlations were strong and positive in both cases, and statistically significant correlations were found (P<0.05). Therefore, increasing maraviroc content correlates with increased conductivity of PVP solutions. Interestingly, this positive correlation appears to cease at or below 30% wt drug/wt polymer loading in solutions with Tween 20 (but not those without), suggesting that a solubility limit has been reached. Fewer maraviroc-associated trends are apparent in PEO formulations. Conductivity increased with the addition of Tween 20 (paired T-test, P=0.0248). Conductivity also increases with maraviroc concentration (strong correlation, R=0.84, p=0.002). No trends in viscosities were apparent. The surface tension of all formulations was constant around 40 mN/m, so Tween 20 had no effect on surface tension in PEO formulations.

Example 50

Electrospinning and SEM Characterization

All PVP solutions containing maraviroc produced electrospun fibers. Properties of electrospun PVP fibers are provided in a supplementary table (Supplementary Table 2). PVP fiber diameter appears to decrease with increasing maraviroc concentration for formulations without Tween 20. The addition of Tween 20 to maraviroc-free fibers caused a large reduction in fiber diameter, most likely due to the drop in solution viscosity, but potentially also due to increased conductivity and reduced surface tension. When maraviroc is added to formulations containing Tween 20, the median fiber diameter plummets. In fact, SEM images revealed that fibers containing both polysorbate-20 and maraviroc had two distinct fiber populations: large fibers with diameters ~2000 nm, and small fibers with diameters ~400 nm (hence the high coefficient of variation). Since half of the fibers had a diameter above ~600 nm, the majority of the sample mass was present within the larger fiber population. This two-population behavior was only present when maraviroc was added to PVP-Tween 20 solutions in ethanol. Material efficiency remained high for all formulations (88-94% recovery of polymer). The basis weight of PVP fiber materials was X $gsm^2$.

Similarly, all PEO solutions containing maraviroc produced electrospun fibers. Properties of electrospun PEO fibers are provided in a supplementary table (Supplementary Table 2), and representative SEM micrographs of fibers loaded with ~30 wt % (final concentration in the dry fiber formulations produced from 40% wt drug/wt polymer solutions). All PEO fibers had narrow size distributions, irrespective of Tween 20 content. While increasing maraviroc content led to higher solution conductivity in all PEO solutions, median fiber diameter did not decrease with increasing maraviroc concentration. Rather, fiber diameter steadily increased with maraviroc content in fibers without Tween 20 (two-sided Pearson's correlation with α=0.05, strong correlation, R2=0.95, P=0.0042). This increase suggests that physical characteristics other than viscosity, conductivity, and surface tension (which might predict a decrease in diameter with loading) caused fiber size to increase by hundreds of nanometers with increasing maraviroc content. In samples containing Tween 20, fiber diameter increased until 16 wt % maraviroc loading, then remained fairly constant at ~600 nm. SEM micrographs of electrospun fibers without Tween 20 revealed a friable surface appearance of fibers with high maraviroc loading, while fibers containing Tween 20 displayed a smooth, highly fused surface morphology.

Material efficiency remained high for all formulations. The basis weight of PEO fiber materials was X $gsm^2$.

Example 51

Measuring Drug Loading by HPLC

Results from drug loading analysis by HPLC confirm that nearly 100% of the dissolved drug in electrospinning solutions was loaded into electrospun fibers. Detailed drug loading data are presented as supplemental data (Supplementary Table 3). Electrospinning has been shown to encapsulate nearly 100% of loaded drugs into fibers when the spinning process is stable, but drugs may be lost if there is dripping from the nozzle, off-target fiber collection, phase separation of the drug in solution, or adsorption of the drug onto the syringe or nozzle of the electrospinning setup. Our HPLC analysis of dissolved fiber samples confirmed that loading efficiency was around 100%. Spiked samples of blank PVP fibers had a mean maraviroc recovery of 108.52% (SD=0.53%, n=2) maraviroc recovery, suggesting that PVP increased the observed UV absorbance signal from maraviroc in the HPLC method used to determine loading by ~8.5%. Data normalized to spiked controls from drug loaded PVP fibers suggested that almost the entire amount of drug present in PVP solutions was formulated into electrospun fibers (94.2%±1.2%, n=8), despite apparent colloidal drug suspension in vials containing both Tween 20 and 40% wt drug/wt polymer maraviroc. Spiked samples of blank PEO fibers had a mean maraviroc recovery of 86.45% (SD=0.17%, n=2), suggesting that PEO reduced the observed UV absorbance signal from maraviroc in the HPLC method used to determine loading by ~13.5%. Data normalized to spiked controls from drug loaded PEO fibers suggested that almost the entire amount of drug present in PEO solutions was formulated into electrospun fibers (98.0%±1.8%, n=8). Solutions formulated with 10%, 20%, 30%, and 40% wt drug/wt polymer yielded fibers with 9 wt %, 17 wt %, 23 wt %, and 28 wt % maraviroc content. For convenience, we henceforth refer to the 9 wt % and 28 wt % formulations as 10 wt % and 30 wt % fibers. Final Tween 20 content in fibers spun from 4% wt Tween/wt polymer solutions ranged from 3.7 wt % to 2.5 wt %, decreasing with increasing maraviroc content.

Example 52

Thermal Analysis by Differential Scanning Calorimetry (DSC)

DSC analysis of PVP fibers containing maraviroc revealed that the drug was amorphously distributed throughout the electrospun fibers. No drug endotherm was present in PVP fibers irrespective of Tween 20 content. Only broad endotherms corresponding to the evaporation of atmospheric water from the samples, which are hygroscopic and can absorb up to 5 wt % water from air, were observed around 80-120° C. The Tg of PVP (around 160° C.) was not apparent in these materials, although PVP does not always display an obvious glass transition. While no endotherms corresponding to crystalline maraviroc were identified in PVP samples, such drug-associated endotherms were apparent in PEO fibers.

All PEO fibers possessed a strong endotherm near 66° C. corresponding to the Tm of PEO. The integrated specific heats of fusion from PEO endotherms were used to confirm PEO wt % in samples as an internal control, and PEO wt % estimates agreed well with predicted values (mean percent error=−4.7%±3.9%, n=10). The Tm of PEO was negatively correlated with maraviroc content in fibers (Pearson's R=−0.97, −0.89; P=0.0048, 0.11; n=5, 4; for fibers without and with Tween 20, respectively) and decreased by about 2° C. as maraviroc content went from 0 wt % to 30 wt %. This data provides evidence for significant plasticization of PEO by maraviroc. Tween 20 had no effect on PEO's Tm in this study. All PEO fibers containing maraviroc displayed melting endotherms near the measured melting temperature of pure maraviroc. The Tm of maraviroc was positively correlated to maraviroc loading in fibers (Pearson's R=0.95, 0.95; P=0.046, 0.053; n=5, 5; for fibers without and with Tween 20, respectively), and increased by 12° C. as maraviroc content went from 10 wt % to 30 wt %. This data provides evidence that maraviroc crystalline domains are expanding or becoming more homogenous as maraviroc loading increases. PEO fibers loaded at 10 wt % maraviroc displayed only slight drug crystallinity (Supplementary Table 4), suggesting that at loadings near 10%, the majority of the maraviroc is in the amorphous state. There was a significant, positive correlation between drug loading and percent maraviroc crystallinity in PEO fibers with and without Tween 20 (two-sided Pearson's correlation test, R>0.95, P<0.05, n=5, 4 respectively). Thus, as drug content increased, so did the relative crystallinity of the maraviroc in fibers. Drug crystallinity appeared to peak at ~70% in PEO fibers above a loading of 23 wt %. There was a greater degree of maraviroc crystallization in PEO fibers containing Tween 20. A two-sided paired T-test (paired by matching drug content), comparing maraviroc % crystallinity between fibers with and without Tween 20 showed ~9.9% greater crystallinity in fibers containing Tween 20 (95% CI=1.3% to 18.4%, P=0.035, n=4). Small exotherms suggestive of maraviroc recrystallization (near 120° C.) were present in many PEO fibers containing drug, but they were too minute to accurately integrate and quantify (software fitting would not converge). Thus, estimates of maraviroc crystallinity may be slightly overestimated. Overestimation of drug crystallinity may increase with drug loading, since exotherms were larger, albeit still unquantifiable, at higher loading levels. A Tween 20 peak was observed in neither PEO nor PVP samples, and a DSC thermogram of pure Tween 20 was not obtained due to concerns about possible boiling, which could foul the measurement surface of the DSC instrument.

Example 53

Fiber Surface Analysis by X-Ray Photoelectron Spectroscopy (XPS)

XPS of electrospun fibers was used to estimate the degree of enrichment of maraviroc and Tween 20 at the surface (top 10 Å) of electrospun fibers. Atomic % data for C, N, O, and F showed that the content of maraviroc on the surface depends upon the polymer type, the drug loading, and whether or not Tween 20 was included in the formulation. PEO fibers without Tween showed the highest surface concentrations of maraviroc, reaching 100% maraviroc at 17 wt % loading. Then came PVP with Tween 20, which reached 100% maraviroc at the surface at 30 wt % loading. Neither PEO with Tween 20 nor PVP without Tween 20 had extremely high surface concentrations of maraviroc when loaded at 30 wt %. Nevertheless, these materials showed an approximately 2-fold enrichment of MVC on the surface of the fibers over expected values for a theoretical fiber with a radially homogeneous distribution of maraviroc. Pure PVP fibers and PVP fibers with Tween 20 were compared by subtracting atomic % O, and based on the 95% confidence intervals after error propagation, Tween 20 was enriched 4.8 to 7.8-fold on the surface of PVP fibers without maraviroc.

Example 54

Determination of In Vitro Maraviroc Solubility Following Release from Fibers

The solubility limits of maraviroc following incubation of fibers or pure drug in pH 4.0 citrate buffer are shown. A one-way ANOVA was used to test the null hypothesis that drug solubility was equivalent across all formulations of MVC. We found that drug solubility was not the same for all formulations (P=0.0015). The solubility limit of pure maraviroc in the absence of polymer or surfactant was 21.3±6.4 mg/mL. No significant difference was found between solubility of maraviroc from pure drug and after release from PVP fibers with or without Tween 20 using a Dunnett's multiple comparisons post test (P>0.05), although there appears to be a trend toward slightly lower drug solubility. However, there was a very significant decrease (P<0.01) in drug solubility after release from PEO formulations with or without Tween 20.

Example 55

In Vitro Drug Release into Sink Conditions, In Vitro Dissolution of Electrospun Fibers on a Moist, Porous Surface Drug release into sink conditions at pH 4.0 was evaluated for PVP and PEO fibers loaded with 10 wt % or 30 wt % maraviroc. The time to 100% release of maraviroc from 30 wt % drug materials was 14 min, 6 min, 18 min, and 6 min for PVP, PVP+Tween 20, PEO, and PEO+Tween 20 fibers, respectively. All 10 wt % formulations released 100% of the maraviroc within 2-4 min, except for 10 wt % maraviroc in PEO with Tween 20, which required 10 minutes to fully release maraviroc. PVP fibers thus released maraviroc more rapidly than PEO fibers, and release rate (in terms of % drug release) decreased with increased drug loading. Highly loaded fibers containing Tween 20 released maraviroc much more rapidly than those fibers without Tween 20. The rate of drug release from fibers was also compared to the rate of pure maraviroc dissolution and release in sink conditions in vitro. Micronized maraviroc particles dissolved completely within 2 minutes despite being crystalline, while it took a full 20 minutes to dissolve 90% of a 2 mm diameter crystal of maraviroc. Spiked drug controls yielded full drug recovery at the 2 min time point.

All fibers were easily visualized as white materials on a black background using 1% India ink agar plates. Fiber dissolution was rapid, despite not being immersed in a bath of fluid and not applying pressure to fiber samples on the agar plates. Fibers containing 10 wt % maraviroc significantly hydrated, shrank, or dissolved in less than 10 seconds. Fibers containing 30 wt % maraviroc had slower hydration rates, and displayed two distinct behaviors depending upon Tween 20 incorporation. Those fibers without Tween 20 absorbed water and rapidly contracted within 30 s. This material then continued to swell and dissolve over 20 minutes, at which point the resulting hydrogel could flow if the agar plate were tipped at an angle. A presumably colloidal, white suspension, believed to be undissolved maraviroc, was present in this gel. Those fibers with Tween 20 displayed different behavior. Fibers containing Tween 20 hydrated more rapidly than fibers without Tween 20. Between 5 s and 30 s, the fibers dissolved in place without significant matrix contraction or shrinkage. By the end of the 20 min monitoring period, no colloidal maraviroc or undissolved polymer was visible.

Example 56

In Vitro Anti-HIV Activity of Dissolved Electrospun Fibers

The antiviral activities of pure maraviroc and maraviroc released from electrospun formulations are demonstrated. The dose-response assay with TZM-bL cells shows equivalent bioactivity of all maraviroc tested. The estimated IC50 values for each individual dose-response curve were not significantly different from one another, as tested using an extra sum-of-squares F-test (P=0.924). The globally shared best fit IC50 value for maraviroc was found to be 6.96 ng/mL, or 13.5 nM, which is consistent with previous findings using this in vitro assay.

Example 57

Summary and Discussion

The highly loaded materials used in this study were electrospun using a benign process with high productivity and material efficiency. Spun from a base of alcohol, the PVP electrospinning process used would be environmentally benign and pose little risk to human health during production if scaled up to industrial production. In contrast, many electrospun materials require the use of hazardous organic solvents for their creation [38]. In addition to solvent safety, no high temperatures were needed to create these materials, and electrospinning proceeded at ambient conditions (19-23° C., 50-70% RH). Although electrospinning relies upon high voltage, spinning requires a very low current and therefore little energy. The materials in this study were successfully loaded with up to ~30 wt % maraviroc. HPLC measurements were used to validate loading, and loading was also validated through release assays and partially through thermal measurements (PEO only). Increased drug loading did not destroy productivity. The material efficiency was high (88-94% for PVP materials), and fibers were produced on the bench top with a single nozzle rig at a rate of ~7 mg/min. This process could be scaled up using industrial electrospinning systems.

Described herein are methods that result in good fiber formation by electrospinning 1.3 MDa PVP at 12% w/v in ethanol at rates of up to 100 µL/min. Less concentrated PVP solutions yielded beaded fibers at 50 µL/min or 100 µL/min. These results suggest that an increase in flow rate may require an increased number of chain entanglements to allow for defect-free fiber formation. Interestingly, including a charged metal screen at the base of the electrospinning nozzle had a dramatic effect on the size and morphology of the PVP fibers in our study. We observed that the length of the electrospinning jet extending from the nozzle was much longer when using the unidirectional electric field. This suggests that the uniform electric field reduced the amount of whipping due to jet instability, resulting in a larger diameter fiber. At the same time, the fibers took on a slightly wrinkled appearance. The increased length of the jet's stable region also explains why wet polymer was deposited onto the substrate at flow rates of 100 µL/min. The reduced whipping occluded complete ethanol evaporation. PEO fibers were spun from a mixture of ethanol and water in order to solubilize both components. In general, it was observed that higher flow rates of 25 and 50 µL/min produced beaded fibers. While higher PVP concentrations allowed for greater production speed, increasing the concentration of PEO to 4% resulted in the deposition of wet material on the collector surface at flow rates higher than 10 µL/min.

Example 58

Effect of Crystallinity

The crystallinity of maraviroc in electrospun materials had an insignificant impact on the dissolution of maraviroc into pH 4 media on the time scale of 15 minutes, likely due to the small physical size of existing crystals. Within pharmaceutics, it is often the case that drugs with melting temperatures above 200° C. will display improved solubility and release rates when formulated into amorphous solid dispersions. The melting point of crystalline maraviroc is near 195° C., suggesting that drug-drug interactions within crystalline maraviroc may significantly retard the dissolution of the drug.

To observed how maraviroc's crystallinity affected release from electrospun fibers, the Inventors compared PVP and PEO polymer fibers' performance. Inventors' other result show that maraviroc exists in a semicrystalline state within PEO fibers even at loadings near 1 wt %, and PVP is often used to create solid amorphous dispersions of drugs to accelerate release or increase apparent drug solubility in both electrospun fibers and oral tablets. If amorphous maraviroc truly dissolves far more rapidly than crystalline maraviroc, then one expects materials with more crystalline maraviroc to release drug more slowly than those with less crystalline maraviroc, all other material characteristics being equal.

Crystalline maraviroc was only found in PEO fibers, suggesting that PVP indeed had better molecular compatibility with maraviroc. The melting temperature of maraviroc increased with maraviroc loading in PEO fibers, suggesting increasing size or homogeneity of maraviroc crystalline domains. At the same time, the melting temperature of PEO fibers decreased with increased maraviroc loading, suggesting increased plasticization of the polymer by maraviroc. The percentage of maraviroc in fibers that was crystalline increased from ~20% to ~70% as loading increased from ~10% to ~30%, so a comparison might be made between PEO fibers with high and low drug loading. One can evaluate the dissolution characteristics of pure maraviroc crystals to assess whether or not they dissolved "slowly" (in this case meaning >15 min). In fact, crystalline maraviroc dissolved in around 20 minutes when the maraviroc was in a single, large crystal with a diameter of around 2 mm. However, nanoparticulate crystalline maraviroc prepared by grinding crystals with a mortar and pestle into particles ranging in size from X nm to X µm dissolved in less than 2 minutes in citrate buffer (pH 4.0). These observations imply that as long as the size of the crystalline domains is small, the dissolution of maraviroc will not likely be slow due to the crystalline state of the drug. Physical dispersion of drug crystals increases the surface area to volume ratio, reducing the effects of drug-drug interactions on solubilization kinetics. While an amorphous drug may indeed dissolve more rapidly for the equivalently sized piece of maraviroc, there is little practical need to develop such a formulation.

Example 59

Application of Surfactants

Surfactants could help solubilize and disperse drug during both the electrospinning and delivery phases. Inclusion of the surfactant Tween 20 into polymer fibers may increase the stability of drug-water interactions during initial dissolution of the fiber matrix. Many drugs are poorly soluble due to unfavorable interactions between nonpolar regions of the drug and polar water molecules. Water molecules at the interface of a nonpolar surface must take on an awkward clathrate water configuration that reduces entropy, driving the drug out of solution. Surfactants are amphiphilic, and can serve as a bridge between hydrophobic drugs and polar solvents like water. The described results suggest that Tween 20 does significantly enhance the rate of maraviroc release from electrospun fibers, although it has no effect on drug solubility when incubated at body temperature for 24 h. The use of surfactants in a microbicide formulation is a sensitive issue, as surfactants may be toxic to epithelial tissue. Increased risk for HIV infection can result from repeated epithelial disruption by detergents such as nonoxynol-9. Therefore, it is of paramount importance to select a surfactant that poses little to no risk to vaginal and cervical tissue when applied topically.

One strategy is to select surfactants based on their hydrophilic-lipophilic balance, which can be used to classify surfactants as detergents, wetting agents, emulsifiers, etc. Tween 20 is a common wetting agent that may be useful for increasing the rate of drug release, and could have a high threshold for toxicity in vivo. Tween 20 has a hydrophilic-lipophilic balance of 16.7, which makes it a hydrotope. Tween 80 has a hydrophilic-lipophilic balance of 15, making it a detergent (non-ionic detergent). For comparison, nonoxynol-9 has a balance of 13, and is also a detergent (ionic detergent). There is precedent for the safe repeated use of Tween 20 in vaginal formulations. The gel Conceival (a potential microbicide for lipophilic drug delivery) contains 2-4 wt % Tween 20 and is nontoxic in rabbits and to rabbit and human sperm. The in vivo toxicity of electrospun fibers containing low amounts of Tween-20 remains to be evaluated.

Example 60

Conclusions

Electrospun PVP fibers can deliver a high dose of maraviroc intravaginally within minutes following application. Maraviroc is currently a lead antiretroviral compound for formulation into an anti-HIV topical microbicide. It is highly potent against CCR5-tropic viruses, and has no major side effects. Based on clinical and preclinical studies of the drug's pharmacokinetics and ability to prevent viral transmission, it seems likely that maraviroc will be most effective when incorporated into a microbicide platform that allows for a rapid release of high levels of maraviroc at or above its usual solubility limit within 30 minutes before viral challenge followed by a sustained release for at least 24 hours to ensure that protective levels are maintained and that protection is not entirely coitally dependent. In particular, the microbicide product should act locally, achieve high vaginal retention, minimize leakage, and permit coformulation with other APIs. Future work will investigate composites of electrospun fiber materials can fulfill these requirements. Our current work demonstrates the need for rigorous physical and chemical characterization of new materials in order to better engineer such novel anti-HIV vaginal microbicides.

Example 61

Methods for Electrospinning Co-Axial Spun Fibers

Exemplary materials, such as PVP K60 (Mw=360; 000) or ethyl cellulose, EC, (6 mPa s to 9 mPa s) can be applied in the production of co-axial spun fibers. Core solutions re prepared by dissolving 24 g EC, a quantity of a drug agent and 2 mg methylene blue in 100 ml ethanol. The sheath solution was prepared by placing 9 g PVP and 1 g KET in 100 ml of a solvent mixture of DMAc and ethanol in a volume ratio of 1:9. Two syringe pumps and a high-voltage power supply can be used for coaxial electrospinning. All electrospinning processes were carried out under ambient conditions (22±3 $^1$C with relative humidity 58±5%). In certain variations, a concentric spinneret can be applied to conduct both single fluid (adjusting the core or sheath fluid flow rate to 0 ml $h_1$ 1) and coaxial electrospinning processes, further including techniques readily understood to one of ordinary skill in the art, such as that described in Yu et al., "Electrospun biphasic drug release polyvinylpyrrolidone/ethyl cellulose core/sheath nanofibers" *Acta Biomaterialia* 9, 5665-5672 (2013) and Wu et al., "Effect of Solvent on Morphology of Electrospinning Ethyl Cellulose Fibers" *Journal of Applied Polymer Science*, 97, 1292-1297 (2005), which are fully incorporated herein by in their entirety.

Example 62

Co-Axial Spun Fibers for Sustained Release

Although 48-hour release of maraviroc from uniaxial ethyl cellulose fibers is achieved using the described methods, 75% of the encapsulated maraviroc is released within 6 hours in a pH 4.2 acetate buffer. As ethyl cellulose has been useful for sustaining drug release, it is of interest to evaluate the use of ethyl cellulose as a polymer shell for sustained drug release from core-shell fibers.

Figure 30:
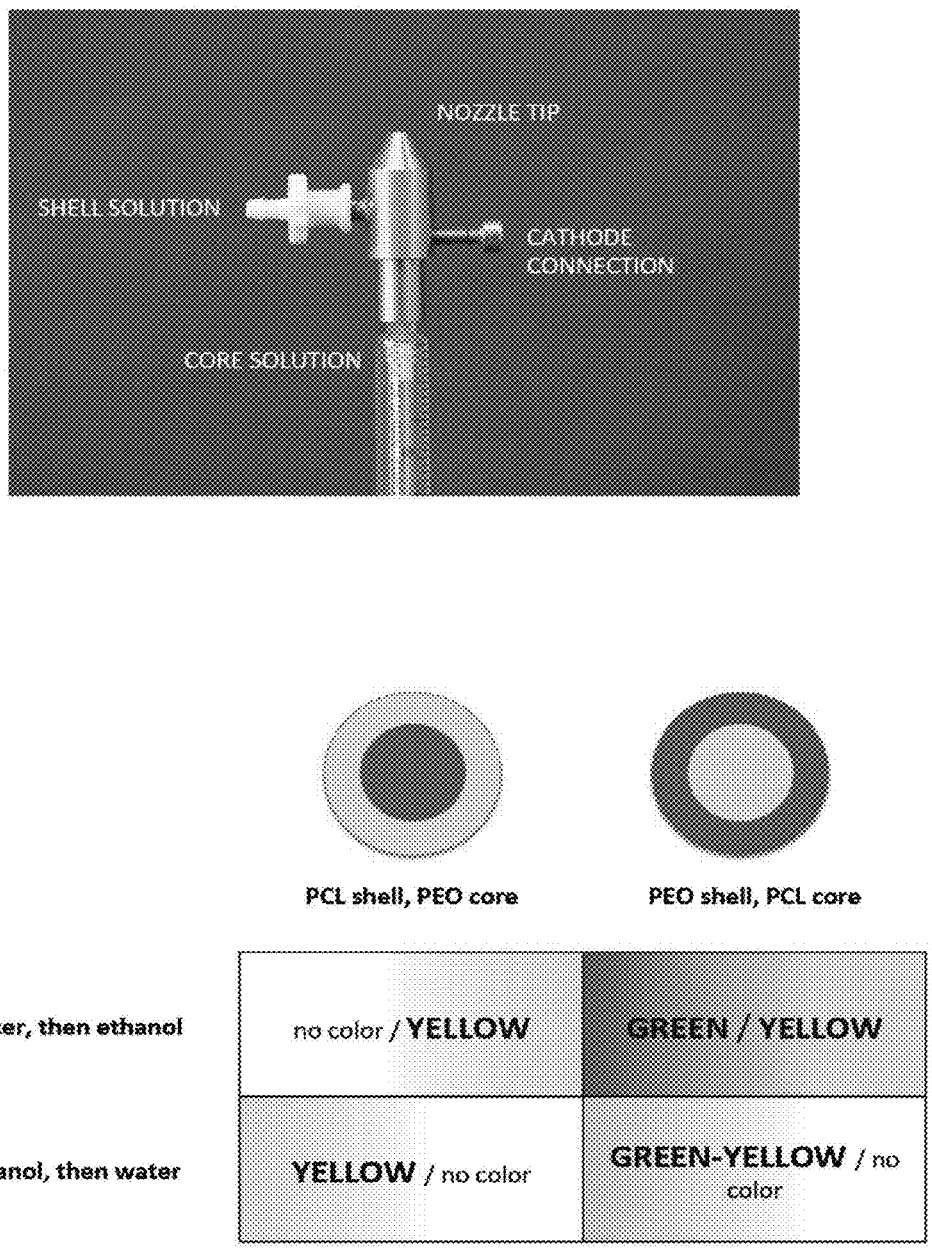
FIG. 30 Co-axial electrospun fibers. Top panel, Fabricated nozzle with a bore of 2/0.413 mm was used to spin fibers containing Bottom panel, Polycaprolactone in 2,2,2-trifluoroethanol with 1% coumarin 6•Polyethylene oxide in H2O with green food coloring.

A custom fabricated co-axial nozzle is shown in FIG. 30, top panel, allowing for generation of electrospun fibers containing variable solution compositions, such as the example shown in FIG. 30, bottom panel. Applying this technique, One can apply a solution of PVP and maraviroc in ethanol as the core solution, and a 16% solution of ethyl cellulose in trifluoroethanol as the shell solution using the nozzle for co-axial fiber generation. Both solutions are extruded from the coaxial nozzle at a high flow rate of 50 μL/min, yielding a theoretical drug loading of approximately 15 wt %. The fibers re thick and white, with a basis weight of around 60 gsm and a thickness of 1-2 mm.

Fibers are cut into triplicate, regular circles with a steel die (mass ~13 mg) and immersed in a bath of pH 4.0 citrate buffer at 37° C. Samples are tumbled continuously at 7 rpm on a rotisserie shaker. 50 μL samples were collected at set time points out to 24 hours, and analyzed by HPLC to quantify drug release.

Figure 31:
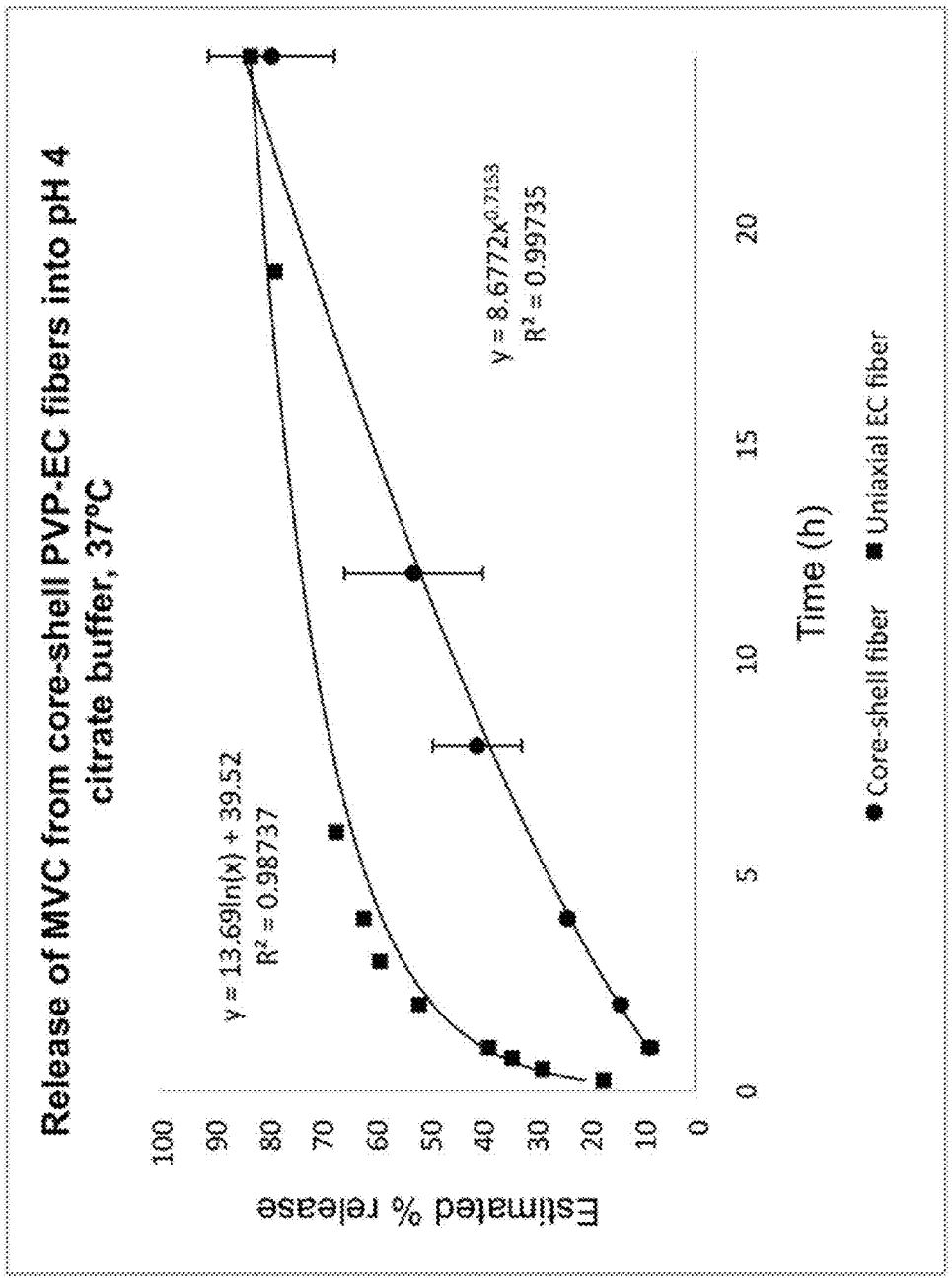
FIG. 31. Release of MVC from core-shell PVP-EC fibers. The results showed a vast decrease in the release rate from fibers compared to PVP-maraviroc fibers without an ethyl cellulose ("EC") shell (release in 6 minutes), and improvement over release from uniaxial ethyl cellulose fibers.

The results showed a vast decrease in the release rate from fibers compared to PVP-maraviroc fibers without an ethyl cellulose shell (release in 6 minutes), and improvement over release from uniaxial ethyl cellulose fibers, as shown in FIG. 31. Fibers swelled to 200-300% of their dry mass in water over 24 hours.

Example 63

Electrospun Fiber of Ethyl Cellulose

Ethyl cellulose ("EC") is a cellulose ether with good thermostability and non-toxic properties. The film made from EC has good permeability, it has been widely used in the biomedical field. The fiber produced by electrospinning has a large specific surface, which broadens the possible uses of EC. Furthermore, with a Tg of 130-150° C., EC is a highly or fully amorphous materials that is a thermotropic liquid exhibiting crystalline behaviors. Interestingly, EC fabrics are brittle and shatter into "snowflake"-like or nanoparticulates, which may persist in tissues to provide sustained drug release.

In order to exploit these features of EC-based fabrics, the Inventors further explored the possibilities of using materials such as EC for delivery of drugs such as dapivirine ("DPV"), a nonnucleoside reverse transcriptase inhibitor which possesses prolonged inhibitory effects against HIV, as reportedly able to prevent both localized and disseminated infection for as long as 6 days posttreatment. Importantly, DPV is a tight-binding inhibitor of HIV RT it is likely that the prolonged inhibitory effect is due to the association of sufficient drug with the tissue following compound removal. However, DPV is particularly hydrophobic, and its effective application can be enhanced by a sustained drug release system.

Figure 32:
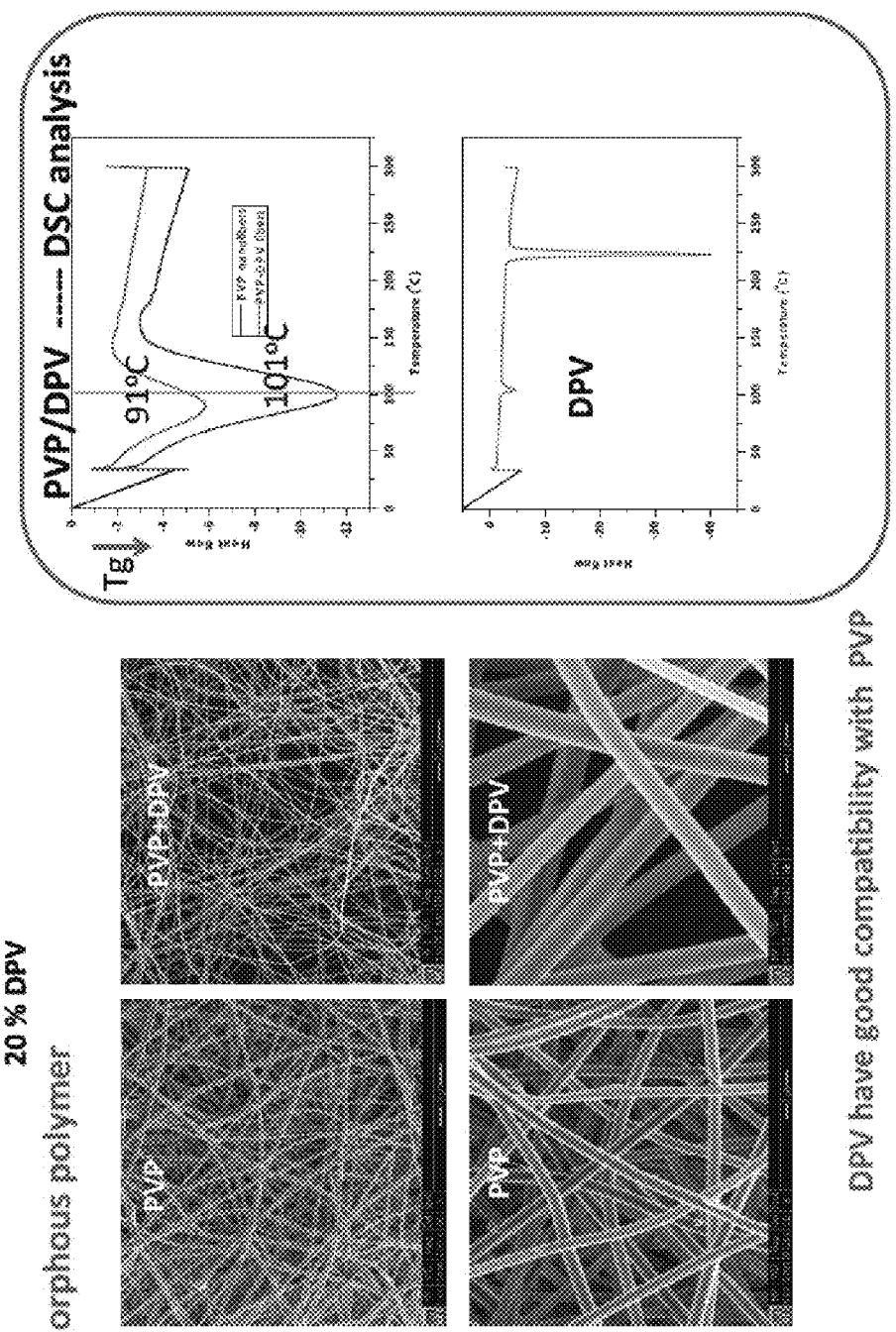
FIG. 32 DPV compatibility with PVP fibers. As shown, dapivirine ("DPV") has good compatibility with electrospun PVP fibers, as shown in SEM images, and DSC measurements.
Figure 33:
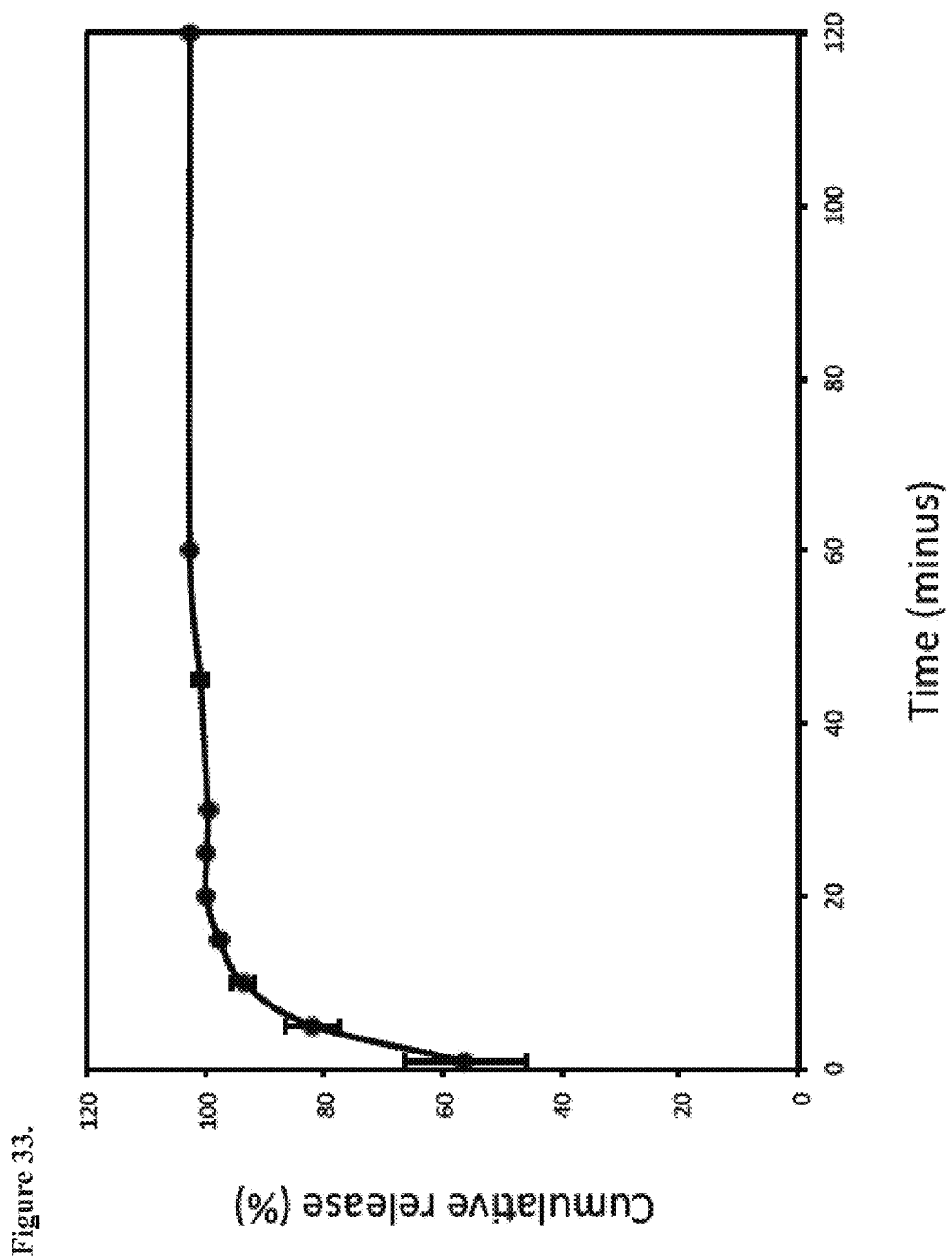
FIG. 33 DPV burst-release release characteristics. Burst release characteristics were also observed from PVP fibers.

In this regard, the Inventors explored alternative materials, such as PVP, EC and combinations thereof, to evaluate their potential application in sustained release applications. As shown in FIG. 32, DPV has good compatibility with electrospun PVP fibers, as shown in SEM images, and DSC measurements. DPV burst-release release characteristics were also observed from PVP fibers, as shown in FIG. 33.

Figure 34:
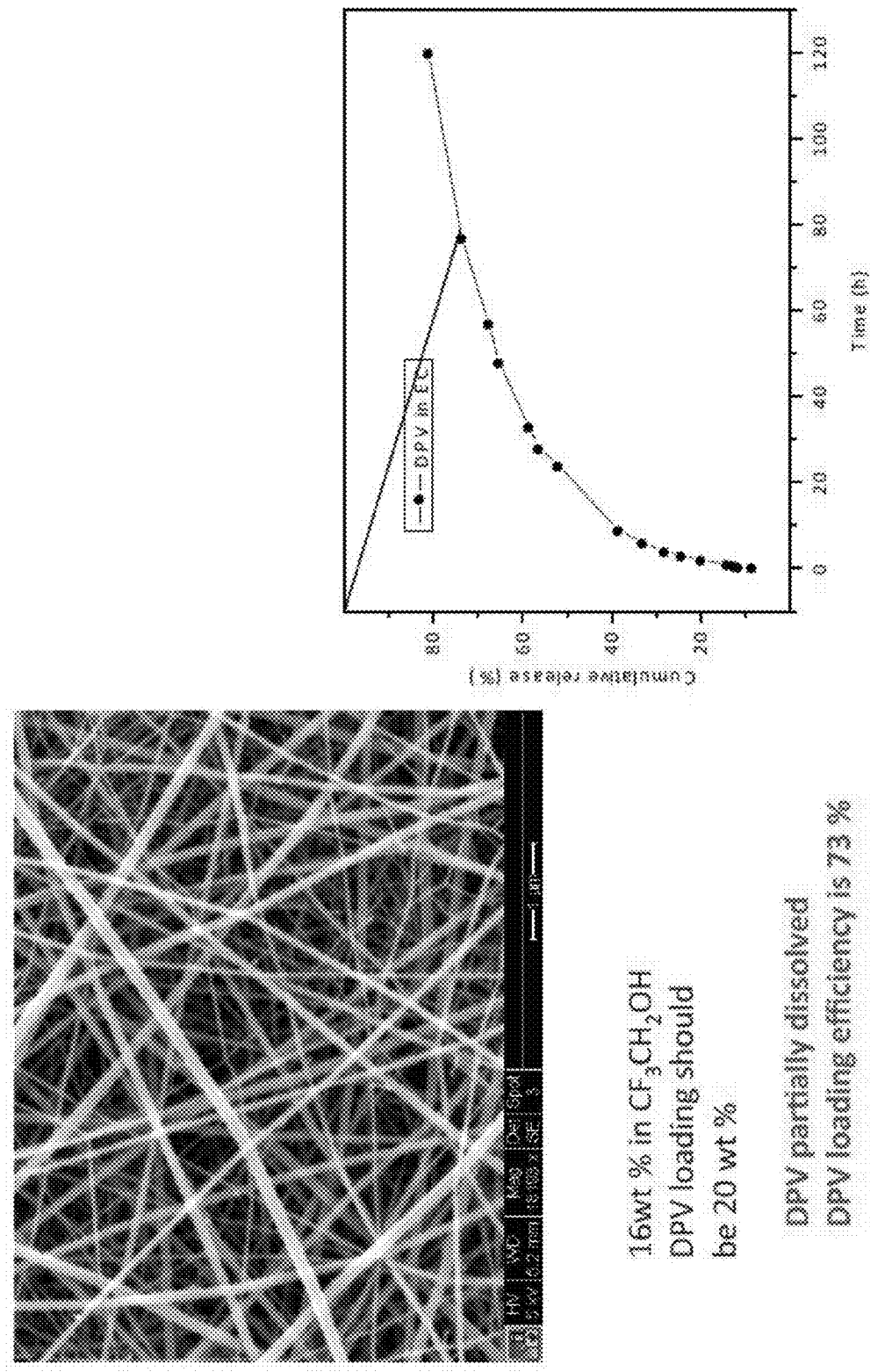
FIG. 34 Application of DVP in electrospun EC fibers. A sustained release of DPV was observed from EC fibers.
Figure 38:
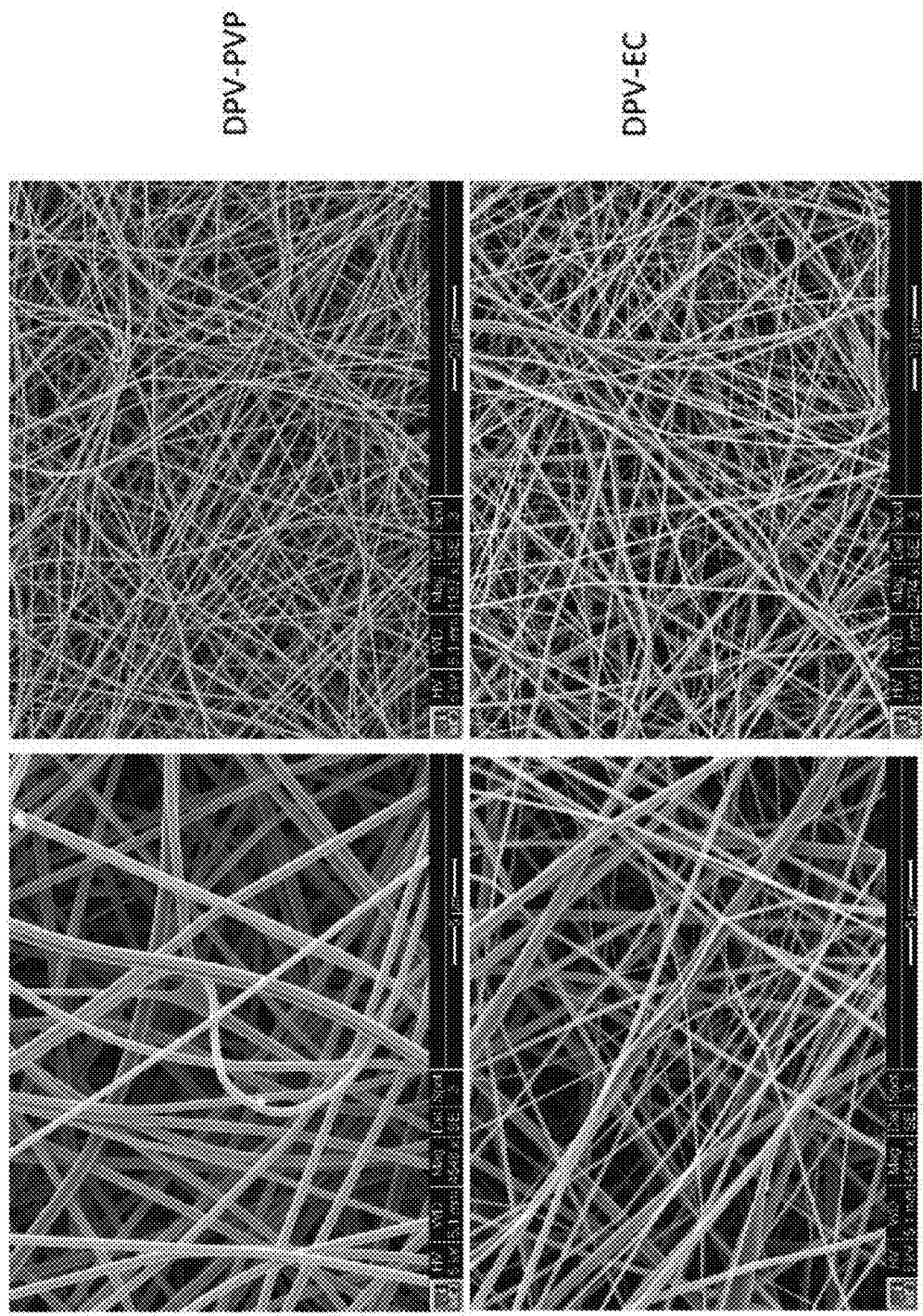
FIG. 38 SEM images demonstrating properties of combination materials. As shown, combination materials in layers of EC and PVP mats.

Extending these results, the Inventors observed the application of DVP in electrospun EC fibers. DPV at a concentration of 20 wt. % was observed to partially dissolve in EC fibers, with a loading efficiency of approximately 73% (FIG. 34). Thermal behaviors for EC, EC-DPV, and DPV combinations were measured, demonstrating the release characteristics of DPV from EC fibers (FIG. 35, top panel), and SEM images of DPV loaded in to electrospun EC fibers demonstrated structural integrity of the produced fibers (FIG. 35, bottom panel). In addition the Inventors measured the potential compatibility of PVP and EC fibers for (FIG. 36, top panel) and DPV release characteristics when the materials are combined together (FIG. 36, bottom panel). Importantly, the morphology of PVP-EC mats after DPV release (FIG. 37, top panel) demonstrated no apparent shrinkage and no pores on the fibers (FIG. 37, bottom panel). Additional SEM images demonstrate the compatibility of EC and PVP mats (FIG. 38), as well and thermal behaviors (FIG. 39, top panel) providing variable release behaviors (FIG. 39, bottom panel).

TABLE 1

Composition and solution properties of fiber formulations.[a]

| Fabrics | Density (g/mL) | Conductivity (μS/cm) | pH | Viscosity[b] (Pa*s) | Surface Tension (mN/m) |
|---|---|---|---|---|---|
| PVA Only | 1.10 | 573 | 5.58 | 0.45 | 59.0 |
| LNG Only (20 wt. %) | 1.12 | 649 | 5.58 | 0.46 | 58.0 |
| TFV Only (20 wt. %) | 1.08 | 527 | 3.85 | 0.53 | 59.4 |
| Combined TFV/LNG (10 wt. % each) | 1.05 | 438 | 4.01 | 0.45 | 55.3 |

[a]n = 1 for all measurements.
[b]Viscosity is reported at 10 s$^{-1}$.

TABLE 2

Properties of drug-loaded electrospun fibers.[a]

| Fabrics | EE (%), Loading (wt %) | | Fiber Diameter (nm) | Fiber Yield (%) | Productivity (g/m²/hr) | Drug Crystallinity (%) | |
|---|---|---|---|---|---|---|---|
| | LNG | TFV | | | | LNG | TFV |
| PVA Only | — | — | 208 ± 106 | 39.4 | 12.9 | — | — |
| Single Drug Fabrics | | | | | | | |
| LNG Only | 100 ± 1.1 (16.7%) | — | 260 ± 105 | 33.8 | 18.0 | 1.2% | — |
| TFV Only | — | 85 ± 1.3 (14.3%) | 267 ± 176 | 49.9 | 18.0 | — | 0.2% |
| Multidrug Composite Fabrics | | | | | | | |
| Stacked | 114 ± 9.4 (9.6%) | 83 ± 1.1 (6.9%) | 251 ± 107 | 67.9 | 26.6 | n.d. | 0.2% |
| Interwoven | 166 ± 9.6 (13.9%) | 44 ± 2.4 (3.7%) | 303 ± 123 | 31.9 | 16.8 | n.d. | n.d. |
| Combined | 82 ± 1.5 (11.6%) | 93 ± 1.9 (14.3%) | 251 ± 83 | 39.7 | 18.7 | n.d. | 2.3% |

[a] n = 3 for drug encapsulation efficiency, n = 45 for average fiber diameter, values represent mean ± s.d.

[b] n = 1 for yield, productivity, drug crystallinity.

[c] Drug loading (shown in parentheses) is expressed as wt. drug/wt. fiber.

n.d. = not detected.

SUPPLEMENTARY TABLE 1

Properties of PVP or PEO solutions containing maraviroc.

| Polymer | Tween 20 concentration (% wt Tween/wt polymer) | MVC concentration (% wt drug/wt polymer) | Density (g/mL) | Conductivity (μS/cm) | η (Pa·s) | γ (mN/m) |
|---|---|---|---|---|---|---|
| PVP | 0 | 0 | 0.86 | 0.86 | 0.87 | 32.0 |
| PVP | 0 | 10.30 | 0.86 | 1.94 | 0.94 | 32.2 |
| PVP | 0 | 20.38 | 0.87 | 2.24 | 0.89 | 32.5 |
| PVP | 0 | 30.30 | 0.86 | 2.61 | 0.92 | 32.9 |
| PVP | 0 | 39.80 | 0.87 | 2.88 | 0.87 | 32.1 |
| PVP | 3.69 | 0 | 0.84 | 1.13 | 0.71 | 31.9 |
| PVP | 3.81 | 10.01 | 0.86 | 2.21 | 0.70 | 32.3 |
| PVP | 3.80 | 20.11 | 0.86 | 2.63 | 0.70 | 32.0 |
| PVP | 3.79 | 30.26 | 0.87 | 2.96 | 0.71 | 30.9 |
| PVP | 3.76 | 39.94 | 0.87 | 2.95 | 0.71 | 30.9 |
| PEO | 0 | 0 | 0.92 | 7.69 | 1.35 | 40.2 |
| PEO | 0 | 10.19 | 0.92 | 8.25 | 1.42 | 40.7 |
| PEO | 0 | 20.42 | 0.92 | 8.95 | 1.34 | 40.7 |
| PEO | 0 | 30.63 | 0.92 | 9.04 | 1.27 | 39.4 |
| PEO | 0 | 40.08 | 0.93 | 9.95 | 1.32 | 39.5 |
| PEO | 3.83 | 0 | 0.93 | 8.88 | 1.52 | 40.2 |
| PEO | 3.59 | 10.08 | 0.92 | 9.13 | 1.45 | 39.5 |
| PEO | 3.80 | 19.87 | 0.92 | 9.18 | 1.29 | 40.4 |
| PEO | 3.74 | 30.40 | 0.92 | 9.82 | 1.27 | 39.2 |
| PEO | 3.52 | 39.84 | 0.92 | 10.18 | 1.30 | 39.6 |

SUPPLEMENTARY TABLE 2

Properties of electrospun PVP or PEO fibers containing MVC and Tween 20. *Fibers seen in SEM had a bimodal distribution of large fibers (~2,000 nm) and small fibers (~400 nm). This behavior was only seen in fibers containing both polysorbate-20 and MVC, and may correlate to decreases in solution viscosity and increases in solution conductivity. Friable morphology apparent in SEM micrographs of fibers. Yield was lower due to equipment failure midway through the electrospinning run. Percent PEO (based on pure PEO fiber specific heat of fusion) Percent error for PEO content (based on predicted PEO content) Percent crystalline MVC (based on pure MVC specific heat of fusion and predicted MVC loading)

| Loadings | | PEO Transition | | | | | Loadings | | MVC Transition | | | | |
| --- | --- | --- | --- | --- | --- | --- | --- | --- | --- | --- | --- | --- | --- |
| MVC (wt %) | Tween-20 (wt %) | Onset temp (° C.) | Tm (° C.) | Specific heat of fusion (J/g) | Percent PEO | Percent error for PEO content | MVC (wt %) | Tween-20 (wt %) | Recrystallization peak near 120° C.? | Onset temp (° C.) | Tm (° C.) | Specific heat of fusion (J/g) | Percent crystalline MVC |
| 100.00 | 0.00 | NA | NA | NA | NA | NA | 100.00 | 0.00 | N | 195.36 | 199.13 | 71.75 | 100.00 |
| 0.00 | 0.00 | 60.95 | 67.15 | 114.80 | 100.00 | 0.00 | 0.00 | 0.00 | N | NA | NA | NA | NA |
| 9.25 | 0.00 | 59.99 | 66.83 | 97.53 | 84.96 | −6.39 | 9.25 | 0.00 | N | 169.64 | 183.68 | 0.69 | 10.39 |
| 16.96 | 0.00 | 56.87 | 66.46 | 92.13 | 80.25 | −3.36 | 16.96 | 0.00 | N | 177.46 | 191.30 | 5.37 | 44.15 |
| 23.45 | 0.00 | 58.17 | 65.92 | 81.06 | 70.61 | −7.76 | 23.45 | 0.00 | Y | 183.06 | 195.39 | 9.93 | 59.04 |
| 28.61 | 0.00 | 58.39 | 65.39 | 71.73 | 62.48 | −12.48 | 28.61 | 0.00 | Y | 192.86 | 195.61 | 12.60 | 61.38 |
| 0.00 | 3.69 | NT | NT | NT | NT | NT | 0.00 | 3.69 | NT | NT | NT | NT | NT |
| 8.87 | 3.16 | 59.81 | 67.20 | 104.30 | 90.85 | 3.28 | 8.87 | 3.16 | N | 166.50 | 182.01 | 1.75 | 27.42 |
| 16.07 | 3.07 | 58.65 | 65.28 | 89.55 | 78.01 | −3.53 | 16.07 | 3.07 | Y | 174.36 | 190.48 | 5.58 | 48.39 |
| 22.66 | 2.79 | 58.37 | 65.11 | 81.39 | 70.90 | −4.90 | 22.66 | 2.79 | Y | 179.80 | 194.45 | 11.28 | 69.37 |
| 27.79 | 2.45 | 58.40 | 64.91 | 81.24 | 70.77 | 1.45 | 27.79 | 2.45 | Y | 190.47 | 194.90 | 13.80 | 69.21 |

SUPPLEMENTARY TABLE 3

Maraviroc loading in PVP or PEO fibers evaluated by HPLC. ND = no MVC detected in sample.

| Polymer | Tween-20 wt % | Predicted MVC loading (wt %) | Measured MVC loading (wt %) rel. to standard curve | Encapsulation efficiency (%) rel. to standard curve | Measured MVC loading (wt %) rel. to spiked samples | Encapsulation efficiency (%) rel. to spiked samples |
| --- | --- | --- | --- | --- | --- | --- |
| PVP | 0 | 0 | ND | ND | ND | ND |
| PVP | 0 | 9.37 | 9.69 | 104.60 | 8.93 | 96.40 |
| PVP | 0 | 16.9 | 17.27 | 102.29 | 15.92 | 94.27 |
| PVP | 0 | 23.1 | 23.26 | 100.66 | 21.44 | 92.76 |
| PVP | 0 | 28.3 | 28.78 | 101.74 | 26.52 | 93.76 |
| PVP | 3.58 | 0 | ND | ND | ND | ND |
| PVP | 3.49 | 8.74 | 8.83 | 100.95 | 8.13 | 93.03 |
| PVP | 3.07 | 16.1 | 16.45 | 101.88 | 15.16 | 93.89 |
| PVP | 2.83 | 22.5 | 23.09 | 102.40 | 21.28 | 94.37 |
| PVP | 2.62 | 27.8 | 28.73 | 103.38 | 26.48 | 95.27 |
| PEO | 0 | 0 | ND | ND | ND | ND |
| PEO | 0 | 9.25 | 7.93 | 85.74 | 9.17 | 99.17 |
| PEO | 0 | 16.96 | 14.64 | 86.34 | 16.94 | 99.87 |
| PEO | 0 | 23.45 | 19.79 | 84.39 | 22.89 | 97.61 |
| PEO | 0 | 28.61 | 24.58 | 85.89 | 28.43 | 99.35 |
| PEO | 3.69 | 0 | ND | ND | ND | ND |
| PEO | 3.16 | 8.87 | 7.24 | 81.59 | 8.37 | 94.37 |
| PEO | 3.07 | 16.07 | 13.90 | 86.5 | 16.08 | 100.06 |
| PEO | 2.79 | 22.66 | 19.03 | 83.95 | 22.01 | 97.11 |
| PEO | 2.45 | 27.79 | 23.28 | 83.76 | 26.93 | 96.88 |

SUPPLEMENTARY TABLE 4

Calorimetric analysis of PEO fibers loaded with MVC, Tween 20, or both. NT = Not tested. Percent PEO (based on pure PEO fiber specific heat of fusion) Percent error for PEO content (based on predicted PEO content) Percent crystalline MVC (based on pure MVC specific heat of fusion and predicted MVC loading)

| Loadings | | PEO Transition | | | | |
|---|---|---|---|---|---|---|
| MVC (wt %) | Tween-20 (wt %) | Onset temp (° C.) | Tm (° C.) | Specific heat of fusion (J/g) | Percent PEO | Percent error for PEO content |
| 100.00 | 0.00 | NA | NA | NA | NA | NA |
| 0.00 | 0.00 | 60.95 | 67.15 | 114.80 | 100.00 | 0.00 |
| 9.25 | 0.00 | 59.99 | 66.83 | 97.53 | 84.96 | −6.39 |
| 16.96 | 0.00 | 56.87 | 66.46 | 92.13 | 80.25 | −3.36 |
| 23.45 | 0.00 | 58.17 | 65.92 | 81.06 | 70.61 | −7.76 |
| 28.61 | 0.00 | 58.39 | 65.39 | 71.73 | 62.48 | −12.48 |
| 0.00 | 3.69 | NT | NT | NT | NT | NT |
| 8.87 | 3.16 | 59.81 | 67.20 | 104.30 | 90.85 | 3.28 |
| 16.07 | 3.07 | 58.65 | 65.28 | 89.55 | 78.01 | −3.53 |
| 22.66 | 2.79 | 58.37 | 65.11 | 81.39 | 70.90 | −4.90 |
| 27.79 | 2.45 | 58.40 | 64.91 | 81.24 | 70.77 | 1.45 |

| Loadings | | | Onset | | Specific | Percent |
|---|---|---|---|---|---|---|
| MVC (wt %) | Tween-20 (wt %) | Recrystallization peak near 120° C.? | temp (° C.) | Tm (° C.) | heat of fusion (J/g) | crystalline MVC |
| 100.00 | 0.00 | N | 195.36 | 199.13 | 71.75 | 100.00 |
| 0.00 | 0.00 | N | NA | NA | NA | NA |
| 9.25 | 0.00 | N | 169.64 | 183.68 | 0.69 | 10.39 |
| 16.96 | 0.00 | N | 177.46 | 191.30 | 5.37 | 44.15 |
| 23.45 | 0.00 | Y | 183.06 | 195.39 | 9.93 | 59.04 |
| 28.61 | 0.00 | Y | 192.86 | 195.61 | 12.60 | 61.38 |
| 0.00 | 3.69 | NT | NT | NT | NT | NT |
| 8.87 | 3.16 | N | 166.50 | 182.01 | 1.75 | 27.42 |
| 16.07 | 3.07 | Y | 174.36 | 190.48 | 5.58 | 48.39 |
| 22.66 | 2.79 | Y | 179.80 | 194.45 | 11.28 | 69.37 |
| 27.79 | 2.45 | Y | 190.47 | 194.90 | 13.80 | 69.21 |

SUPPLEMENTARY TABLE 5

Various compositions produced by the described methods.

| Polymer | | Drug | | | Viscosity | | Surface | |
|---|---|---|---|---|---|---|---|---|
| Type | % w/v solution | Name | wt % solids | Electrode | (Pa · s, 10 s−1) | Conductivity (µS/cm) | Tension (mN/m) | Electrospinnable? |
| PVA | 10 | AZT | ~1 | Needle | 0.5 | 500 | 60 | |
| PVA | 10.57% | TFV | 10 (unadjusted)* | Needle & Nanospider | 0.454 | 201 | 62.5 | Yes |
| PVA | 10.57% | TFV | 60 (unadjusted)* | Needle & Nanospider | 2.515 | 175 | 67 | Yes |
| PVA | 10.57% | TFV | 10 (pH-adjusted)* | Needle & Nanospider | 0.701 | 2,230 | 63.4 | Yes |
| PVA | 10.57% | TFV | 60 (pH-adjusted)* | Needle & Nanospider | 0.457 | 14,940 | 62.3 | Yes |
| PVA | 10.57% | TFV | 80 (pH-adjusted)* | Needle & Nanospider | n.m. | 17,500 | n.m. | No |
| PVA | 10% | LNG | 20 | Nanospider | 0.46 | 649 | 58.0 | Yes |
| PVA | 10% | TFV | 20 | Nanospider | 0.53 | 527 | 59.4 | Yes |
| PVA | 10% | LNG + TFV | 20 (each) | Nanospider | 0.45 | 438 | 55.3 | Yes |
| PVA | 13% | LNG | 1 | Needle | 2.969 | 335 | 72.8 | Yes |
| PVA | 13% | LNG | 10 | Needle | 3.516 | 344 | 72.3 | Yes |
| PVA | 13% | LNG | 40 | Needle | 3.766 | 554 | 68.8 | Yes |
| PVP | | MVC | 0 | Needle | 0.87 | 0.86 | 32.0 | Yes |
| PVP | | MVC | 10.30 | Needle | 0.94 | 1.94 | 32.2 | Yes |
| PVP | | MVC | 20.38 | Needle | 0.89 | 2.24 | 32.5 | Yes |
| PVP | | MVC | 30.30 | Needle | 0.92 | 2.61 | 32.9 | Yes |
| PVP | | MVC | 39.80 | Needle | 0.87 | 2.88 | 32.1 | Yes |

SUPPLEMENTARY TABLE 5-continued

Various compositions produced by the described methods.

| Polymer | | Drug | | | Viscosity | | Surface | |
| --- | --- | --- | --- | --- | --- | --- | --- | --- |
| Type | % w/v solution | Name | wt % solids | Electrode | (Pa · s, 10 s−1) | Conductivity (μS/cm) | Tension (mN/m) | Electrospinnable? |
| PVP | | MVC | 0 (4% Tween) | Needle | 0.71 | 1.13 | 31.9 | Yes |
| PVP | | MVC | 10.01 (4% Tween) | Needle | 0.70 | 2.21 | 32.3 | Yes |
| PVP | | MVC | 20.11 (4% Tween) | Needle | 0.70 | 2.63 | 32.0 | Yes |
| PVP | | MVC | 30.26 (4% Tween) | Needle | 0.71 | 2.96 | 30.9 | Yes |
| PVP | | MVC | 39.94 (4% Tween) | Needle | 0.71 | 2.95 | 30.9 | Yes |
| PEO | | MVC | 0 | Needle | 1.35 | 7.69 | 40.2 | Yes |
| PEO | | MVC | 10.19 | Needle | 1.42 | 8.25 | 40.7 | Yes |
| PEO | | MVC | 20.42 | Needle | 1.34 | 8.95 | 40.7 | Yes |
| PEO | | MVC | 30.63 | Needle | 1.27 | 9.04 | 39.4 | Yes |
| PEO | | MVC | 40.08 | Needle | 1.32 | 9.95 | 39.5 | Yes |
| PEO | | MVC | 0 (4% Tween) | Needle | 1.52 | 8.88 | 40.2 | Yes |
| PEO | | MVC | 10.08 (4% Tween) | Needle | 1.45 | 9.13 | 39.5 | Yes |
| PEO | | MVC | 19.87 (4% Tween) | Needle | 1.29 | 9.18 | 40.4 | Yes |
| PEO | | MVC | 30.40 (4% Tween) | Needle | 1.27 | 9.82 | 39.2 | Yes |
| PEO | | MVC | 39.84 (4% Tween) | Needle | 1.30 | 10.18 | 39.6 | Yes |
| PVP (360k) | 10% (7/3: CHCl$_3$/ MeOH) | DPV | 10% | Needle | — | — | — | Yes |
| PVP (360k) | 10% | DPV | 20% | Needle | — | — | — | Yes |
| PVP (360k) | 10% | DPV | 40% | Needle | — | — | — | Yes |
| PEO (400k) | 10% | DPV | 10% | Needle | — | — | — | Yes |
| PEO (400k) | 10% | DPV | 20% | Needle | — | — | — | |
| PEO (400k) | 10% | DPV | 40% | Needle | — | — | — | Yes |
| PCL (80k) | 10% | DPV | 20% | Needle | — | 1.98 | 26.4 | Yes |
| PCL (80k) | 10% | DPV | 40% | Needle | — | 2.52 | 26.1 | Yes |
| EC(22cp) | 16% (CF$_3$CH$_2$OH) | DPV | 10% | Needle | — | — | — | Yes |
| EC | 16% | DPV | 20% | Needle | — | — | — | Yes |
| EC | 16% | MVC + ETR + RAL | (8% + 8% + 8% | Needle | — | — | — | Yes |
| EC | 16% | (DPV + TFV) | (10% + 20%) | Needle | — | — | — | Yes |
| PMA A-co- PMM A(120k) | 12% (4/1 MeOH/ DMF) | DPV | 20% | Needle | — | — | — | Yes |
| PMA A-co- PMMA | 12% | DPV | 40% | Needle | — | — | — | Yes |
| EC | 7% | TFV + LNG + DPV | (20% + 20% + 20%) | Needle & Nanospider | — | — | — | Yes |
| PLGA | 10% | DPV + TFV | (17% + 17%) | Nanospider | — | — | — | Yes |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are systems and methods incorporating electrospun fibers and related materials, drugs agents compatible with such fibers and materials, designs and compositions arising from the described systems and methods, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or other reasons. When any such inclusion or deletion occurs, the specification is herein deemed to contain the group as modified.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, patents and printed publications referred to herein are individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A drug delivery composition comprising at least two drug agents comprised by electrospun polymer fibers, wherein said at least two drug agents include a drug agent that is hydrophobic and a drug agent that is hydrophilic, and wherein the electrospun polymer fibers include fibers that comprise said at least two drug agents dispersed along an axis of the fibers, and wherein the electrospun polymer fibers include fibers that comprise said at least two drug agents in the same fiber.

2. The drug delivery composition of claim 1 wherein the at least two drug agents in the same fiber are arranged in a uniaxial or coaxial configuration.

3. The drug delivery composition of claim 1 wherein the fibers are degradable.

4. The drug delivery composition of claim 1 in which said electrospun fibers comprise a said drug agent present in a range of 0.01%-70% by weight.

5. The drug delivery composition of claim 1 in which the different drug agents are released with differing kinetics upon contact of said composition with a hydrating fluid.

6. The drug delivery composition of claim 1 in which at least one of said drug agents modifies the release characteristics of at least one other drug agent from said fibers.

7. The drug delivery composition of claim 1 in which release characteristics are modified by the inclusion of an excipient in the solution from which fibers are electrospun.

8. The drug delivery composition of claim 1 wherein at least one drug agent is less than 10% crystalline particulate dispersion or less than 10% amorphous particulate dispersion.

9. The drug delivery composition of claim 1, wherein the drug agents include an antimicrobial drug and a contraceptive agent.

10. The drug delivery composition of claim 9, wherein the antimicrobial drug comprises an antiviral drug.

11. The drug delivery composition of claim 9, wherein the antimicrobial drug comprises an antiretroviral drug.

12. The drug delivery composition of claim 11 wherein the antiviral drug comprises a drug selected from the group consisting of a viral entry inhibitor, a reverse-transcriptase inhibitor, and an integrase inhibitor.

13. The drug delivery composition of claim 11 wherein the antiviral drug is selected from the group consisting of miraviroc (MVC), cyanovirin-N(CV-N), tenofovir (TFV), dapivirine (DPV), etravirine (ETR), azidothymidine (AZT), acyclovir (ACV), raltegravir (RAL) and glycerol monolaurate (GML).

14. The drug delivery composition of claim 9 wherein the contraceptive agent comprises a hormonal or non-hormonal contraceptive drug.

15. The drug delivery composition of claim 9 wherein the contraceptive agent comprises levonorgestrel.

16. The drug delivery composition of claim 1 wherein the fibers further form a physical barrier to sperm penetration when contacted with the vagina.

17. The drug delivery composition of claim 1 wherein the polymer fibers comprise or are spun from a polymer selected from the group consisting of poly(lactide-co-glycolide) (PLGA), polylactic acid (PLA), poly ε-caprolactone (PCL), polyvinyl alcohol (PVA), polyethylene oxide (PEO), polyvinylpyrrolidone (PVP), poly methacrylic acid (PMAA) and ethyl cellulose (EC).

18. The drug delivery composition of claim 1, formulated for delivery to the vaginal or rectal mucosa.

19. A method for producing the composition of claim 1, wherein the composition comprises a contraceptive drug agent and an antimicrobial drug agent that is an antiviral agent, wherein the composition is produced by providing a quantity of at least one solution, and electrospinning the solution onto a substrate.

20. A method of making a drug delivery composition comprising electrospinning a polymer fiber comprising at least two different drug agents dispersed along an axis of the fiber, wherein said at least two drug agents include a drug agent that is hydrophobic and a drug agent that is hydrophilic.

21. The composition of claim 1, wherein the drug agent that is hydrophobic and the drug agent that is hydrophilic differ in an aqueous solubility by at least an order of magnitude.

\* \* \* \* \*